US009150904B2

(12) United States Patent
Parker et al.

(10) Patent No.: US 9,150,904 B2
(45) Date of Patent: Oct. 6, 2015

(54) COINCIDENCE DETECTION

(75) Inventors: Peter Parker, London (GB); Michela Perani, London (GB)

(73) Assignee: King's College London, London (GB)

( * ) Notice: Subject to any disclaimer, the term of this patent is extended or adjusted under 35 U.S.C. 154(b) by 146 days.

(21) Appl. No.: 13/806,050

(22) PCT Filed: Jun. 23, 2011

(86) PCT No.: PCT/GB2011/000953
§ 371 (c)(1),
(2), (4) Date: Dec. 20, 2012

(87) PCT Pub. No.: WO2011/161420
PCT Pub. Date: Dec. 29, 2011

(65) Prior Publication Data

US 2013/0171644 A1 Jul. 4, 2013

(30) Foreign Application Priority Data

Jun. 23, 2010 (GB) .................................. 1010598.9

(51) Int. Cl.

| | |
|---|---|
| ***C12Q 1/68*** | (2006.01) |
| ***G01N 33/53*** | (2006.01) |
| ***C12N 15/10*** | (2006.01) |
| ***C12N 15/62*** | (2006.01) |
| ***G01N 33/68*** | (2006.01) |

(52) U.S. Cl.
CPC .............. *C12Q 1/68* (2013.01); *C12N 15/1055* (2013.01); *C12N 15/62* (2013.01); *C12Q 1/6804* (2013.01); *G01N 33/6842* (2013.01); *G01N 33/6845* (2013.01)

(58) Field of Classification Search
None
See application file for complete search history.

(56) References Cited

U.S. PATENT DOCUMENTS

2008/0214408 A1 * 9/2008 Chatterjee et al. ................ 506/9

* cited by examiner

*Primary Examiner* — James Martinell
(74) *Attorney, Agent, or Firm* — Thomas G. Peterson; Bradley Arant Boult Cummings LLP

(57) ABSTRACT

The invention relates to a method of detecting the coincidence of two biomolecular structures in a solid phase sample, said method comprising: (i) providing a first and a second fusion protein, each fusion protein comprising (a) a detection domain, said detection domain comprising a DNA binding domain; said detection domain capable of binding a cognate specific nucleotide sequence in co-operation with a further detection domain; (b) a recognition domain, said recognition domain capable of binding a target biomolecular structure; and (c) a connector domain; said connector domain being fused at one end to the detection domain and being fused at the other end to the recognition domain; wherein at least two of (a), (b) and (c) are heterologous to one another; wherein the recognition domains of said first and said second fusion proteins are capable of binding to first and second biomolecular structures; (ii) contacting the sample with said first and second fusion proteins; (iii) incubating to allow binding; (iv) removing unbound fusion protein; (v) contacting the sample with nucleic acid comprising said cognate specific nucleotide sequence; (vi) incubating to allow heterotrimeric binding of the nucleic acid; (vii) detecting nucleic acid bound to the sample wherein detection of nucleic acid in step; (vii) indicates that the two biomolecular structures are present coincidentally in said sample.

9 Claims, 26 Drawing Sheets

Figure 1
| | |
|---|---|
| **AGGTCA**NNNNN**AGGTCA** | HRE-DR5 |
| **AGGTCA**NNNN**AGGTCA** | HRE-DR4 |
| **AGGTCA**NNN**AGGTCA** | HRE-DR3 |
| **AGGTCA**NN**AGGTCA** | HRE-DR2 |
| **AGGTCA**N**AGGTCA** | HRE-DR1 |
Figure 2
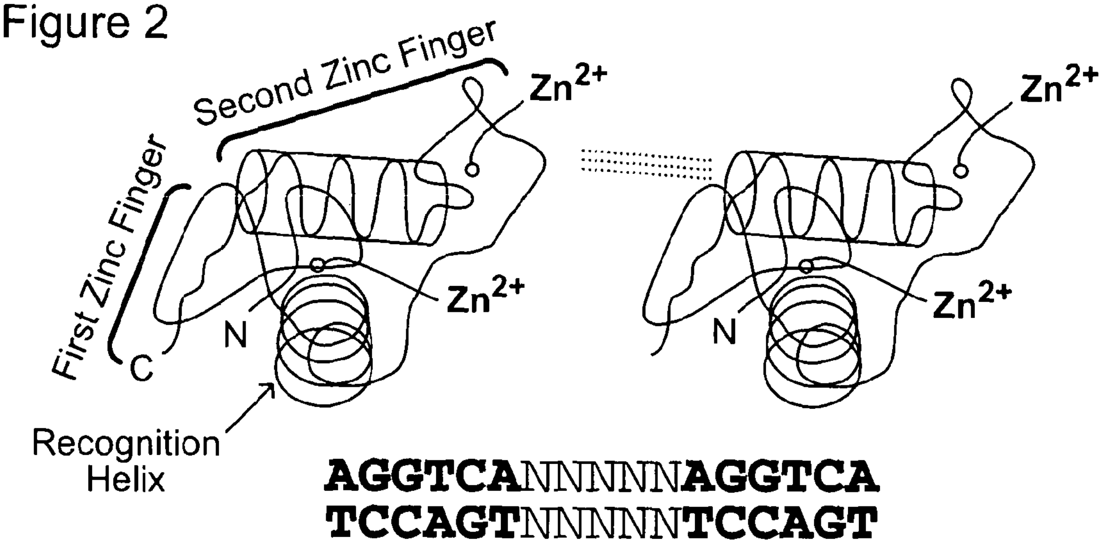
Figure 3
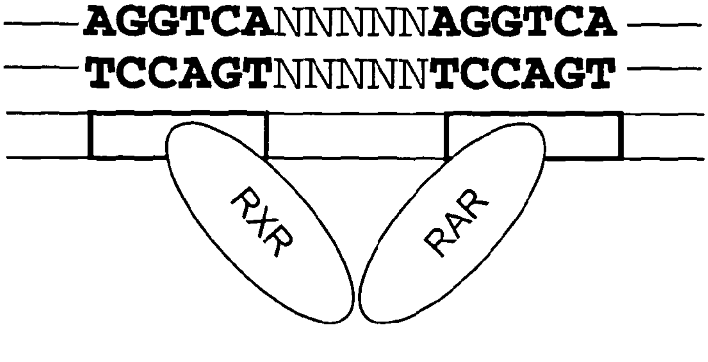

1

2

3

Figure 11 Continued
RESULTS
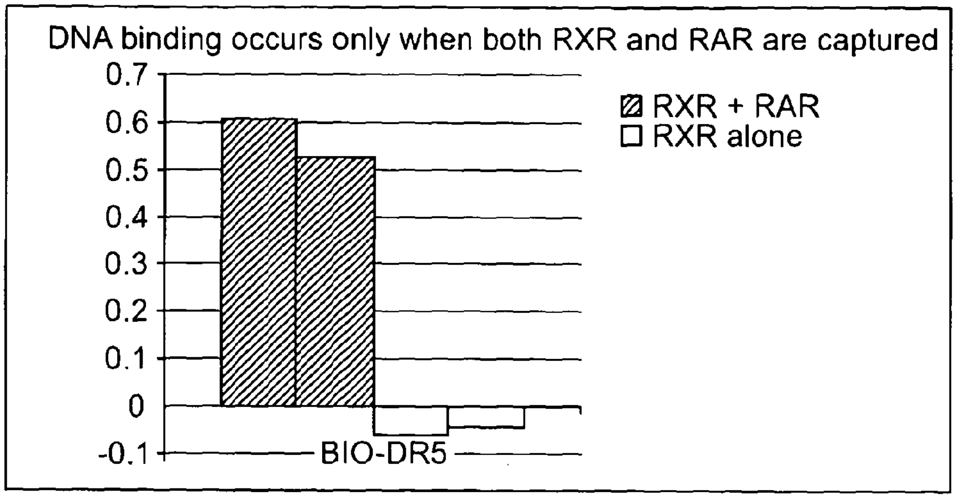
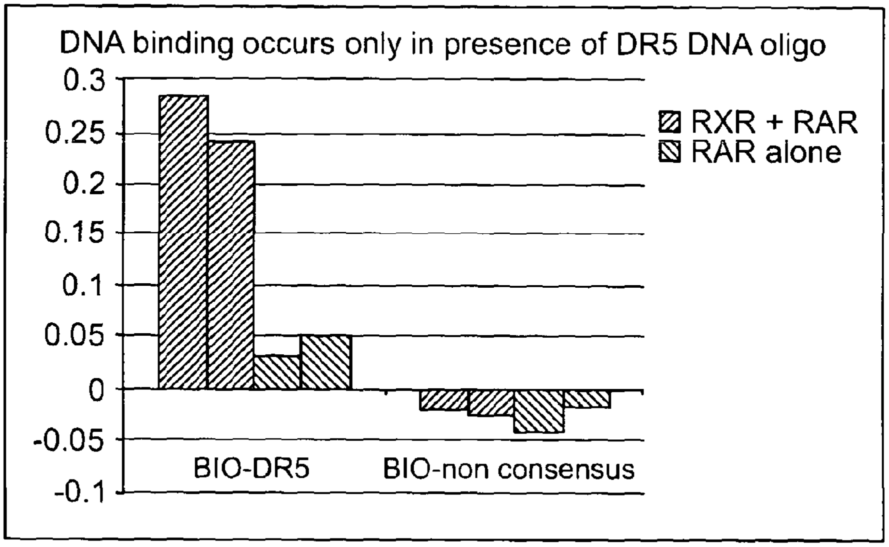
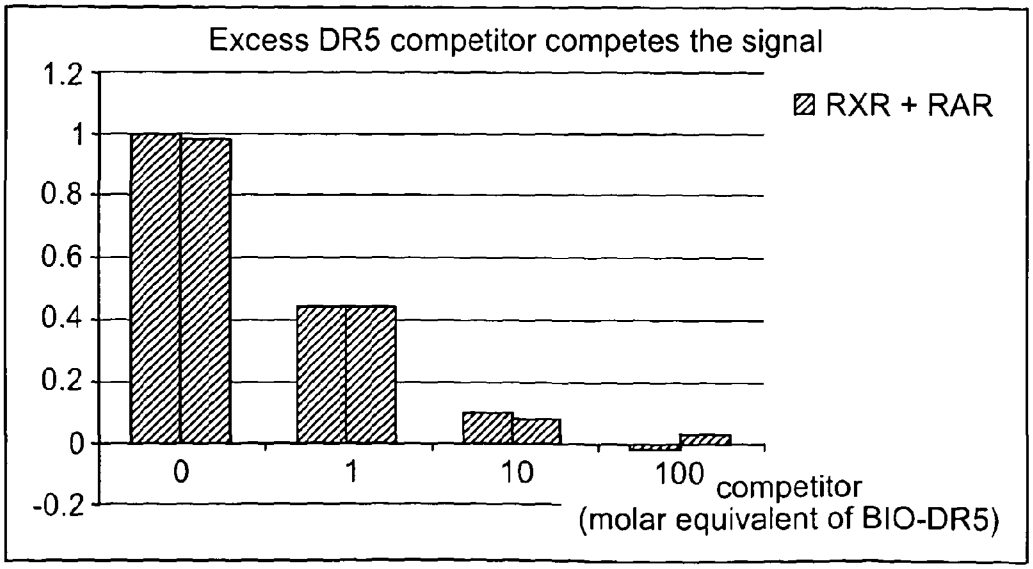

Figure 15 continued a Linear map of the RXR DNA BD

```
                                                   HphI
                                                   Sau96I
                                                    HaeIII
                                                    CviKI-1
                                                    BmgT120I
                                                  Sau96I
                                                  PspOMI
                                                   EcoO109I
                                                      Bsp1286I
                                                   BmgT120I
                                 StyD4I           EcoO109I
                                   ScrFI      StyD4I   BanII
                                 PspGI          ScrFI  BaeGI
                                   BstNI      PspGI NlaIV
                                 HaeIII         BstNI  ApaI
                  FaiI     AloI  CviKI-1       BsaJI NlaIV AloI  MnlI
                   \        \     \ \         \\\  \\\ \   \      \
     1  actttgtatagaaaagttggtggtggcctggaagttctgttccaggggccctccttcacc  60
        tgaaacatatcttttcaaccaccaccggaccttcaagacaaggtccccgggaggaagtgg
           ^    *    ^    *    ^    *    ^    *    ^    *    ^    *

  1     T  L  Y  R  K  V  G  G  G  L  E  V  L  F  Q  G  P  S  F  T    20

                                                             MnlI
                                                                TseI
                                Sau96I                          CviKI-1
                           BseRI BmgT120I                       AluI
                   Hin4I        AvaII  DdeI           BbvI RsaI Fnu4HI
                       FauI      NlaIV  [Bsu36I]       FaiI  TatI  PvuII
                   HinP1I     AciI   BsrBI     Cac8I BspCNI BsrGI MspA1I
                     HhaI  BslI  MwoI      MwoI   MnlI BseMII CviQI BisI
          HpyAV       GlaI MwoI BccI AciI     BsmFI     Hin4I Hpy166II
           \          \\\ \ \ \\ \ \\\\ \    \ \ \   \ \    \\\ \   \\\\  \\
    61  aagcacatctgcgccatctgcggggaccgct[cctcagg]caagcactatggagtgtacagc  120
        Ttcgtgtagacgcggtagacgcccctggcga[ggagtcc]gttcgtgatacctcacatgtcg
           ^    *    ^    *    ^    *    ^    *    ^    *    ^    *

 21     K  H  I  C  A  I  C  G  D  R  S  S  G  K  H  Y  G  V  Y  S    40
```

Figure 15 continued a Linear map of the RXR DNA BD

```
                                                Sau96I
                                           HinP1I
                                            GlaI AvaII
Fnu4HI                                      FspI PpuMI          AciI
 BlsI      MboII                         HpyCH4III    SetI        Fnu4HI
BisI       HpyCH4V       AgsI            MwoI HhaI BmgT120I        BisI
 SetI   MwoI      CviKI-1     AciI        FalI  Eco0109I  SetI  SetI
\\      \ \       \       \     \   \   \\\    \\    \     \      \ \
121  tgcgaggggtgcaagggcttcttcaagcggacggtgcgcaaggacctgacctacacctgc  180
     acgctccccacgttcccgaagaagttcgcctgccacgcgttcctggactggatgtggacg
         ^    *    ^    *    ^    *    ^    *    ^    *    ^    *
41   C  E  G  C  K  G  F  F  K  R  T  V  R  K  D  L  T  Y  T  C     60
```

```
                                         TseI
  BstUI                                   Fnu4HI
AciI                                        BlsI   HpaII
  TauI                                    BisI   BsrFI
Fnu4HI                                   TauI    BsaWI    TatI   AciI
 BlsI                                  Fnu4HI    AgeI BsrI CviQI   TauI
BisI                                    BlsI   NlaIV NlaIV RsaI Fnu4HI
    BspMI                              BisI MspA1I  BanI   ScaI BisI
    AarI                                AciI  AciI  BbvI    MwoI BlsI
\\\ \                                  \\\\\\ \ \\\ \\\    \\\\   \\\
181  cgcgacaacaaggactgcctgattgacaagcggcagcggaaccggtgccagtactgccgc  240
     gcgctgttgttcctgacggactaactgttcgccgtcgccttggccacggtcatgacggcg
         ^    *    ^    *    ^    *    ^    *    ^    *    ^    *
61   R  D  N  K  D  C  L  I  D  K  R  Q  R  N  R  C  Q  Y  C  R     80
```

Figure 15 continued a Linear map of the RXR DNA BD

```
                       FatI
                       StyI
                       NcoI
                       BtgI                                     TseI
                       BsaJI                                     Fnu4HI
                      HaeIII                                      BlsI
                      CviKI-1 BceAI                              BisI
                      MscI   FatI                               TauI
                    EaeI   NlaIII                             Fnu4HI
                 StyD4I CviAII FauI          MnlI              BlsI
                   ScrFI    MslI NlaIII          HpyCH4V   BisI
                   BstNI FaiI  FaiI          CviKI-1      BsrBI
                 PspGI  BslI  CviAII  AciI     TspDTI  MwoI AciI
                 \ \\ \\\\ \\\\\ \     \     \\ \ \     \  \\\\\\
241  taccagaagtgcctggccatgggcatgaagcgggaagccgtgcaggaggagcggcagcgt  300
     atggtcttcacggaccggtacccgtacttcgcccttcggcacgtcctcctcgccgtcgca
        ^    *    ^    *    ^    *    ^    *    ^    *    ^    *
81   Y  Q  K  C  L  A  M  G  M  K  R  E  A  V  Q  E  E  R  Q  R    100


            Hin4I
             HpaII                  TaqI  HinP1I
            BsaWI                  SalI      HhaI     RsaI
          Sau96I                     Hpy166II        CviQI
          AvaII                      HincII GlaI    TatI
     BseRI BmgT120I              HinfI   PleI       BsrGI
     BsgI BbvI    MnlI         SetI AccI  MlyI    Hin4I
     \    \\\\    \            \ \ \\\   \\\\\    \ \\\
301  ggcaaggaccggaacgagaatgaggtggagtcgaccagcgcaagtttgtacaaaaaa    360
     ccgttcctggccttgctcttactccacctcagctggtcgcgttcaaacatgtttttt
        ^    *    ^    *    ^    *    ^    *    ^    *    ^    *
101  G  K  D  R  N  E  N  E  V  E  S  T  S  A  S  L  Y  K  K      120
```

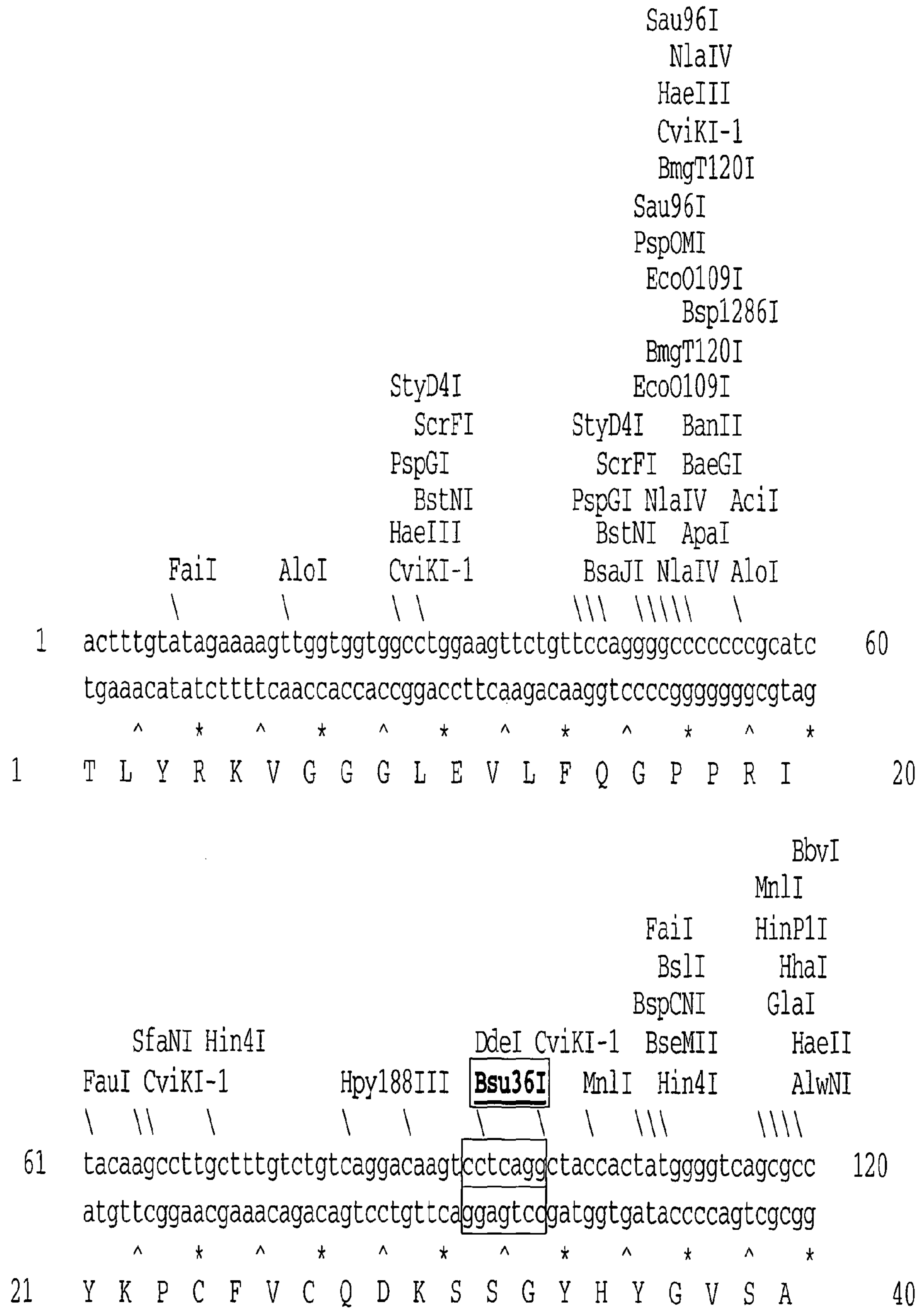

Figure 15 continued
b   Linear map of the RAR DNA BD

```
                                                      Sau96I
                                                      NlaIV
                                                      HaeIII
                                                      CviKI-1
                                                      BmgT120I
                                                      Sau96I
                                                      PspOMI
                                                      Eco0109I
                                                       Bsp1286I
                                                      BmgT120I
                                    StyD4I            Eco0109I
                                     ScrFI        StyD4I   BanII
                                   PspGI           ScrFI  BaeGI
                                    BstNI        PspG NlaIV  AciI
                                   HaeIII         BstNI  ApaI
         FaiI      AloI     CviKI-1             BsaJI NlaIV AloI
           \         \        \ \                \\\  \\\\\    \
  1   actttgtatagaaaagttggtggtggcctggaagttctgttccaggggcccccccgcatc   60
      tgaaacatatcttttcaaccaccaccggaccttcaagacaaggtccccggggggcgtag
         ^    *    ^    *    ^    *    ^    *    ^    *    ^    *
  1     T  L  Y  R  K  V  G  G  G  L  E  V  L  F  Q  G  P  P  R  I     20

                                                      BbvI
                                                      MnlI
                                              FaiI    HinP1I
                                               BslI     HhaI
                                             BspCNI    GlaI
             SfaNI Hin4I                 DdeI CviKI-1 BseMII   HaeII
         FauI CviKI-1          Hpy188III  Bsu36I  MnlI Hin4I   AlwNI
           \   \\    \              \    \    \   \    \\\    \\\\
  61  tacaagccttgctttgtctgtcaggacaagtcctcaggctaccactatggggtcagcgcc   120
      atgttcggaacgaaacagacagtcctgttcaggagtccgatggtgatacccagtcgcgg
         ^    *    ^    *    ^    *    ^    *    ^    *    ^    *
  21    Y  K  P  C  F  V  C  Q  D  K  S  S  G  Y  H  Y  G  V  S  A     40
```

Figure 15 continued b Linear map of the RAR DNA BD

```
                             PsrI                  HphI   Tsp45I
                              BtsCI                  HpyCH4IV
                             TseI                   AflIII
             EciI             Fnu4HI               RsaI  MaeIII
             MboII             BlsI               CviQI  TaiI
             HpyCH4V    FokI  BisI               TatI AflIII
          TseI             AciI            FatI  BsrGI PmlI
           Fnu4HI          Fnu4HI           CviAII  Hpy166II
            BlsI        AciI TauI  Hpy188III     Hpy166II
           BisI MwoI   MwoI BlsI      SfaNI NlaIII  BsaAI
          CviKI-1 CviKI-1  BisI    FalI BbvI FaiI MboII  SetI
          \\\\  \  \     \\  \\\\\    \    \  \\\ \ \\\\ \\ \
121  tgtgagggctgcaagggcttcttccgccgcagcatccagaagaacatggtgtacacgtgt  180
     acactcccgacgttcccgaagaaggcggcgtcgtaggtcttcttgtaccacatgtgcaca
        ^   *   ^   *   ^   *   ^   *   ^   *   ^   *
41   C  E  G  C  K  G  F  F  R  R  S  I  Q  K  N  M  V  Y  T  C     60

                                    BbvI
                                     HpaII    BsrI
                                   StyD4I   TseI
                                     ScrFI   Fnu4HI
      StyD4I                         NciI    BisI   RsaI
        ScrFI                   Tsp45I      MspA1I CviQI
        NciI                    MaeIII     AciI    TatI
       HpaII       HpyCH4V      BstEII   NlaIV BlsI  ScaI
          PsrI       BsmFI  SfaNI SetI    HphI      MwoI
      \\\ \          \ \     \    \ \ \\\   \ \ \\\   \\\\
181  caccgggacaagaactgcatcatcaacaaggtgacccggaaccgctgccagtactgccga  240
     gtggccctgttcttgacgtagtagttgttccactgggccttggcgacggtcatgacggct
        ^   *   ^   *   ^   *   ^   *   ^   *   ^   *
61   H  R  D  K  N  C  I  I  N  K  V  T  R  N  R  C  Q  Y  C  R     80
```

Figure 15 continued b Linear map of the RAR DNA BD

```
                              StyI
                            NlaIII
                        FatI  BsaJI
       HpyCH4V            FaiI
     SfcI                CviAII            PleI
         PstI      AgsI       NspI  HinfI   MlyI    BsiEI   HpyAV
     \ \ \         \      \\\ \ \    \       \\       \       \
241  ctgcagaagtgctttgaagtgggcatgtccaaggagtctgtgagaaacgaccgaaacaag  300
     gacgtcttcacgaaacttcacccgtacaggttcctcagacactctttgctggctttgttc
         ^    *    ^    *    ^    *    ^    *    ^    *    ^    *
81   L  Q  K  C  F  E  V  G  M  S  K  E  S  V  R  N  D  R  N  K    100

                   Bsp1286I
                NlaIV   BspCNI    DdeI  HinP1I
              BanI BaeGI            Hpy188I       RsaI
                SetI   BseMII         MwoI       CviQI
      MnlI       MboII  AvaI     Bsp1286I HhaI  TatI
         TaqII MboII    CviKI-1  BsiHKAI GlaI   BsrGI
      \  \     \ \\ \   \\       \\\ \  \\\     \\\
301  aagaagaaggaggtgcccaagcccgagtgctctgagagcgcaagtttgtacaaaaaa    360
     ttcttcttcctccacgggttcgggctcacgagactctcgcgttcaaacatgtttttt
         ^    *    ^    *    ^    *    ^    *    ^    *    ^    *
101  K  K  K  E  V  P  K  P  E  C  S  E  S  A  S  L  Y  K  K       120
```

Figure 16

FAR-WESTERN REAGENT

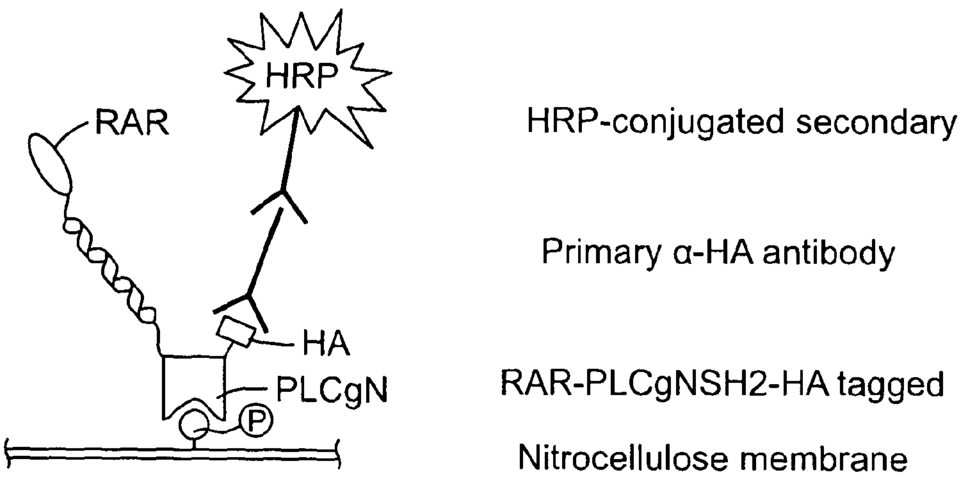

RAR-PLCgNSH2-HA detector reagent shows a robust and specific interaction with phosphorylated EGFR1

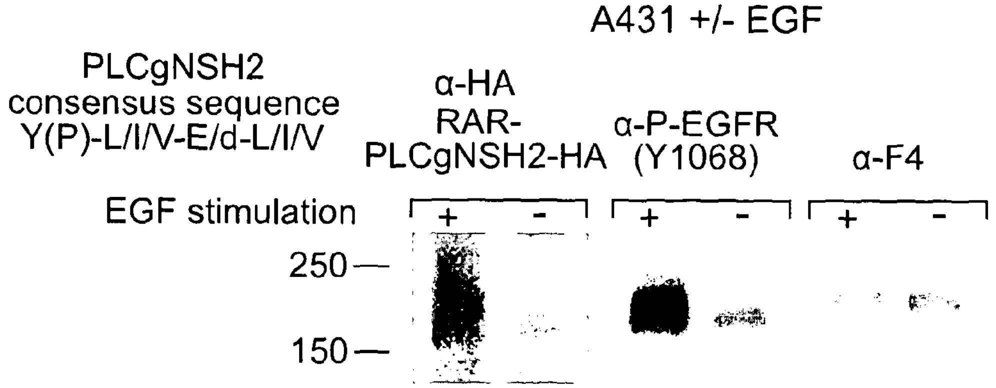

Far-westerns using A431 cell lysates detecting EGFR1 which contains PLCgNSH2 binding sites when phosphorylated. Cells were stimulated with 50ng/ml EGF (+) or left untreated (-) and extracts fractionated by PAGE and then probed with RAR-PLCgNSH2 tagged with HA and detected using α-HA antibody. RAR-PLCgNSH2 construct was used at 20 μg/ml (100 ug in ml, ~ 2.5 nmoles).

Figure 17
A: RAR-Protein G is functional and is able to bind the mouse monoclonal anti-F4 antibody
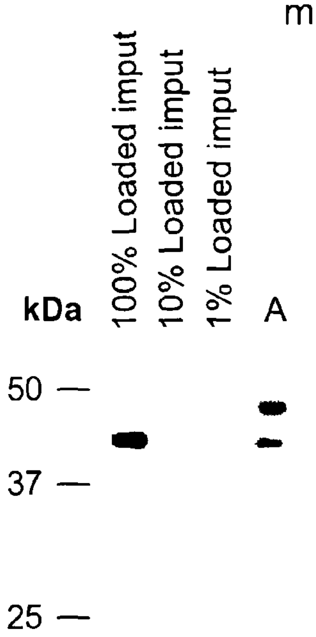
Western Blot
- Block with 5% BSA in TBS/Tw 1h RT
- anti-EE mouse monoclonal 1:500 in TBS/Tw, 1% BSA 1h RT
- antiMouse-HRP 1:15,000 in TBS/Tw, 1% BSA 30 min RT
A
RAR-ProtG
anti-F4
BIO-F4 peptide
Streptavidin Beads
B: Schematic diagram of the pull down assay
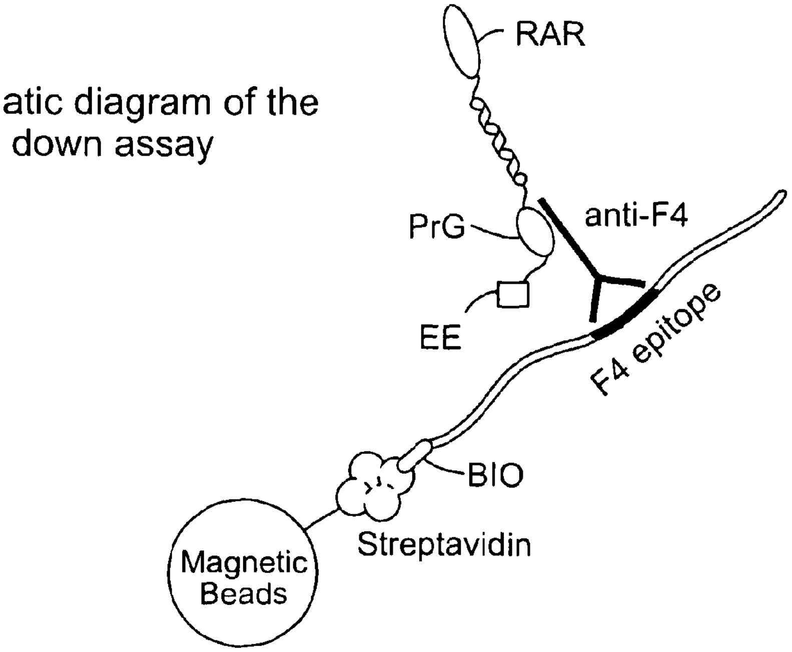

Figure 18
A: RXR & RAR modules function in a specific manner
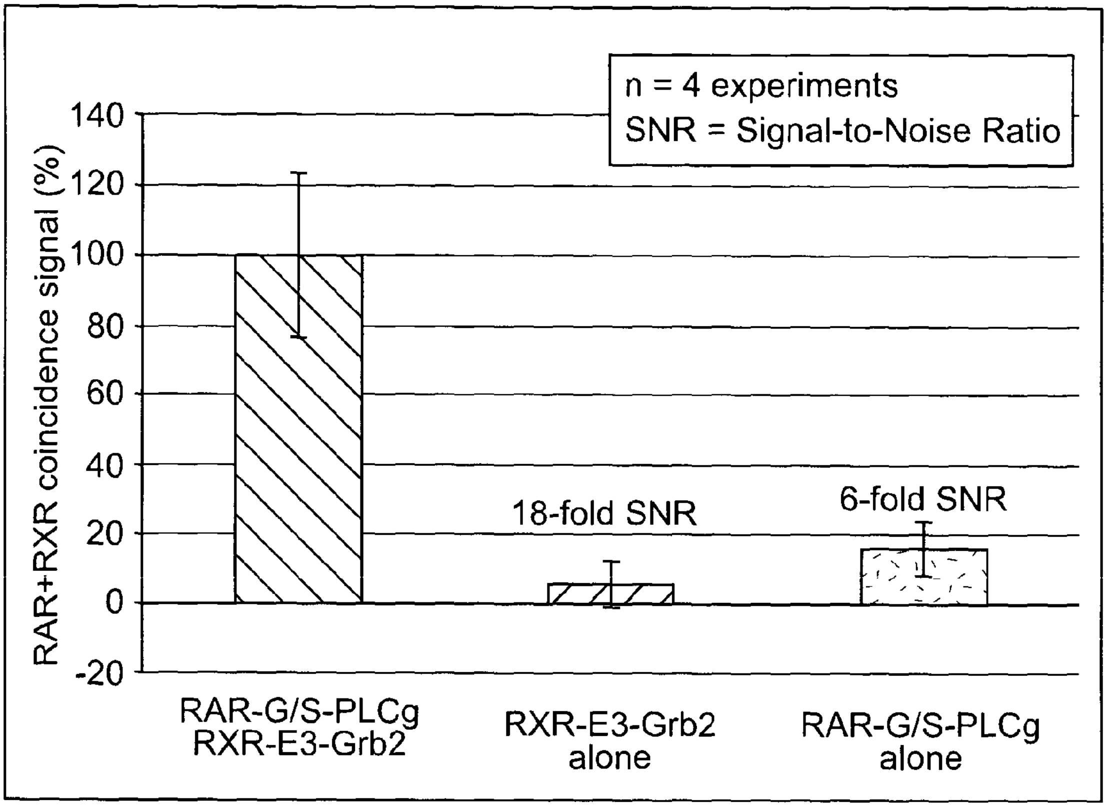
B: Schematic diagram
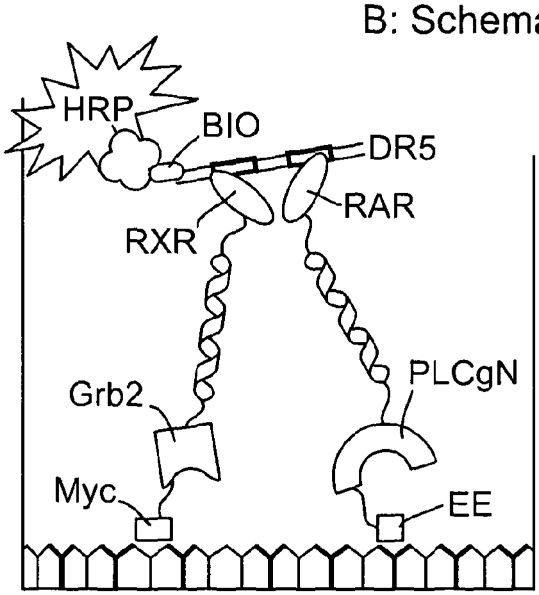
Well coated with α-MYC (Y) & α-EE (Y) Abs
The reagents are added in the following order:
- RXR-Grab2-MYC + RAR-PLCgN-EE
- Biotinylated dsOligo DR5
- Streptavidin-HRP conjugated
- TMB substrate Figure 19
A: The SH2 recognition modules specifically recognise phospho-tyrosine oligopeptides
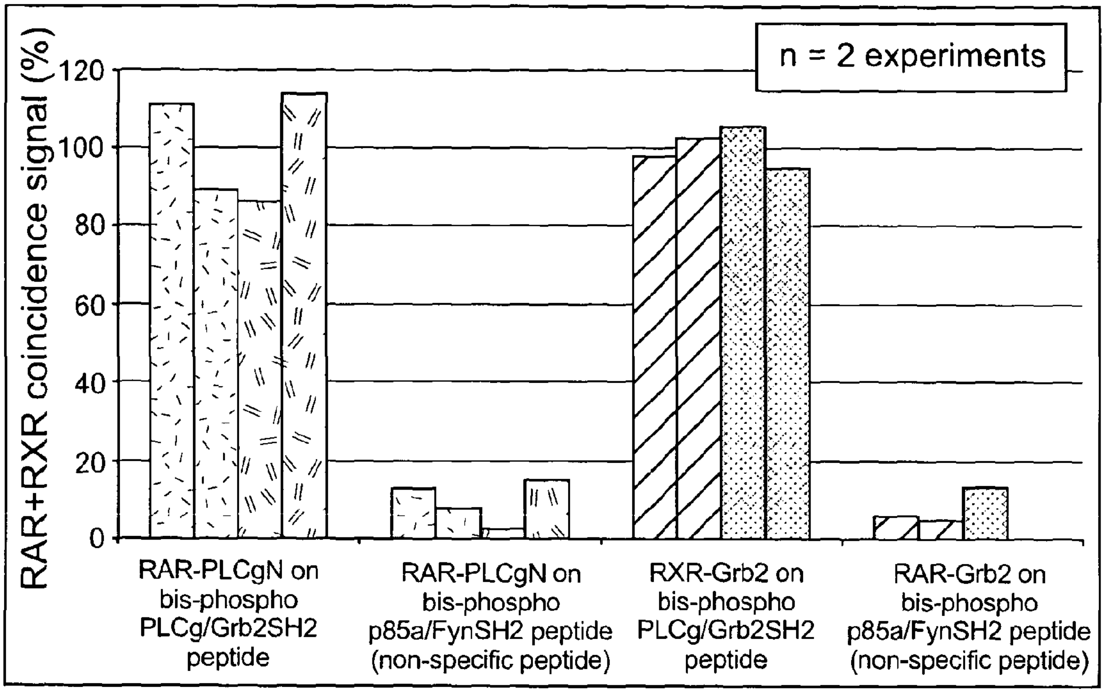
B: Schematic diagram
The reagents are added in the following order:
- Bis-phosphorylated biotin-oligopetide
- RXR-Grb2SH2-MYC tagged
- Primary α-MYC antibody
- HRP-conjugated secondary
- TMB substrate
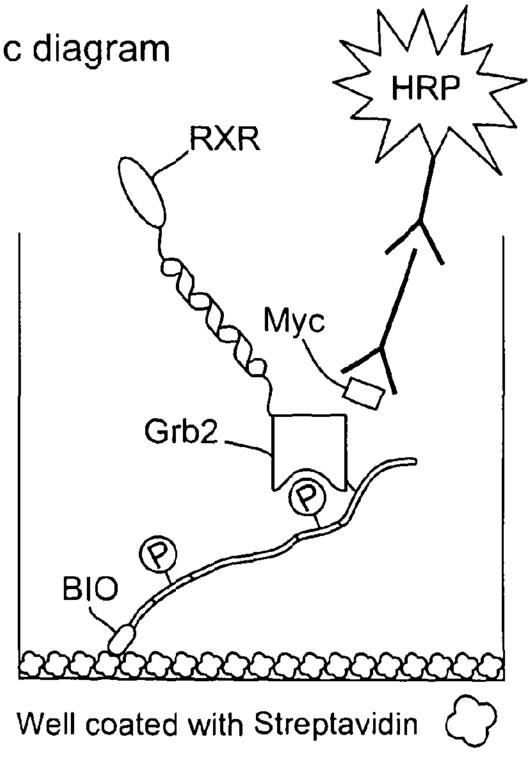

Figure 20
A: Coincidence detection signal is only obtained on specific bis-phosphotyrosine oligopeptide
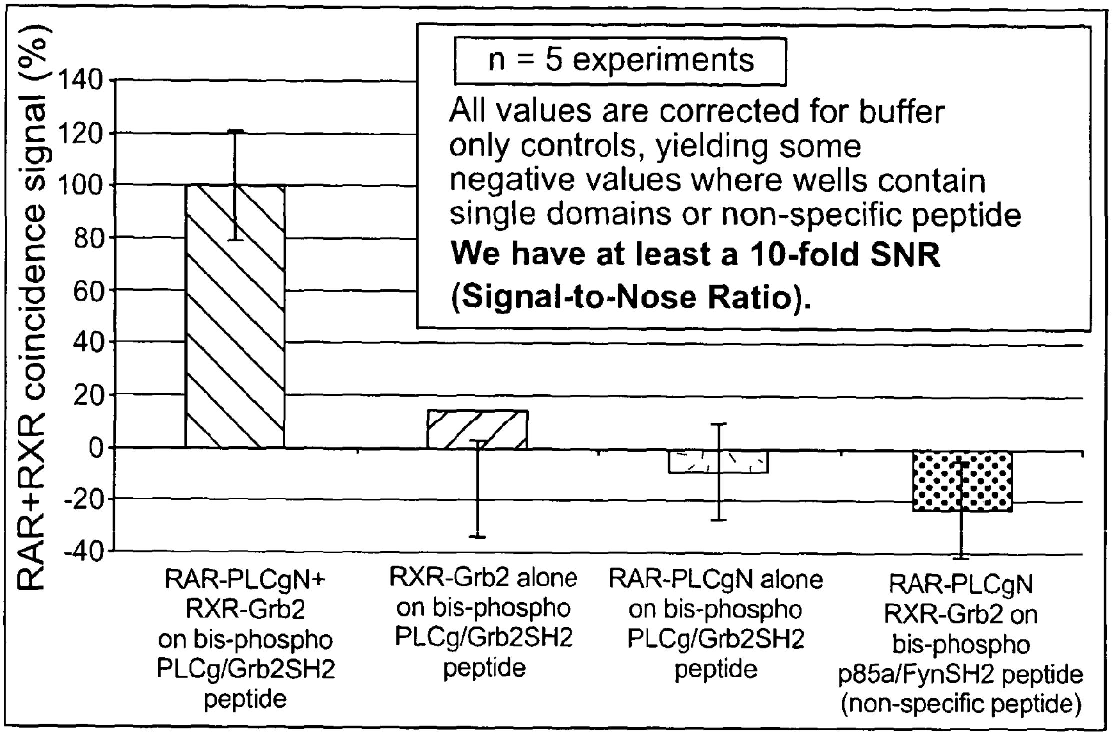
B: Schematic diagram
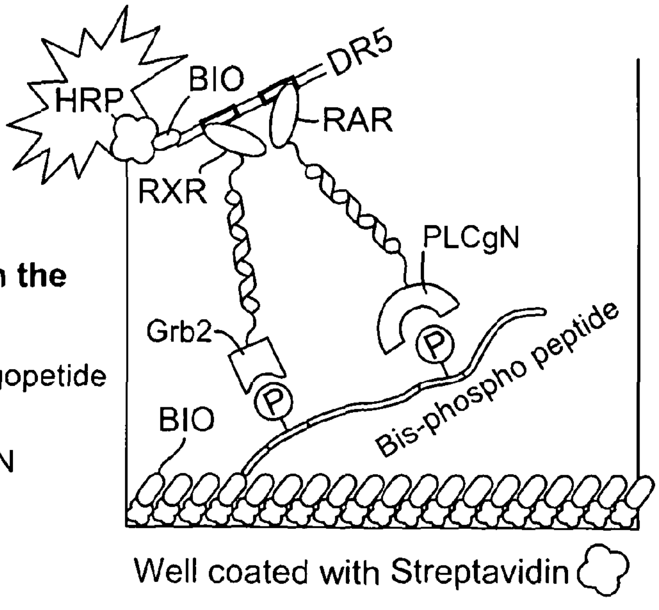
The reagents are added in the following order:
- Bis-phosphorylated biotin-oligopetide
- Free biotin block
- RXR-Grb2SH2 & RAR-PLCgN
- Biotin-DR5
- HRP-conjugated secondary
- TMB substrate Figure 21
A: Only specific mono-bis-phosphotyrosine oligopeptides compete coincidence signal
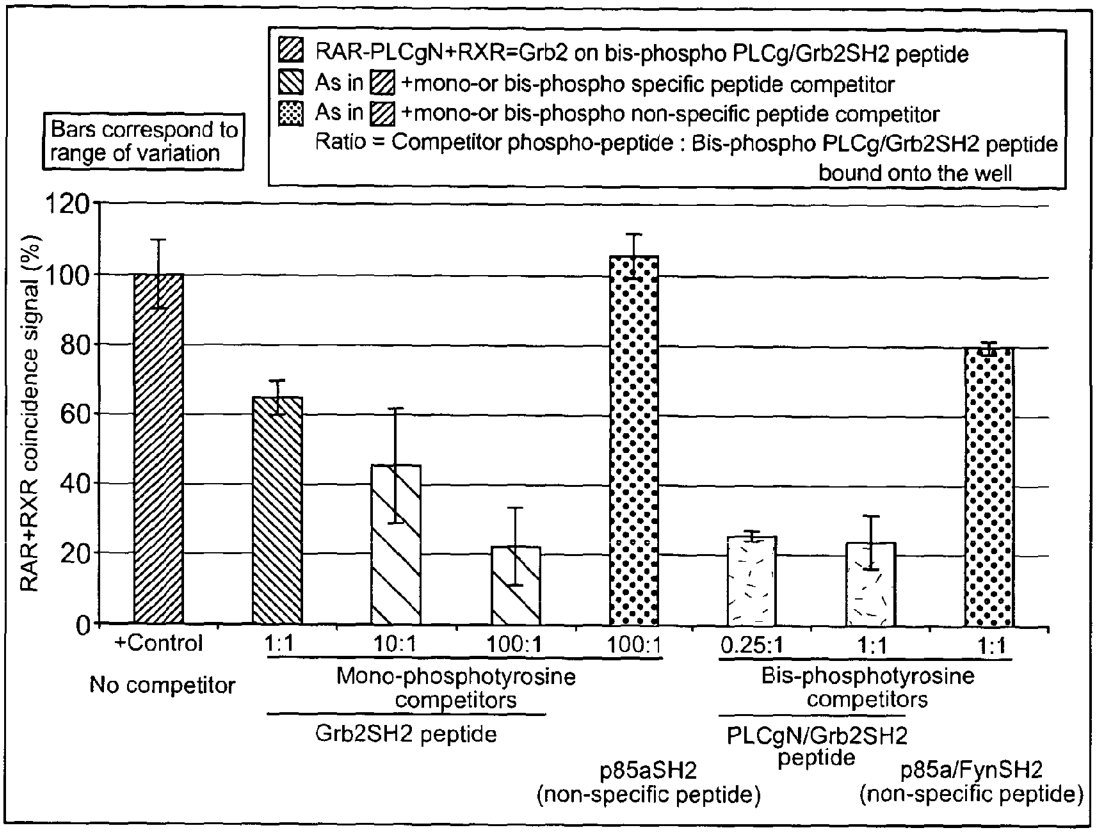
B: Schematic diagram
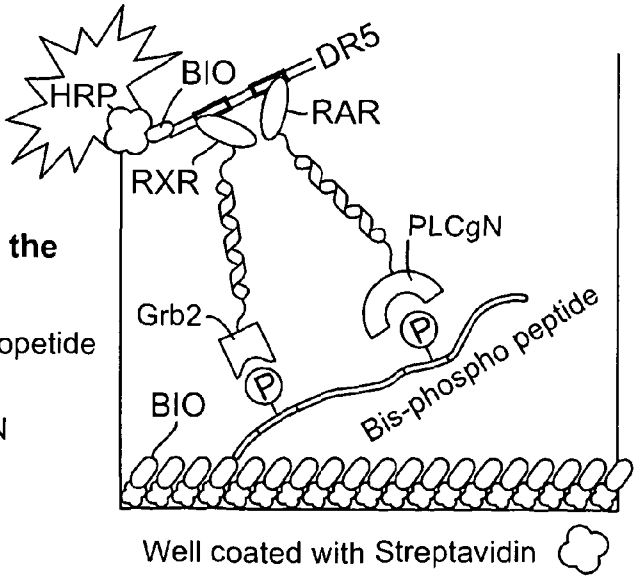
The reagents are added in the following order:
- Bis-phosphorylated biotin-oligopetide
- Free biotin block
- RXR-Grb2SH2 & RAR-PLCgN +\- competitor
- Biotin-DR5
- HRP-conjugated secondary
- TMB substrate Figure 22
A: The Zif268 DNA BDs of the fusions Zif268-G/S-ProteinG and ZIf268-E3-ProteinG are functional and bind to their cognate DNA sequence Zif268-DNA
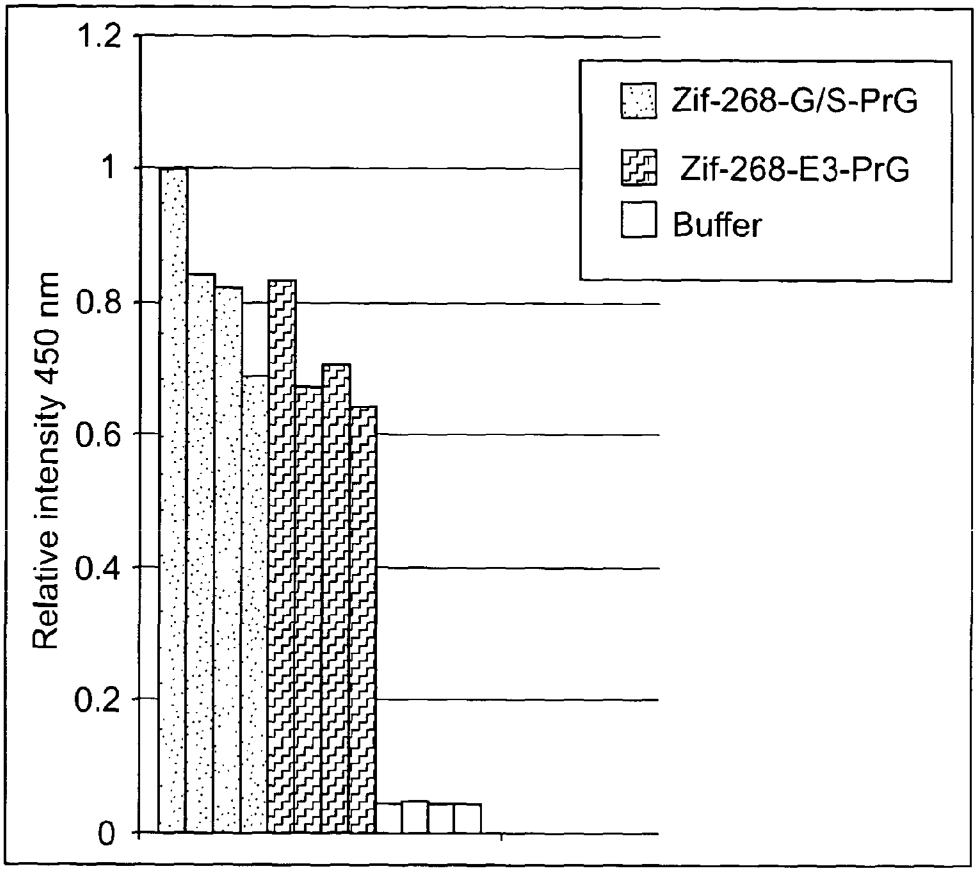
B: Schematic diagram
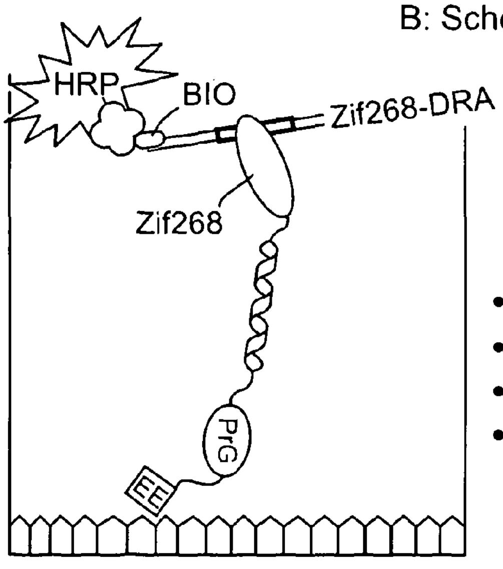
Well coated with α-EE (Y) Ab
The reagents are added in the following order:
- Zif-G/S-PrG-EE or Zif-E3-PrG-EE
- Biotinylated dsOligo Zif268-DNA
- Streptavidin-HRP conjugated
- TMB substrate

Figure 23

A: The ProteinG recognition domains of the fusions Zif268-G/S-ProteinG and ZIf268-E3-ProteinG are functional and bind specifically to the anti-F4 mouse monoclonal antibody

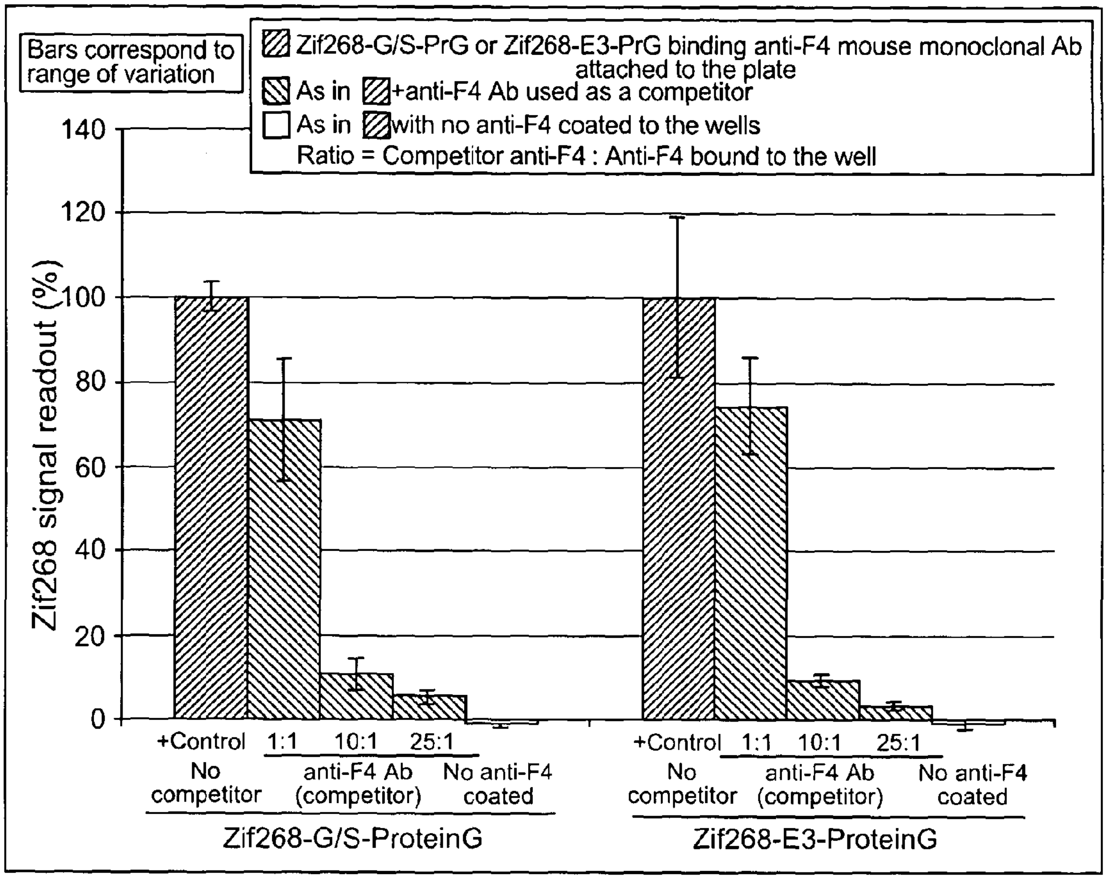

B: Schematic diagram

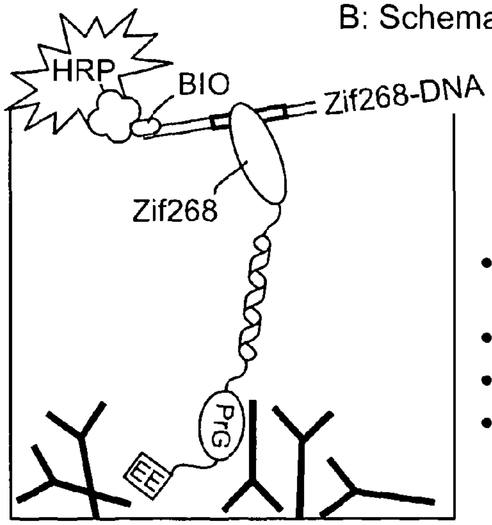

Well coated with α-F4 (Y) Ab

The reagents are added in the following order:

- Zif-G/S-PrG-EE or Zif-E3-PrG-EE +/-anti-F4 Ab (competitor)
- Biotinylated dsOligo Zif268-DNA
- Streptavidin-HRP conjugated
- TMB substrate Figure 24
A: The Zif268 DNA BDs of the fusions Zif268-G/S-ProteinG and ZIf268-E3-ProteinG bind specifically to their cognate DNA sequence Zif268-DNA
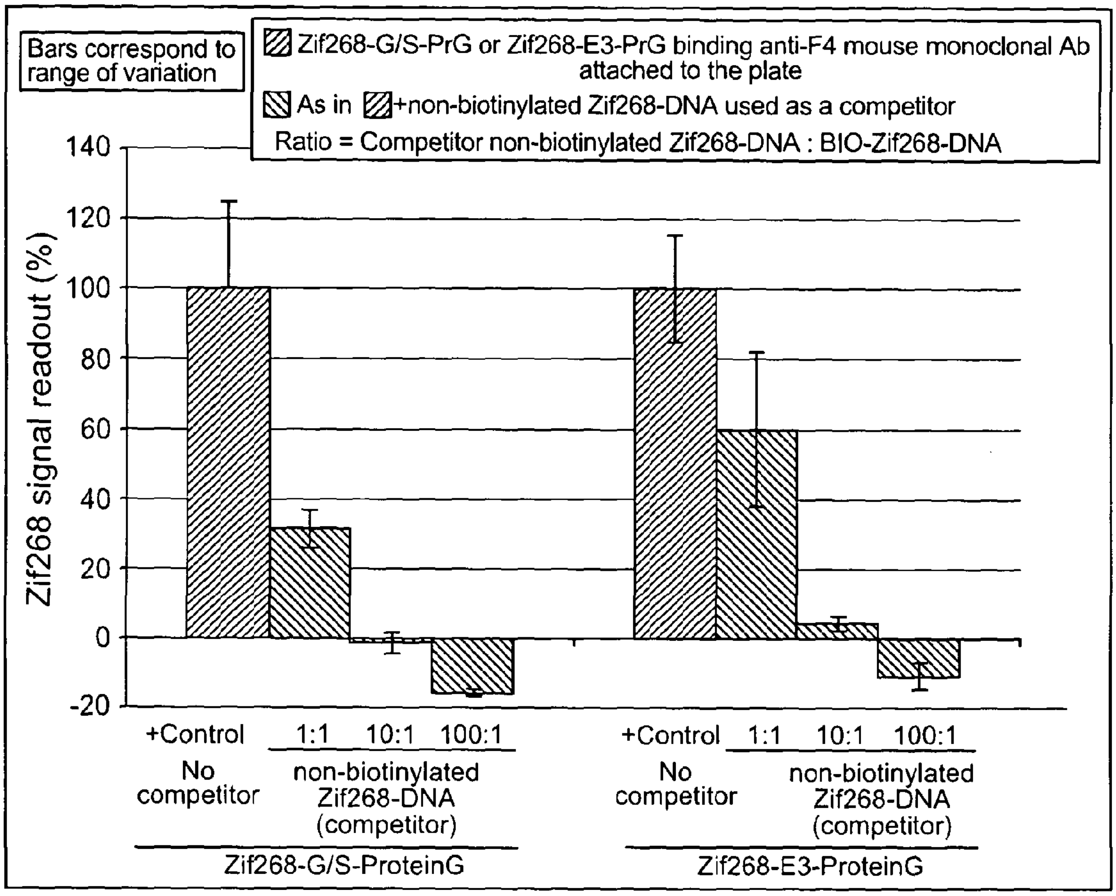
B: Schematic diagram
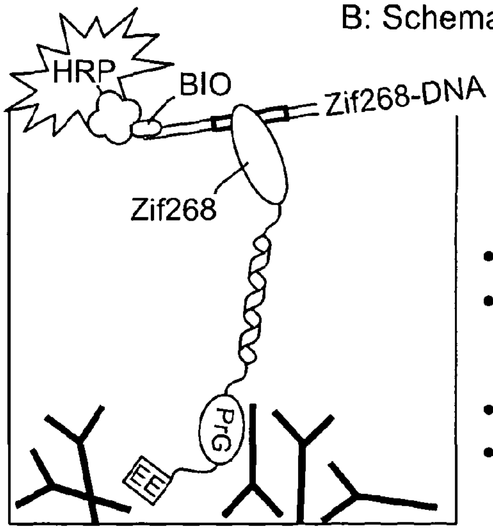
Well coated with α-F4 (Y) Ab
The reagents are added in the following order:
- Zif-G/S-PrG-EE or Zif-E3-PrG-EE
- Biotinylated dsOligo Zif268-DNA +/- non-Biotinylated Zif268-DNA (competitor)
- Streptavidin-HRP conjugated
- TMB substrate

COINCIDENCE DETECTION

CROSS-REFERENCE TO RELATED APPLICATIONS

This application is a national stage under 35 U.S.C. 371 of International Application PCT/GB2011/000953, filed on Jun. 23, 2011 (currently pending). International Application PCT/GB/2011/000953 cites the priority of British Patent Application 1010598.9, filed Jun. 23, 2010 (currently pending).

FIELD OF THE INVENTION

The invention relates to biological coincidence detection, and to reagents and methods for same.

BACKGROUND TO THE INVENTION

A significant challenge of biomedical research is the identification of biological markers (biomarkers) that can be used to predict and better understand the molecular basis of disease. A biomarker is defined as a substance or an event used as an indicator of a biological state that we want objectively to detect, measure and assess as a marker of a normal state, a pathological state (whether for predictive, prognostic or diagnostic purposes), or a pharmacologic response to a therapeutic intervention (a pharmacodynamic marker). The strong need to assess known biomarkers and discover new ones is because even in patients with the same disease altered molecular events in cells are not always similar; tumours, for example, are not the same at the molecular level even if they share common histological features. Thus, there is the need to understand the molecular mechanisms behind the development of diseases, to define specific molecular events, in order to recognize the molecular differences for each patient. In this way, patients can be stratified to receive the most appropriate therapies.

Nowadays, most of the data for pharmacological treatment efficacy or patient prognosis are based on statistical studies. As a result, the accuracy for predicting drug efficacy or prognosis in a single patient depends on the probability that he/she is near to the mean in large cohorts of patients. This approach is based on two approximations: "same tumour histotypes are equally responsive to therapy" and "each individual is pharmacologically equal to another". It is now widely documented that both the above assumptions are incorrect and there is an increasing need for personalised treatments.

Proteomic approaches attract increasing interest to identify and investigate biomarkers. A major advantage of measuring protein expression instead of their gene transcripts (using for example cDNA arrays) is that there is a variable correlation between mRNA expression levels and protein functional states and it is the latter that typically drive pathogenesis. Moreover, an important advantage of proteomics is the possibility of analysing post-translational modifications which are known to be important biomarkers since they can be altered in many diseases, such as cancer. However, due to the dynamic and complexity of protein networks, the technical difficulties encountered in specifically monitoring such changes in particular proteins are a challenge. Thus, this approach is still fraught with problems. One difficulty is to discover simple non-invasive diagnostic, prognostic and/or predictive methods to detect protein biomarkers and/or their post-translational modifications. It is thus of fundamental importance that the detailed knowledge surrounding molecular pathways responsible for the disease can be monitored in patient samples, such as the concentration of the proteins in these pathways and/or the knowledge of their functional states inside cells.

The most common and easy way to detect a protein is using antibodies, and there are commercially available antibodies that bind phosphorylated proteins. However, these antibodies in several cases are not mono-specific (i.e. recognise modifications on multiple proteins) and they are frequently polyclonal reagents with inherent batch variation issues (monoclonals have been difficult to produce). These issues pose problems when we want to investigate specific modifications such as phosphorylations associated with specific proteins.

Mass Spectroscopy (MS) is a different analytical technique that analyses complex protein samples. It is used to identify proteins, to identify post-translational modifications, to investigate protein interactions and to quantify protein expression. However, standard MS is used following isolation of the proteins from cell lysates or tissue samples and it does not provide any information on cellular localisation. On the other hand, a newer technology called Matrix-Assisted Laser Desorption/Ionization Imaging Mass Spectroscopy (MALDI IMS) combines the sensitivity and specificity of MS with imaging capabilities allowing the investigation of the spatial distribution of proteins, or phospho-proteins or many other biological molecules, from intact cells and tissues. The resolution here is limited to cells and is not subcellular. Furthermore, this approach demands very expensive equipment and is difficult to implement as a standard and routine laboratory procedure. In addition, the methodology is intrinsically limited by sensitivity and coverage—the modifications of choice may not be detected.

Fluorescent Resonance Energy Transfer (FRET) is an alternative coincidence detection technique which involves the transfer of energy from an excited donor fluorophore to an acceptor fluorophore which has an excitation spectrum that overlaps with the donor emission spectrum and is 59 nm away. Based on this principle, one of its applications is to fuse the donor and the acceptor fluorophores separately with two different target molecules. In the circumstances where these two molecules interact with each other, the donor and the acceptor fluorophores will be close enough to generate a FRET signal. FRET biodetectors can be easily introduced into cells and they are well suited for molecular imaging. However, FRET technology also requires a very expensive equipment set-up and substantial analytical resources, which is a problem.

Development of new techniques which require inexpensive technology are still a challenge and there is still a pressing need for high-throughput assays which are required to be inexpensive for standard and routine laboratory procedures.

A different kind of technology is the Duolink in situ Proximity Ligation Assay (PLA). Duolink in situ PLA is from the Swedish company Olink Bioscience. This technology enables detection, visualisation and quantification of individual proteins, protein modifications and protein interactions in tissue and cell samples prepared for microscopy. The assay is described below from an extract taken from the Duolink in situ PLA user manual (http://www.olink.com/). The six steps required are described:

- Primary Antibody Step—The sample of interest is incubated with two primary antibodies that bind to the protein/s to be detected. These antibodies have to be from two different species (e.g. mouse monoclonal and rabbit polyclonal).
- Secondary Antibody Step—Secondary antibodies are added which have been conjugated with two oligonucleotides named Proximity Ligation Assay probes (PLA probes) MINUS and PLUS.

Hybridisation Step—Two other oligonucleotides are added which will hybridise to the two PLA probes only if they are in close proximity.

Ligation Step—A reaction using ligase will then join the two hybridised oligonucleotides to form a closed circle.

Amplification Step—Polymerase and nucleotides are added and the oligonucleotide arm of one of the PLA probes acts as a primer for a rolling-circle amplification (RCA) reaction using the ligated circle as a template. This generates a concatemeric (repeated sequence) product extending from the oligonucleotide arm of the PLA probe.

Detection Step—Fluorescent labelled oligonucleotides are added which will hybridise to the RCA product. The signal is visible as a distinct fluorescent dot and can be analysed by fluorescent microscopy.

Thus the duolink technology is a complex multi-stage process. Moreover, duolink requires multiple antibodies from different species. In addition duolink relies on oligonucleotides conjugated to antibodies which can be a difficult and inefficient reaction. Thus duolink exhibits a number of drawbacks as well as being labour intensive and complicated to use.

The present invention seeks to overcome problem(s) associated with the prior art.

DESCRIPTION OF THE INVENTION

The inventors tackled the biological problem of detecting coincidence. In this context, coincidence means the occurrence together of more than one biomolecular structure of interest. For example, it may be desired to know whether or not a particular protein is phosphorylated. In this scenario, the first biomolecular structure is the protein itself and the second biomolecular structure is the phosphoryl group. When these structures are coincident, it is possible to infer that the protein is phosphorylated. Alternatively, it may be desirable to know whether or not two proteins are present in the same complex. In this scenario, a first biomolecular structure of interest is the first protein, and the second biomolecular structure of interest is the second protein. When these two proteins occur together, it can be inferred that they are in the same complex or are bound together.

As noted above, the prior art in this area suffers from numerous technical difficulties. The closest known system for accomplishing this type of analysis is the Duolink system. This system requires complex nucleic acid conjugates to be used. Moreover, once those conjugates have been prepared and applied to the sample being studied, this approach requires nucleic acid ligations to be performed which are fundamental to the read-out, adding further layers of technical complexity. Moreover, due to the covalently prepared reagents used in this system, the chemistry is rather inflexible and numerous different individual reagents need to be prepared in order to address only subtly different biological questions.

In contrast, the present inventors have exploited some of the properties of DNA binding proteins such as nuclear receptors and in particular their ability to bind their cognate DNA sequences as trimers. In particular, it is important that the binding of the DNA binding domain to their cognate DNA sequences only takes place in the form of a heterotrimer between two polypeptides, each bearing an amino acid sequence capable of recognising a half site within the specific cognate nucleotide sequence, and the nucleic acid sequence itself (i.e. the third component of the heterotrimer). The inventors have exploited this obscure biological phenomenon. In this regard, the invention is based on the production and use of individual fusion proteins which bring together selective biological properties in order to give a read out only when particular biomolecular structures are present together i.e.: are coincident.

Thus in one aspect the invention provides a method of detecting the coincidence of two biomolecular structures in a solid phase sample, said method comprising (i) providing a first and a second fusion protein, each fusion protein comprising (a) a detection domain, said detection domain comprising a DNA binding domain; said detection domain capable of binding a cognate specific nucleotide sequence in co-operation with a further detection domain;

(b) a recognition domain, said recognition domain capable of binding a target biomolecular structure; and (c) a connector domain; said connector domain being fused at one end to the detection domain and being fused at the other end to the recognition domain;

wherein at least two of (a), (b) and (c) are heterologous to one another;

wherein the recognition domains of said first and said second fusion proteins are capable of binding to first and second biomolecular structures;

(ii) contacting the sample with said first and second fusion proteins (iii) incubating to allow binding (iv) removing unbound fusion protein (v) contacting the sample with nucleic acid comprising said cognate specific nucleotide sequence (vi) incubating to allow heterotrimeric binding of the nucleic acid (vii) detecting nucleic acid bound to the sample wherein detection of nucleic acid in step (vii) indicates that the two biomolecular structures are present coincidentally in said sample.

Suitably the step of detecting nucleic acid bound to the sample comprises detection by total internal reflection (TIRF) analysis, or detection by fluorescence resonance energy transfer (or Forster Resonance Energy Transfer—FRET), or detection by fluorescence polarisation (FP) or detection by scintillation proximity technology. These techniques share the common property of being focussed on or selectively assaying the bound material i.e. the solid phase material. These techniques therefore do not collect signal from nucleic acid which may still be in solution or suspension at another location within the assay volume. Thus, collecting only the signal from any bound (immobilised) material provides the advantage of avoiding the need to remove unbound nucleic acid after the incubation before detection.

Suitably the step of detecting nucleic acid bound to the sample comprises (a) removing unbound nucleic acid; and (b) detecting nucleic acid bound to the sample.

The removal of the unbound nucleic acid before detection provides the advantage of reducing background and improving the signal to noise ratio. In addition, removing the unbound material before detecting the nucleic acid bound to the sample provides the advantage of permitting a wider range of detection techniques to be used, since the whole assay volume or area can be analysed when the unbound material has been removed, thereby simplifying and/or providing greater choice in the format of the detection step. For example, suitably detection of the nucleic acid bound to the sample is by polymerase chain reaction (PCR), by hybridisation to an oligonucleotide probe, by binding to a quantum dot nanocrystal, or by rolling circle amplification. More suitably detection of the nucleic acid bound to the sample is by hybridisation to an oligonucleotide probe, by binding to a quantum dot nanocrystal, or by rolling circle amplification.

In another aspect the sample is first contacted with an antibody capable of binding to a first molecular structure and wherein the recognition domain of one of said first or second fusion proteins is capable of binding to said antibody.

When the sample is pretreated with an antibody and the recognition domain of one of the fusions proteins is capable of binding said antibody, this binding to said antibody may be mediated by any known mechanism. For example, the recognition domain of the fusion protein may comprise part (such as an antigen binding fragment or scFv) of a 'secondary' antibody. For example if the pretreatment antibody ('primary' antibody) is a mouse antibody then the recognition domain of the fusion protein may suitably comprise an antigen binding fragment or scFv of a 'secondary' anti-mouse immunoglobulin; if the pretreatment antibody ('primary' antibody) is a goat antibody then the recognition domain of the fusion protein may suitably comprise an antigen binding fragment or scFv of a 'secondary' anti-goat immunoglobulin and so on.

Another mechanism which may be used is for the recognition domain to comprise a generic immunoglobulin-binding (antibody-binding) moiety i.e. an amino acid sequence capable of generically binding immunoglobulin or antibody. Examples of such amino acid sequences include protein A or protein G or protein L. Protein A and protein G bind to the Fc region of a range of immunoglobulins/antibodies; protein L binds immunoglobulins/antibodies through light chain interactions—the heavy chain is not involved in the binding to protein L. Proteins L/A/G are widely available commercially. These moieties have the advantage of binding amino acid sequences common to a range of antibodies (immunoglobulins) so that different individual reagents are not needed for different individual pretreatment antibodies. Thus when one recognition domain comprises a moiety capable of binding immunoglobulin sequences (such as a protein A or a protein G moiety) then suitably the other recognition domain does not comprise a sequence capable of being bound by protein A or protein G such as an Fc region. Similarly when one recognition domain comprises a moiety capable of binding antibody light chains (such as protein L), then suitably the other recognition domain does not comprise a sequence capable of being bound by protein L such as antibody light chains. Thus suitably the recognition domain of said first or second fusion protein capable of binding to said antibody comprises amino acid sequence of protein A or protein G or protein L.

Suitably said DNA binding domain comprises amino acid sequence derived from a nuclear receptor and said specific nucleotide sequence comprises a hormone response element.

Suitably said connector domain comprises a flexible amino acid sequence of approximately 5 to 15 nm in length.

In another aspect, the invention relates to a fusion protein, said fusion protein comprising:

i) a detection domain, said detection domain comprising a DNA binding domain; said detection domain capable of binding a cognate specific nucleotide sequence in co-operation with a further detection domain;

ii) a recognition domain, said recognition domain capable of binding a target biological molecule;

iii) a connector domain; said connector domain being fused at one end to the detection domain and being fused at the other end to the recognition domain;

wherein at least two of (i), (ii) and (iii) are heterologous to one another;

wherein said recognition domain comprises one or more of:

(a) a polypeptide capable of binding a mammalian immunoglobulin;

(b) a polypeptide which specifically binds to a target polypeptide sequence;

(c) a polypeptide which specifically binds a post translationally modified amino acid residue;

(d) an antibody variable heavy or light chain;

(e) a single chain variable fragment (ScFv); or (f) a polypeptide which specifically binds a backbone protein sequence.

When the recognition domain comprises (a) a polypeptide capable of binding a mammalian immunoglobulin, suitably said polypeptide is (ei) a polypeptide capable of binding the constant (Fc) region of a mammalian immunoglobulin; or (eii) a polypeptide capable of binding the light chain of a mammalian immunoglobulin.

Examples of a polypeptide capable of binding the constant (Fc) region of a mammalian immunoglobulin include protein A (e.g. SEQ ID NO:19) or protein G (e.g. SEQ ID NO:24) or fragments thereof which retain the binding function, or amino acid sequences having sufficient sequence identity thereto to retain the binding function. Examples of a polypeptide capable of binding the light chain of a mammalian immunoglobulin include protein L (e.g. SEQ ID NO:31) or fragments thereof which retain the binding function, or amino acid sequences having sufficient sequence identity thereto to retain the binding function.

When the recognition domain comprises (b) a polypeptide which specifically binds to a target polypeptide sequence, suitably said polypeptide comprises one or more of: an aptamer; an SH3 domain; a PTB domain; a PH domain; a LIM domain; a WD40 domain; a PDZ domain; a WW domain; an EVH1 domain; an EH domain or an Ankyrin repeat domain.

In another aspect, the invention relates to a fusion protein, said fusion protein comprising:

i) a detection domain, said detection domain comprising a DNA binding domain; said detection domain capable of binding a cognate specific nucleotide sequence in co-operation with a further detection domain;

ii) a recognition domain, said recognition domain capable of binding a target biological molecule;

iii) a connector domain; said connector domain being fused at one end to the detection domain and being fused at the other end to the recognition domain;

wherein at least two of (i), (ii) and (iii) are heterologous to one another;

wherein said recognition domain comprises one or more of:

(a) a polypeptide which specifically binds a post translationally modified amino acid residue (b) an antibody variable heavy or light chain (c) a single chain variable fragment (ScFv)

(d) a polypeptide capable of binding the constant (Fc) region of a mammalian immunoglobulin (e) a polypeptide capable of binding the light chain of a mammalian immunoglobulin.

In another aspect, the invention relates to a fusion protein, said fusion protein comprising:

i) a detection domain, said detection domain comprising a DNA binding domain; said detection domain capable of binding a cognate specific nucleotide sequence in co-operation with a further detection domain;

ii) a recognition domain, said recognition domain capable of binding a target biological molecule;

iii) a connector domain; said connector domain being fused at one end to the detection domain and being fused at the other end to the recognition domain;
wherein at least two of (i), (ii) and (iii) are heterologous to one another;
wherein said recognition domain comprises one or more of:
(a) a polypeptide which specifically binds a post translationally modified amino acid residue
(b) an antibody variable heavy or light chain
(c) a single chain variable fragment (ScFv)
(d) a polypeptide capable of binding the constant (Fc) region of a mammalian immunoglobulin.

In another aspect, the invention relates to a kit comprising
(a) a first fusion protein as described above; and
(b) a second fusion protein as described above; and
(c) a nucleic acid comprising a cognate specific nucleotide sequence as described above;
wherein said first and second recognition domains bind different target biological molecules, or bind different epitopes within a single biological molecule;
wherein binding of the first and second detection domains to the specific nucleotide sequence is by formation of heterotrimer.

Suitably said specific nucleotide sequence comprises a hormone response element.

Suitably the detection domain of the first fusion protein comprises nucleic acid binding domain of a 9-cis retinoid acid receptor (retinoid X receptor RXR)

Suitably the detection domain of the second fusion protein comprises a nucleic acid binding domain selected from the hormone receptor family.

Suitably the detection domain of the second fusion protein comprises a nucleic acid binding domain selected from the group consisting of all-trans retinoic acid receptor (RAR), thyroid hormone receptor (TR), the vitamin D3 receptor (VDR), the peroxisome proliferator activated receptor (PPAR) and the nerve growth factor induced-B receptor (NGFI-B).

Suitably the recognition domain of one of said first or second fusion proteins comprises amino acid sequence of protein A or protein G or protein L.

In another aspect, the invention provides direct detection of a biomolecular structure by binding a fusion protein to the biomolecular structure followed by detection via dimer formation between the single fusion protein and a single nucleic acid. In this aspect is provided a fusion protein, said fusion protein comprising:
i) a detection domain, said detection domain comprising a DNA binding domain; said detection domain capable of binding a cognate specific nucleotide sequence;
ii) a recognition domain, said recognition domain capable of binding a target biological molecule;
the detection domain and the recognition domain being fused;
wherein (i) and (ii) are heterologous to one another; and
wherein said recognition domain comprises protein G or protein A or protein L. In this aspect, suitably the DNA binding domain comprises a Cys2His2 type zinc finger. In this aspect, suitably the DNA binding domain of Zif268 (SEQ ID NO:23). In this aspect, there is also provided a kit comprising
(a) a fusion protein as described above; and
(b) a nucleic acid comprising a cognate specific nucleotide sequence as described above;
wherein binding of the detection domain to the specific nucleotide sequence is by formation of dimer.

In another aspect, the invention relates to a nucleic acid comprising a nucleotide sequence encoding a fusion protein as described above.

In another aspect, the invention relates to a fusion protein, said fusion protein comprising:
i) a detection domain, said detection domain comprising a DNA binding domain; said detection domain capable of binding a cognate specific nucleotide sequence in co-operation with a further detection domain;
ii) a recognition domain, said recognition domain capable of binding a target biological molecule;
iii) a connector domain; said connector domain being fused at one end to the detection domain and being fused at the other end to the recognition domain;
wherein at least two of (i), (ii) and (iii) are heterologous to one another.

The detection domain refers to the part of the fusion protein which is used to read out (ie: detect) coincidence. The detection domain is used to bind particular nucleic acids, and detection is typically based on conventional methods for determining the presence of those nucleic acids. It is an important feature of the fusion protein of the invention that the detection domain remains capable of binding its cognate nucleotide sequence co-operatively. In other words, a single detection domain on its own should not bind the nucleotide sequence. It is co-operation with a further detection domain which provides the binding. As used herein, the expression 'co-operative binding' or 'binds co-operatively' has its common meaning in the sense of needing both detection domains which together (i.e. co-operatively) allow formation of the heterotrimeric complex. This may also be expressed as binding together or binding in concert. In a strict biochemical sense, 'co-operative binding' may imply that the binding of one molecule at one site increases the affinity for the binding of the other molecule on a different site. This is the case for certain especially suitable pairs of DNA binding domains (for example RXR/RAR). However, the term 'co-operative binding' as used herein is intended to embrace the formation of trimeric complexes that do not exhibit strictly biochemically defined affinity-increasing-co-operative binding but do bind at each site independently i.e. that do require the other DNA binding domain to be co-localised in order to bind the nucleic acid in a heterotrimeric complex (i.e. the two DNA binding domains act to bind the nucleic acid 'together' or 'in concert' or 'co-operatively'). In this way, false positives caused by binding of the nucleotide sequence when only a single biological structure of interest is present is avoided. This is fundamental to the invention. This is explained in more detail below.

The recognition domain is the part of the fusion protein which actually binds the target biological molecule or biomolecular structure of interest. Thus, the recognition domain can be regarded as the "anchor" or "probe" which actually binds to or associates with one of the structures of interest. Thus, as explained below, the recognition domain may be an antibody fragment in order to detect a particular protein epitope, or may be an SH2 domain capable of binding phospho-tyrosine. This part of the fusion protein serves to localise the fusion protein to the actual biological entity of interest.

The connector domain can be thought of as an arm or a spacer. The function of the connector domain is to connect the detection domain to the recognition domain. Suitably the connector domain is of a modest length so as to avoid the reagent having an unnecessarily high molecular weight. The connector domain may be regarded as a tether holding the recognition domain and the detection domain together covalently. Suitably the connector domain may be a flexible amino acid sequence such as a well known linker (or kinker) sequence. This has the advantage that the recognition domain and the detection domain are reasonably unconstrained and suitably do not sterically hinder one another.

Suitably the connector domain may be a rigid linker for example a EKEliker, KEKlinker or MyoVllinker. These have the common property of being alpha helices and are therefore considered rigid structures.

In use, the fusion protein is exploited to localise the detection domain to the physical site of the biological structure of interest which is recognised by the recognition domain. In other words, the fusion protein is applied to a sample and it sticks or binds at locations where the recognition domain can bind to the structure of interest. A second fusion protein may be applied (either simultaneously or sequentially; simultaneous application typically saves labour) which recognises a different biological structure. Lastly, the specific nucleotide sequence is applied. Crucially, this nucleotide sequence is only able to be bound when both fusion proteins are present in the same physical location, permitting heterotrimer formation. This restricted binding is achieved as a direct result of deriving the amino acid sequence of the detection domain from a DNA binding protein (for example from a nuclear receptor DNA binding domain), because this type of protein domain will only bind the nucleotide sequence in co-operation i.e.: when a heterotrimeric complex is formed between the nucleotide sequence, and the first and second detection domains. In this way it can be immediately appreciated that a signal (binding of the nucleotide sequence) is only achieved when all three components are bound together. This is a key advantage of the invention in that detection of a signal directly and unambiguously indicates that the biological structures recognised by the two individual recognition domains present on each of the fusion proteins are in fact located in the same physical space. This important principle underlying invention is explained in more detail below.

An exemplary DNA binding domain comprises amino acid sequence derived from a nuclear receptor.

The phrase 'derived from' should have its natural meaning in the art and may include deriving the sequence in silico e.g. by use of sequence processing software; 'derived from' does not imply any direct physical tracing of the amino acid sequence to a 'donor' molecule; it is intended only to make clear from where the sequence has been taken. A sequence which is 'derived from' another may be 100% identical at the amino acid level, or may be mutated to a certain extent. A sequence will be considered to be 'derived from' another provided that it shares at least 60% sequence identity; suitably it shares at least 70% identity; suitably it shares at least 80% identity; suitably it shares at least 90% identity.

Suitably the detection domain is the amino acid sequence which forms the nucleic acid binding portion of the fusion protein. This typically includes at least the zinc finger motifs and any intervening sequence; most suitably this includes the zinc finger motifs and the recognition helix; this is discussed in more detail below.

Suitably said specific nucleotide sequence comprises a hormone response element. Hormone response elements provide nucleotide sequence specific binding sites to which the detection module(s) can bind.

Suitably said connector domain comprises a flexible amino acid sequence. Suitably said sequence is of approximately 5 to 9 nm in length. Suitably said sequence may be of approximately 5 to 24 nm in length; suitably 6 to 24 nm; suitably 5 to 15 nm; suitably 6 to 12 nm. A most suitable length is 5 to 15 nm. Different lengths (sizes) of connector sequence may be chosen for different applications of the invention. For example if it is desired to determine whether or not two biomolecular structures are within a certain distance of one another, the connector length may be correspondingly varied. Equally when it is possible that the two biomolecular structures of interest may be spatially constrained e.g. on opposite sides of a single protein, then the spatial separation should be taken into account when choosing the length of the connector domain for a particular application.

Suitably said recognition domain may comprise a polypeptide which specifically binds a post translationally modified amino acid residue. This has the advantage of allowing the determination of whether or not a particular protein has a specific post translational modification.

Suitably said recognition domain may comprise an antibody variable heavy and/or light chain. This advantageously permits a wide range of epitopes to which antibodies may have been raised to be used as the biomolecular structure(s) of interest.

Suitably said recognition domain may comprise a single chain variable fragment (ScFv). This allows a smaller sized fusion protein to be constructed which takes advantage of the specific binding properties of ScFv species. The interaction between VH and VL is weak, owing to a lack of stable pairing of the constant domains. A commonly used format of recombinant antibody FV domain expression in phage display is to use a peptide linker to maintain association as shown in FIG. 4D.

Suitably said recognition domain may comprise a polypeptide capable of binding the constant (Fc) region of a mammalian immunoglobulin. This advantageously allows 'sandwich' detection, for example when a mammalian immunoglobulin is first applied to the sample to bind to a particular biomolecular structure; the fusion protein of the invention then binds to the mammalian immunoglobulin, thereby detecting the biomolecular structure of interest indirectly. This has the advantage of simplifying reagent construction for example fusion protein(s) of the invention which bind the Fc region of mouse immunoglobulin may conveniently be used to detect any biomolecular structure which is recognised by an existing (e.g. commercially available) mouse antibody; the mouse antibody is simply applied to the sample before the fusion protein of the invention and the 'sandwich' allows coincidence detection. The same principle applies to other species of antibody for which such reagents are available, such as rabbit, goat, chicken, etc. This embodiment has the advantage of avoiding having to create a different fusion protein each time a different biomolecular structure is desired to be detected; the existing antibody to the biomolecular structure of interest can simply be applied before the fusion protein is applied and the remainder of the method(s) may be advantageously unaltered.

Suitably said recognition domain may comprise a polypeptide capable of binding the light chain of a mammalian immunoglobulin. For example, suitably said recognition domain may comprise protein L. This advantageously allows 'sandwich' detection, for example when a mammalian immunoglobulin is first applied to the sample to bind to a particular biomolecular structure; the fusion protein of the invention then binds to the mammalian immunoglobulin, thereby detecting the biomolecular structure of interest indirectly. This has the advantage of simplifying reagent construction.

Thus suitably said recognition domain may comprise protein A.

Suitably said recognition domain may comprise protein L.

Suitably said recognition domain may comprise protein G.

When said recognition domain comprises protein A or protein G or protein L, the fusion protein of the invention has the advantage that it is compatible with the use of any suitable primary antibody (i.e. any antibody which is bound by protein A or protein G or protein L respectively) of choice. Therefore in these embodiments the fusion protein of the invention exhibits wider application and a more modular or flexible set of applications in which it can be used without requiring molecular alterations beyond the choice of primary antibody to use.

Suitably when one of the fusion proteins has a recognition domain comprising protein A or protein G or protein L then suitably the other fusion protein does not comprise protein A or protein G or protein L. This has the advantage of avoiding false positive detection which might otherwise be caused by both fusion proteins binding a part of the same antibody and thereby falsely reporting coincidence.

In another aspect, the invention relates to a detection system or kit comprising (a) a first fusion protein as described above; and (b) a second fusion protein as described above; and (c) a nucleic acid comprising a cognate specific nucleotide sequence as described above;

wherein binding of the first and second detection domains to the specific nucleotide sequence is by formation of heterotrimer;

wherein said first and second recognition domains bind different target biological molecules, or bind different epitopes within a single biological molecule. In this embodiment the first and second fusion proteins are different. In this embodiment the first and second fusion proteins are capable of binding to the same single cognate specific nucleotide sequence in co-operation.

In one embodiment the invention may be used to detect the coincidence of different biological molecules.

In another embodiment the biomolecular structures of interest may in fact reside on the same biological molecule(s). This is the case for example when assaying for particular post-translational modifications. In this embodiment the different biomolecular structure(s) being detected need not be restricted to being different actual molecules. Moreover, the term “biomolecular structure” is used to help make this distinction clearer. The biomolecular structure may be a polypeptide epitope or may be a post translational group added to a protein or may even be a non-protein structure such as a phospholipid or nucleic acid or other such biomolecule. It should also be noted that in a strict sense the term ‘epitope’ might be understood to refer to a structure which is capable of inducing an immune response; the term ‘epitope’ as used herein is given its more ‘common parlance’ meaning simply to describe a distinct structure or part of a biomolecule which can be individually detected; it is not important to the performance of the invention whether or not the binding of the recognition domain to the biomolecular structure of interest is via any immune related mechanism (e.g. when the recognition domain comprises an antibody or fragment thereof and the biomolecular structure is therefore an ‘epitope’ in the strictest sense) or when the binding of the recognition domain to the biomolecular structure of interest is via any other mechanism (e.g. when the recognition domain is a Grb2 SH2 domain and the biomolecular structure may or may not form an ‘epitope’ in the strict sense of being capable of induction of an immune response). In these settings, the term ‘epitope’ is used merely to describe a distinct part of a biomolecule which is being bound by the recognition domain.

When said recognition domain comprises protein A or protein G or protein L, suitably the kit or detection system of the invention further comprises one or more primary antibodies capable of being bound by protein A or protein G or protein L.

Suitably said specific nucleotide sequence comprises a hormone response element.

Suitably the detection domain of the first fusion protein comprises the nucleic acid binding domain of a 9-cis retinoid acid receptor (retinoid X receptor RXR). This is an especially advantageous DNA binding domain to use.

Suitably the detection domain of the second fusion protein comprises nucleic acid binding domain selected from the group consisting of all-trans retinoic acid receptor (RAR), thyroid hormone receptor (TR), the vitamin D3 receptor (VDR), the peroxisome proliferator activated receptor (PPAR) and the nerve growth factor induced-B receptor (NGFI-B). These have the common property of forming heterodimers with RXR (or more accurately forming heterotrimers with RXR and the cognate specific nucleotide sequence).

In one embodiment suitably the detection domain of the first fusion protein comprises the nucleic acid binding domain of a 9-cis retinoid acid receptor (retinoid X receptor RXR) and the detection domain of the second fusion protein comprises nucleic acid binding domain selected from the group consisting of all-trans retinoic acid receptor (RAR), thyroid hormone receptor (TR), the vitamin D3 receptor (VDR), the peroxisome proliferator activated receptor (PPAR) and the nerve growth factor induced-B receptor (NGFI-B). This has the advantage of presenting pairs of detection domains which form especially effective heterotrimers with the cognate specific nucleotide sequence.

Suitably the detection system or kit as described above further comprises reagents for the detection of said specific nucleotide sequence. Suitably said reagents comprise one or more of a PCR primer, an oligonucleotide probe (not conjugated or tagged; or for example bearing a tag such as biotin or a fluorescent tag such as a fluorophore or a quantum dot nanocrystal which tag or tags may be attached by conjugation to the oligonucleotide), a single stranded circle for polymerase amplification (e.g. rolling circle amplification) and subsequent detection (for example with a further hybridising labelled (tagged) oligonucleotide probe), or a quantum dot nanocrystal. These modes of detection are particularly suitable for application to the invention.

In another aspect, the invention relates to a nucleic acid comprising a nucleotide sequence encoding a fusion protein as described above. More suitably the invention provides a kit comprising two or more nucleic acids each comprising a nucleotide sequence encoding a fusion protein as described above. This has the advantage of providing materials for preparation of first and second fusion proteins in a single kit.

In one embodiment multiple fusion proteins of the invention may be encoded on a single nucleic acid. This has the advantage of increased efficiency and/or minimising the number of reagents required to produce each component of a detection system of the invention.

In another aspect, the invention relates to a method of detecting the coincidence of two biomolecular structures in a solid phase sample, said method comprising (i) providing a first and a second fusion protein as described above (ii) contacting the sample with said first and second fusion proteins (iii) incubating to allow binding (iv) removing unbound fusion protein (v) contacting the sample with nucleic acid comprising a cognate specific nucleotide sequence as described above (vi) incubating to allow heterotrimeric binding of the nucleic acid (vii) removing unbound nucleic acid (viii) detecting nucleic acid bound to the sample wherein detection of nucleic acid in step (viii) indicates that the two biomolecular structures are present coincidentally in said sample.

When said recognition domain comprises protein A or protein G or protein L, suitably the above method comprises one or more further steps (iia) contacting the sample with one or more primary antibodies capable of binding the biomolecular structure(s) of interest; (iib) incubating to allow binding; (iic) removing unbound antibody. This advantageously allows detection of specific structures using available antibodies, which alleviates the need to produce further fusion protein(s) for the specific recognition of such structures, but rather enables a modular detection using available antibodies.

The sample used herein suitably comprises a solid phase. For example, the sample may be a western blot. For example, the sample may be fixed cells or tissue. Suitably the sample is any biological sample which is somehow fixed or anchored to a substrate. This is important because the very idea of coincidence detection is to understand whether or not two biomolecular structures are present at the same physical site. For this reason, the invention is best suited to applications in which the sample is physically immobilised. Suitably the sample is not a solution. A further reason why it is important that the sample comprises a solid phase is that the individual parts of the detection system, i.e.: the individual fusion proteins and the nucleotide sequence used for detection, have to be applied in manner to permit their binding (if any), but it is also important that excess reagent is washed away at the appropriate point before detection. The removal of excess reagents is of course important in order to avoid false positive detection for example, by formation of a heterotrimeric complex between the three components of the detection system when present together in solution. Thus, it is another advantage that the sample should comprise a solid phase in order to facilitate the easy removal of excess reagents such as via washing the sample with the appropriate buffers.

Definitions

The term ‘comprises’ (comprise, comprising) should be understood to have its normal meaning in the art, i.e. that the stated feature or group of features is included, but that the term does not exclude any other stated feature or group of features from also being present.

We describe a novel detection system (biodetector) for the analysis of multiple pathways in any given situation, for example in cancer patients, to be used for a range of purposes employing various source materials including: western blots, fixed cells and tissue samples. We describe a method that we call “coincidence detection,” wherein two separate affinity probes are used to detect a target molecule or molecules. We present a generic methodology and a repertoire of reagents for the detection of protein states in signalling pathways. We also provide a simple, reproducible, cost-effective, in situ kit, with the utility of its deployment for diagnosis, prognosis and/or treatment prediction.

Thus the present invention embraces a novel biodetector system that detects and visualises post-translational modifications on specific proteins, two proteins when they are in close proximity and/or detects/visualises proteins with high specificity. It is applicable for cell microscopy using fixed cells and tissues (including tissue arrays). It can be used also for western blot analysis such as analysis of signalling pathways.

In one embodiment there is described a novel device for coincidence detection composed entirely of recombinant proteins together with nucleic acid for readout/detection. It is useful to visualise and/or quantify proteins, their modifications or protein interactions by western blot or in fixed cells or tissue samples.

The detection system described is based on several important features: these are described with reference to the detection domains of the fusion proteins being derived from the DNA binding domains (DBDs) of RXR and RAR. It will be noted that these are exemplary DBDs and therefore exemplary fusion proteins—this discussion is not intended to limit the source of the DBDs to RXR/RAR.

1) The monomeric RXR and RAR DBDs display negligible binding to the consensus site;

2) The DBDs of RXR and RAR can generate essentially the same pattern of DNA selectivity and trimerisation with cognate specific nucleotide sequence as the full-length receptors;

3) The RXR and RAR DBDs in combination bind specifically and efficiently to the cognate specific nucleotide sequence which in this case is direct repeat DR5, thereby forming a heterotrimer.

It is a specific advantage of embodiments of the invention where the detection domain of first and second fusion proteins is derived from RXR and RAR that the 5 bp of the inter-half-site spacer that separates the two half-sites AGGTCA in the direct repeat DR5 is important for high cooperative binding between RXR and RAR DBDs. The inter-half-site spacer provides the geometry needed for receptor subunits to interact at their dimerisation interface. The sequence of the spacer is not as significant as its length.

It is a specific advantage of embodiments of the invention where the detection domain of first and second fusion proteins is derived from RXR and RAR that in addition to the main dimerisation interface of the ligand binding domains of full-length receptors, an additional dimer interface has been identified within the RXR and RAR DBDs. The latter, most selectively promotes cooperative DNA binding to the direct repeat DR5.

The biodetector therefore has the ability to generate a specific signal only when RXR and RAR (i) are in close proximity, (ii) simultaneously bind the DR5 DNA consensus sequence, and (iii) form a heterotrimeric structure with DR5. Thus, only when RXR, RAR and DR5 are in a trimeric complex can the signal be created (FIG. 4A); monomeric RXR and monomeric RAR do not bind to DR5 (FIG. 4B); RXR and RAR do not form heterodimers in the absence of DR5 (FIG. 4C).

Applications

The invention provides new reagents/tools for coincidence detection. These have many applications. For example, they may be applied to detect when the target molecule(s) have specific post-translational modifications. They may be applied to detect when two proteins are in close proximity for example as part of the same complex. They may be applied to detect a protein with high specificity, for example by detecting two different epitopes within the same polypeptide thereby only creating a signal when both epitopes are bound/available and in this way dramatically reducing or eliminating false positives and providing enhanced specificity.

The requirements for coincident binding are two ‘affinity probes’ which recognise two different sites or epitopes in the same target molecule, or in two target proteins in close proximity. This is achieved by providing a detection system or kit which can be understood as a bipartite biodetector based on two fusion proteins (chimeric recombinant proteins) which are referred to as a first fusion protein Reagent A (chimeric protein A) and a second fusion protein Reagent B (chimeric protein B) for convenience. The fusion proteins (recombinant proteins A and B) are each constructed as a combination of three modular domains expressed in frame, named recognition domain (or recognition module(s)), connector domain (or arm(s)) and detection domain (or detection module(s)), where each detection module comprises one half of a bipartite biodetector. The domains (modules) are described in more detail below.

Recognition Domain

The recognition domains (referred to as recognition module(s)) are the 'affinity probes' which recognise the target molecule/s or their post-translational modification/s. They can be any of multiple forms including: protein domains (e.g. SH2 domains) (Songyang, Z. et al. (1993). SH2 domains recognize specific phosphopeptide sequences. Cell, 72, 767-78), antibody recognition domains (Protein G or A or L) (e.g. Guss, B. et al. (1986). Structure of the IgG-binding regions of streptococcal protein G. EMBO J, 5, 1567-75), scFvs (single chain variable fragments), DARPins (Designed Ankyrin Repeat Proteins) (Zahnd, C. et al. (2006). Selection and characterization of Her2 binding-designed ankyrin repeat proteins. J Biol Chem, 281, 35167-75), Affibodies or similar moieties.

The target molecule may in principle be any biomolecular structure of interest to which the recognition domain may bind. This may in principle be nucleic acid, polypeptide, lipid, or chemical modifications of such molecules such as phosphate groups, methylation patterns, or other entities. Suitably the target molecule is a polypeptide or a post translational modification of a polypeptide; in these embodiments suitably the recognition domain is capable of recognising (binding to) polypeptide or a post translational modification of a polypeptide.

Protein Domains

Proteins are regulated by a vast and varying range of post-translational modifications many of which are recognized by modular protein-interacting domains that decode the state represented by the protein modifications; different domains recognise different post-translational modifications. In some embodiments we use these dedicated domains to 'read' (i.e. detect) the protein modifications by recognising the specific post-translational modifications of the protein of interest. In addition, there are also a vast number of protein domains which recognise and bind target proteins directly, and those can be employed for their simple ability to bind protein specifically. In a preferred embodiment the Src homology 2 (SH2) domain of Grb2 which is 114 amino acids in length (SEQ ID NO: 17) is used as a protein domain derived recognition domain of the invention. Grb2-SH2 specifically recognises the optimal peptide sequence motif pY-X-N-X, thus sequence specificity is driven by selecting a specific phosphotyrosine when the sequence contains an Asparagine (N) in position +2, and X represents any amino acid. There are three potential Grb2-SH2 binding sites on the Epidermal Growth Factor Receptor 1 (EGFR1) and the EGFR1 may thus be used to demonstrate or optimise the invention by western blot analysis of lysates and/or imaging fixed cells and tissues.

Protein G or A or L Ig Binding Domains

Protein G (SEQ ID NO:19) and protein A (SEQ ID NO:24) are well known to bind to most mammalian immunoglobulins, and in particular they bind the constant (Fc) region of polyclonal or monoclonal IgG. Similarly, protein L is well known to bind to most mammalian immunoglobulins, and in particular the light chains of polyclonal or monoclonal IgG. For our invention, protein A or G or L may be employed as the recognition domain to recognise a separate (i.e. not part of the fusion protein) antibody of choice which thus operates as an auxiliary part or augmentation of the recognition module. To demonstrate this application of the invention, the mouse monoclonal F4 anti-EGFR1 antibody may be used in combination with the Grb2-SH2 protein domain described above.

ScFvs (Single Chain Variable Fragments)

ScFvs may be isolated using a constructed phage display library, in which the scFvs are expressed as a fusion to the minor coat protein pill of the filamentous phage M13. ScFvs have the advantage of being small peptide sequences, and therefore easy to express as part of a fusion protein (e.g. the bipartite biodetector); in addition, they can be selected against a vast variety of small synthetic peptides, or synthetic modified peptides, providing a systematic approach for any selection requirements. The use of scFvs together with protein domain repertoires is a preferred application of the invention to multiplex assays, for example for use in monitoring multiple pathways at the same time in cancer patients or in any other given situation.

Polypeptide which Specifically Binds to a Target Polypeptide Sequence

The polypeptide may comprise an aptamer. An aptamer may refer to peptide molecule(s) that bind to a specific target molecule.

The polypeptide may be a polypeptide which specifically binds a backbone protein sequence. This may be a polypeptide which specifically binds to a protein epitope (unmodified; eg SH3 domain recognition of poly-proline sequences).

The polypeptide may comprise one or more polypeptide(s) which specifically bind to specific protein sequences (target protein sequences) and/or linear peptide epitopes. Examples of polypeptide(s) which specifically bind to specific protein sequences are described below in order to aid understanding, but are not intended to limit the invention only to those described.

SH3 Domains

Src homology 3 (SH3) domains are protein modules (55-70 amino acids) which recognise sequences bearing the core element PxxP (P=Proline, x=any amino acid—Proline-rich motif) flanked by other domain-specific residues. The surface of the SH3 domain has a hydrophobic ligand-binding surface which consists of three shallow pockets defined by conserved aromatic residues.

PTB domains

Some phosphotyrosine binding (PTB) domains are known to require phosphorylation for high affinity binding of peptide epitopes. However, other PTB domains exhibit similar or higher affinity for unphosphorylated peptides and selective phosphotyrosine binding appears to be restricted only to a relatively small subset.

PH domains

Pleckstrin homology (PH) domains do not have a single generic function. They are mostly known as modules that target membranes through recognition of phosphoinositide head groups, however, known ligands also include specific protein sequences.

LIM domains

LIM domains are composed of two contiguous zinc finger domains separated by two hydrophobic amino acids. The name is derived after their initial discovery in the proteins Lin-11, Isl-1 and Mec-3. Unlike the classical zinc fingers, these domains do not bind DNA but instead mediate specific interactions with other proteins.

WD40 Domains

The name WD40 is derived from the conserved WD dipeptide and the length of approximately 40 amino acids in each single repeat. Different WD40 domains have the ability to interact specifically with diverse proteins or peptides.

PDZ Domains

PDZ domains are ~90-residue repeats. PDZ is an acronym combining the first letters of three proteins—post synaptic density protein (PSD-95), *Drosophila* disc large tumor suppressor (DlgA), and zonula occludens-1 protein (zo-1)—which were first discovered to share the domain. PDZ domains are protein recognition modules which typically bind short specific sequences at the C-terminus end of their binding partners of the type S/TXV (X=any amino acid).

WW domains

WW domains are protein modules with two highly conserved Tryptophans (hence WW domain). They are small globular domains which are composed of ~40 amino acids organised in a triple-stranded β-sheet. Functionally they are similar to the SH3 domains in that they bind Proline-rich peptide motifs.

EVH 1 Domain

EVH1 (Enabled, VASP, Homology 1) domain is a protein interaction module that binds the Proline-rich consensus sequence (D/E)FPPPP.

EH Domains

Eps15 homology (EH) domains are protein modules (~100 amino acids) which recognise the tripeptide Asparagine-Proline-Phenylalanine (NPF in the single-letter code) as core binding site. Residues surrounding the NPF core motif influence biding specificity; carboxy-terminal NPFx or NPFxx (x=any amino acid) sequences have been found to have higher affinity for EH domains than internal sites.

Ankyrin Repeat Domains

Ankyrin repeats are structural motif consisting of 33 amino acids shaped into a β-hairpin-helix-loop-helix structure. They are structurally distinct from antibodies but share the ability to adapt structure thus a wide variety of target proteins can be bound.

Connector Domain

The connector domain (Arm(s)) are the spacers that connect the recognition modules to the detection modules. The connector domain may be considered a linker polypeptide.

In one embodiment the connector domain may be very short e.g. one or two amino acids. In one embodiment the connector domain may even be regarded as a single peptide bond for example if the recognition domain is directly fused to the detection domain.

When there is not a heterologous connector domain sequence inserted between the recognition domain and the detection domain, then the connector domain may be regarded as comprising the last amino acid of the recognition domain and the first amino acid of the detection domain (or vice versa e.g. comprising the last amino acid of the detection domain and the first amino acid of the recognition domain if in the other N/C orientation). Thus suitably the minimal connector domain comprises two amino acids. Thus in one embodiment the connector domain comprises two amino acids. Suitably these two amino acids may comprise one amino acid from the detection domain and one amino acid from the recognition domain. More suitably the two amino acids which represent the fusion junction between the recognition domain and the detection domain may together be regarded as a two-amino-acid connector domain. Suitably the connector domain comprises two amino acids; suitably said two amino acids comprise one amino acid of the recognition domain and one amino acid of the detection domain. Most suitably said two amino acids comprise the two amino acids of the fusion/junction between the recognition domain and the detection domain.

Connector domains longer than two amino acids offer advantages such as improving the performance of the detection and/or varying the distance between the two biomolecular structures which leads to a positive signal of coincidence detection. Thus suitably the connector domain is longer than two amino acids. For example, the connector domain may comprise 2 to 400 amino acids.

The connector domain may be up to 27 amino acids, such as a Gly-Ser linker (27aa=10 nm).

The connector domain may be up to 46 amino acids, such as a KEK/EKE linker (46aa=12 nm).

The connector domain may be up to 70 amino acids, such as a MyoVI linker (70aa=13 nm).

The connector domain may be up to 300 amino acids, giving a length of 40 nm-105 nm.

The connector domain may be up to 400 amino acids, giving a length of 54 nm-140 nm. In some embodiments the connector domain may be even longer; such connector domains should always be tested as described herein to ensure that problems from unsuitable large size connector domains (e.g. false positive detection) can be dealt with (for example by shortening the connector domain) if necessary.

It will be noted that the lengths are not always purely dependent on the number of amino acids, because the length depends in part on the three-dimensional structure of the polypeptide sequence and not purely on the number of amino acids.

An exemplary linker is a peptide comprising a flexible glycine/serine sequence of 10 amino acids. A most suitable example of this is given as SEQ ID NO:11.

An exemplary linker is a peptide obtained from the protein sequence of Myosin VI located in the Myosin VI tail. Myosin VI (MyoVI) is a class of Myosin that translocates along acting filaments as a vesicle transporter for a wide variety of processes such as cell migration, endocytosis and secretion. The full-length peptide structure contains a charged-repeat pattern of 66 amino acids in length (residues 915-980) (SEQ ID NO:14) that adopts a monomeric, stable and hydrophilic α-helical structure, thus resembling a relatively rigid connector. The size can vary based on the amino acid length chosen to span the distance between the binding sites of the two detection modules as part of the bipartite biodetector.

Two exemplary arm sizes are described but more can be created; a longer arm has the alpha-helical structure formed by 44 amino acids (~6 nm—residues 915-958) flanked at the N-terminus end with 3 Glycines and 1 Arginine (~1 nm) and at the C-terminus end with 2 Glycines and 3 Serines (~2 nm). A shorter arm contains the Glycine-Serine linker but no alpha-helix structure (~3 nm).

Both such exemplary arms contain an addition of 9 amino acids at the N-terminus end and 8 amino acids at the C-terminus end derived from the Gateway recombination sequences which add an extra ~6 nm to the length. Thus, the entire arm lengths are ~15 nm and ~9 nm long, respectively (FIGS. 5A and B). FIG. 5 also shows the overall distances when the recognition modules are included; the Protein G/Ab complex extends the arm a further ~9 nm and the Grb2 SH2 domain a further ~2 nm. All the distances specified are approximate.

To avoid any homodimeric states (e.g. homodimerisation of fusion protein(s) of the invention which might cause false positive read-outs) α-helices consisting of hydrophobic core repeats flanked on either side by charged residues (e.g. Glutamic acid) can be used as a connector domain (linker). This has the advantage of reducing or eliminating any possible homodimer formation due to electrostatic repulsion; when the helices attached to the DNA binding domain of the same species come into close proximity homodimer formation will be disrupted and only heterodimerisation will occur.

In addition, to avoid any homodimeric states, particular amino acids can be specifically mutated based on the structural evidence that the amino acids responsible for co-operative homodimerisation can be different to the ones involved in co-operative heterodimeric formation; thus, homo- and heterodimerisation can be functionally separated.

Detection Domain

The detection domains (or 'detection modules') are the nucleic acid binding parts of the fusion proteins of the invention. In other words, the detection domain is the amino acid sequence which forms the nucleic acid binding portion of the fusion protein.

In this document, for convenience, the words RXR and RAR usually refer solely to the DNA Binding Domain (DBDs) of the receptors and not to their full-length structure.

One form of the invention is based on the structure of nuclear receptors and their ability to form heterotrimers when binding to their cognate DNA sequences (the third molecule of the trimer—named hormone response elements, HREs) (Glass C. K. (1994). Differential Recognition of Target Genes by Nuclear Receptor Monomers, Dimers, and Heterodimers. Endocrine Reviews, 15(3): 391-407; Renaud J. P. and Moras D. (2000). Structural studies on nuclear receptors. Cell. Mol. Life. Sci., 57: 1748-1769. Rastinejad, F., T. et al. (1995). Structural determinants of nuclear receptor assembly on DNA direct repeats. Nature, 375, 203-11; Zechel, C. et al. (1994). Dimerization interfaces formed between the DNA binding domains determine the cooperative binding of RXR/RAR and RXR/TR heterodimers to DR5 and DR4 elements. EMBO J, 13, 1414-24). The invention exploits the fact that the DNA Binding Domains (DBDs) of nuclear receptors can generate the same pattern of DNA selectivity and dimerisation as the full-length receptors.

The nuclear receptor DBDs are highly conserved sequences comprising eight conserved cysteines which coordinate two Zn2+ ions, each Zn2+ is coordinated in a tetrahedral arrangement by four cysteines in a motif called a zinc finger. All nuclear receptor DBDs are formed of two zinc fingers where the third and fourth cysteine ligands are found at the N-terminus of an amphipathic helix. The two amphipathic helixes cross near their midpoints, almost perpendicular to each other, and are held together through the surrounding hydrophobic side chains. The first zinc finger interacts with the DNA major groove through the first helix, named recognition helix, and the second one is required for dimerisation and mutual orientation between the two sides of the dimer (FIG. 2).

In some embodiments of the invention, multiplexing of the coincidence detection is an important advantage of the invention. Multiplexing means the parallel analysis of more than one pair of coincident biomolecular structures. For example, multiplexing means analysis of more than one pair of coincident biomolecular structures in the same sample. This may be achieved in the context of the invention by varying the DBD of the fusion protein(s) and/or the sequence of the cognate specific nucleotide sequence element. This is explained in more detail below.

The DNA binding domain of nuclear receptors interacts with the DNA major groove through the α-helix of the first zinc finger (FIG. 2). This region is called the recognition helix, and contains three exposed residues responsible for discrimination between different half-site DNA response elements. Furthermore, the second zinc finger is involved in forming the dimerisation interface and it is important for the orientation of the heterodimer on its cognate response element. These features show that the DNA recognition and the heterodimer interactions are separated in the molecular structure and this allows substitution of the recognition helix with different α-helixes which discern dissimilar half-site sequences.

For example, the α-helix of RXR and RAR, which recognises the half-site AGGTCA, can be substituted with the helical segment of the glucocorticoid receptor (GR) (SEQ ID NO:7 and SEQ ID NO:8), which recognises the sequence AGAACA instead. Thus, utilising different nuclear receptor heterodimers in combination with different half-site sequences and spacer lengths of response elements (FIG. 1) it is possible to attain a wide repertoire of heterodimer pairs that will allow specific and unique binding of different DNA response elements at the same time which will be well suited for multiplexing.

In addition, other DNA binding domain pairs, with any structural motifs that can recognise specific DNA sequences, can be exploited for the same intent. For any type of DNA binding domain pair, the monomeric domains can be specifically mutated to reduce their binding affinity to their cognate DNA sequence as a monomer, so that only when both sides of the pair bind to its target DNA sequence the interaction becomes strong enough to hold the DNA into the complex as a trimer. Multiple reading (parallel reading/multiplexing) can then be achieved for example using different fluorophore probes as described above.

Some examples of DNA binding domains which can be utilised are shown below:

- RXR/TR using DR4 repeats and TR/VDR using DR3 repeats.
- Zinc finger domains of the Cys2His2 type. This class of zinc fingers differ from the structure of zinc fingers of nuclear receptors having two cysteines and two histidines forming the zinc finger instead of four cysteines. Each zinc finger module of this kind is able to recognise 3-4 base pairs of DNA specifically. Zinc fingers can be combined with predetermined DNA-binding affinity and specificity for specific DNA sequences. The dimerisation of separated Zif12 DNA binding domains upon association with a specific DNA sequence (i.e. trimerisation with the nucleic acid) has been monitored by FRET and highlighted for its potential use as a biosensor.
- Certain homodomain heterodimers, for example the *Saccharomyces cerevisiae* MATa1/MATa2 heterodimer. MATa1 and MATa2 on their own have only modest affinity for their sequence specific DNA but the MATa 1/MATa2 heterodimer binds DNA (i.e. trimerises) with high specificity and affinity.

These exemplary heterodimers/pairs are not an exhaustive list, but are intended to illustrate the range of detection domains (DNA binding domains) which may be applied in the invention.

Exemplary detection domains comprise the RXR or RAR DBDs which together form the bipartite biodetector as described above (FIGS. 3 and 4).

A suitable amino acid sequence comprising the RXR module is 96 amino acids long, between amino acids 129 and 224. (SEQ ID NOs 1, 7, 15, 20) A suitable amino acid sequence for RAR is also 96 amino acids, residues 82 to 177. (SEQ ID NOs 2, 8, 16, 21, 22)

In addition, the RXR and RAR modules may advantageously be specifically cloned to contain a protease site such as an HRV 3C Protease site-specific cleavage site at their N-termini to facilitate production of purified proteins virtually free of vector-encoded tag sequences (which in the examples section includes Glutathione S-Transferase, GST).

The design and selection of different zinc finger DNA BD heterodimers aims to produce a wide repertoire of heterodimer pairs that will allow binding to cognate DNAs with different and exclusive sequence specificity. Exclusive sequence specificity is a feature which advantageously facilitates multiplexing. This is demonstrated in the examples section.

The DNA binding domains (DBDs) can be derived from any suitable polypeptide provided they have the important property of binding nucleic acid in a co-operative manner i.e. that one of the DBDs alone should not show significant nucleic acid binding activity—it is important that nucleic acid binding only occurs when both polypeptides are in proximity (i.e. coincidence) and thereby form a heterotrimer with the nucleic acid to permit detection (readout).

Some examples of heterodimers which can be utilised as DBDs of detection modules are shown below:

1. RXR/TR (Thyroid hormone receptor) DNA BDs using DR4DNA sequence (Sequences 1, 3, 9a and 9b)
2. TR/VDR (Vitamin D3 receptor) DNA BDs using DR3DNA sequence (Sequences 3, 4, 9a and 9b)
3. MATa1 (Mating-type protein A1)/MATa2 (Mating-type protein α2) heterodimer Helix-Loop-Helix (HLH) homodomains (Sequences 5, 6, 9a and 9b)

The *Saccharomyces cerevisiae* MATa1 and MATα2 homeodomain proteins form a heterodimer that binds DNA with high affinity and specificity whereas the a1 and α2 proteins on their own have only modest affinity for DNA. The a1 and α2 homeodomains bind in a head-to-tail orientation with heterodimer contacts mediated by a sixteen residue tail located at the carboxyl terminal of the α2 homeodomain. This tail becomes ordered in the presence of a1 forming a short amphipathic helix; a pronounced sixty degree bend is induced in the DNA which allows protein-protein and protein-DNA contacts to form that could not take place in a straight DNA fragment. This complex formation may be a general feature of the architecture of other classes of eukaryotic transcriptional regulators (Li, T. et al. (1995). Crystal structure of the MATa1/MAT alpha 2 homeodomain heterodimer bound to DNA. Science, 270, 262-9) and these domains may be useful in the invention.

In addition, other DNA binding domain heterodimers, with structural motifs that can recognise specific DNA sequences other than the ones exemplified here, can be exploited for the same intent. For any type of heterodimer pair, the monomeric domains have to be specifically mutated when necessary (see examples—Protocol 2) to reduce their binding affinity to their cognate DNA sequence as monomers or the domains have to be selected for suitable affinity and/or specificity (see examples—Protocols 3-5); thus only when both sides of the heterodimer bind to its target DNA sequence the interaction becomes strong enough to hold the DNA into the complex.

The design and selection of different DNA BD heterodimers can provide a wide repertoire of heterodimer pairs that will allow specific and unique binding with different DNA specificity at the same time which are advantageously well suited for multiplexing.

Manufacture

Fusion proteins described herein may be made by any suitable means such as by synthetic means, in vitro translation, or recombinant nucleic acid expression in a suitable host cell. Protein recovery and/or purification can be by any suitable means known in the art, for example tagging with glutathione-S-transferase (GST) sequence; suitably such domains may be removed by cleavage after purification.

To clone in frame (i.e. to encode fusion proteins of) any given combination of recognition module—arm—detection module (or detection module—arm—recognition module), any suitable expression vector may be used such as the pGEX-4T-1 (GE Healthcare) expression vector. An exemplary vector may be the pGEX-4T-1 modified with the Gateway technology as described in the examples section. Expression and purification (together with removal of any tags used for example for purification if desired) can then be conducted according to standard techniques.

Vectors

Polynucleotides of the invention can be incorporated into a recombinant replicable vector. The vector may be used to replicate the nucleic acid in a compatible host cell. Thus in a further embodiment, the invention provides a method of making polynucleotides of the invention by introducing a polynucleotide of the invention into a replicable vector, introducing the vector into a compatible host cell, and growing the host cell under conditions which bring about replication of the vector. The vector may be recovered from the host cell. Suitable host cells include bacteria such as *E. coli*, yeast, mammalian cell lines and other eukaryotic cell lines, for example insect Sf9 cells.

Preferably, a polynucleotide of the invention in a vector is operably linked to a control sequence that is capable of providing for the expression of the coding sequence by the host cell, i.e. the vector is an expression vector. The term "operably linked" means that the components described are in a relationship permitting them to function in their intended manner. A regulatory sequence "operably linked" to a coding sequence is ligated in such a way that expression of the coding sequence is achieved under condition compatible with the control sequences.

The control sequences may be modified, for example by the addition of further transcriptional regulatory elements to make the level of transcription directed by the control sequences more responsive to transcriptional modulators.

Vectors of the invention may be transformed or transfected into a suitable host cell as described below to provide for expression of a protein of the invention. This process may comprise culturing a host cell transformed with an expression vector as described above under conditions to provide for expression by the vector of a coding sequence encoding the protein, and optionally recovering the expressed protein.

The vectors may be for example, plasmid or virus vectors provided with an origin of replication, optionally a promoter for the expression of the said polynucleotide and optionally a regulator of the promoter. The vectors may contain one or more selectable marker genes, for example an ampicillin resistance gene in the case of a bacterial plasmid or a neomycin resistance gene for a mammalian vector. Vectors may be used, for example, to transfect or transform a host cell.

Control sequences operably linked to sequences encoding the protein of the invention include promoters/enhancers and other expression regulation signals. These control sequences may be selected to be compatible with the host cell for which the expression vector is designed to be used in. The term promoter is well-known in the art and encompasses nucleic acid regions ranging in size and complexity from minimal promoters to promoters including upstream elements and enhancers.

The promoter is typically selected from promoters which are functional in mammalian, cells, although prokaryotic promoters and promoters functional in other eukaryotic cells may be used. The promoter is typically derived from promoter sequences of viral or eukaryotic genes. For example, it may be a promoter derived from the genome of a cell in which expression is to occur. With respect to eukaryotic promoters, they may be promoters that function in a ubiquitous manner (such as promoters of α-actin, b-actin, tubulin) or, alternatively, a tissue-specific manner (such as promoters of the genes for pyruvate kinase). They may also be promoters that respond to specific stimuli, for example promoters that bind steroid hormone receptors. Viral promoters may also be used, for example the Moloney murine leukaemia virus long terminal repeat (MMLV LTR) promoter, the rous sarcoma virus (RSV) LTR promoter or the human cytomegalovirus (CMV) IE promoter.

It may also be advantageous for the promoters to be inducible so that the levels of expression of the heterologous gene can be regulated during the life-time of the cell. Inducible means that the levels of expression obtained using the promoter can be regulated.

In addition, any of these promoters may be modified by the addition of further regulatory sequences, for example enhancer sequences. Chimeric promoters may also be used comprising sequence elements from two or more different promoters described above.

Host Cells

Vectors and polynucleotides of the invention may be introduced into host cells for the purpose of replicating the vectors/polynucleotides and/or expressing the proteins of the invention encoded by the polynucleotides of the invention. Although the proteins of the invention may be easily produced using prokaryotic cells as host cells, it may be desired to use eukaryotic cells, for example yeast, insect or mammalian cells, in particular mammalian cells.

Vectors/polynucleotides of the invention may introduced into suitable host cells using a variety of techniques known in the art, such as transfection, transformation and electroporation. Where vectors/polynucleotides of the invention are to be administered to animals, several techniques are known in the art, for example infection with recombinant viral vectors such as retroviruses, herpes simplex viruses and adenoviruses, direct injection of nucleic acids and biolistic transformation.

Protein Expression and Purification

Host cells comprising polynucleotides of the invention may be used to express proteins of the invention. Host cells may be cultured under suitable conditions which allow expression of the proteins of the invention. Expression of the proteins of the invention may be constitutive such that they are continually produced, or inducible, requiring a stimulus to initiate expression. In the case of inducible expression, protein production can be initiated when required by, for example, addition of an inducer substance to the culture medium, for example dexamethasone or IPTG.

Proteins of the invention can be extracted from host cells by a variety of techniques known in the art, including enzymatic, chemical and/or osmotic lysis and physical disruption.

Orientation

It will be apparent that the fusion proteins of the invention may be made in either orientation with regard to their N- and C-termini. For example one orientation is N-recognition domain-connector domain-detection domain-C. For example another orientation is N-detection domain-connector domain-recognition domain-C. It will be apparent that the connector domain is always between the recognition domain and the detection domain. However, in principle either orientation may be employed. Suitably the orientation is N-recognition domain-connector domain-detection domain-C.

Cognate Specific Nucleotide Sequence

The cognate specific nucleotide sequence refers to the oligonucleotide binding site(s) and may further include any flanking sequences required for binding.

The nucleic acid comprising the cognate specific nucleotide sequence may have further nucleotide sequence(s) other than the minimal sequence necessary for recognition/binding. For example, the two flanking regions of the consensus sequence can be any DNA sequence of choice and length.

Thus, for the example of the fusion proteins comprising RXR and RAR and the cognate specific nucleotide sequence comprising DR5, when DR5 is part of the RXR-RAR complex, the two flanking regions of the consensus sequence can be any DNA sequence of choice and length, and it can be single or double stranded DNA; established technology will then allow the detection of specific nucleic acid sequences.

In multiplex embodiments of the invention, it is clearly important that one or more of the flanking regions is of different sequence for each of the pairs of fusion proteins used so that the readout/visualisation can distinguish between the different pairs (i.e. different detectors) used and therefore the information can be extracted and kept separate for the different questions/readouts being undertaken in a single multiplex analysis.

Detection of specific nucleic acid sequences, for example with oligonucleotide probes, polymerase reactions or PCR techniques, have the enormous advantage of offering excellent specificity, sensitivity and the potential to be multiplexed. For example, each DR5 3' end flanking region can be single stranded, and can be used to act as a primer for a Rolling Circle Amplification (RCA) reaction using single stranded circular DNA as templates (inside the single circle are sequences complementary to fluorescent probes); thus a repeated sequence is generated and standard fluorescently labelled oligonucleotides will hybridise to the RCA product giving a bright intense spot. RCA is a well established technology.

Another technology to attain bright intense spots for detection is the use of Quantum dot (Qdot) nanocrystals, such as when conjugated to oligonucleotides or proteins. Qdots are nanoscale atom clusters comprising a core made of several atoms (from hundreds to thousands of atoms) of a semiconductor material (often cadmium mixed with selenium or tellurium), a shell (usually zinc sulphide) which stabilises the core, and a coating surface to render the Qdots hydrophilic for biological applications. They are superior to traditional organic dyes for their brightness, which is many times higher than traditional organic fluorophores, as well as for their long-term photo-stability; cells and tissues labelled with Qdot nanocrystals can be stored permanently and re-analysed several times with the same level of sensitivity. The drawback of this application is the diameter of the particles being between 10-20 nm, roughly the size of a protein. However, the use of Qdots for highly sensitive cellular imaging has proved to be successful and showed major advances over the past decade. Moreover, the improved photo-stability of Qdots allows the acquisition of many consecutive focal-plane images that can be reconstructed into a high-resolution three-dimensional image.

In addition, besides the above techniques, there is the standard use of organic fluorescent dyes and enzymes (e.g. HRP) conjugated to proteins, antibodies and oligonucleotides. To date, exemplar studies on the biodetector using ELISA assays and western blots were achieved using 5'-biotinylated oligos in combination with a streptavidin-HRP conjugated protein; implementation of the biodetector may employ biotin/streptavidin-HRP for completion of ELISA assays and western blot analysis. In fixed cells and tissues Qdot streptavidin conjugates can be exploited in the first instance and substituted subsequently for multicolour analysis with standard fluorophore conjugated oligonucleotide probes in combination with RCA reactions using different single stranded circular DNA.

Multicolour analysis could be carried out also using Qdot nanocrystals conjugated to oligonucleotides, or Qdots/standard fluorophores conjugated to zinc fingers are another option, where zinc fingers will recognise unique DNA sequences flanking the cognate specific nucleotide sequence (e.g. the DR5 response element).

Quantification may be carried out using any suitable technique which can be applied to the selected mode of detection. This may be manual or automated using appropriate image analysis software.

Exemplary detection techniques are described below. These are described for ease of understanding using DR5 as an example. The techniques apply EQUALLY to other cognate nucleic acid sequences and should be interpreted accordingly. This section is not intended to limit the invention to the specific reagents/sequences discussed but is presented as an illustration to aid understanding of how the detection may be accomplished.

A—Detection by Rolling Circle Amplification (RCA)

Dilute the ss/ds PrA-DR5 (Sequence 9a, 100 pmol/μl) 1:1,000 in 0.8× sodium citrate buffer (0.8×SSC: 120 mM NaCl, 12 mM sodium citrate) containing 0.1% Tween 20 (0.8×SSC/Tw) with additionally 1% BSA, 10 pmol/μl Poly(dT). Wash the coverslips 3×1 min in 0.8×SSC/Tw, immediately add the ss/ds PrA-DR5 reagent to the samples and incubate for 1 h at RT. Next, dilute the ss circular DNA (2.5 pmol/μl) 1:125 in 0.8×SSC/Tw, 1% BSA, 10 pmol/μl Poly(dT). Wash the coverslips 3×1 min in 0.8×SSC/Tw and immediately add the ss circular DNA solution. Incubate for 1 h at RT. Prior to RCA wash the coverslips 3×1 min in 0.8×SSC/Tw and rinse once in Phi29 DNA polymerase buffer (50 mM Tris HCl, 10 mM $MgCl_2$, 10 mM $(NH_4)_2SO_4$, pH 7.5). Prepare the RCA solution with 1 unit Phi29 DNA polymerase, 4 mM DTT, 1 mM dNTPs, 0.02% BSA in Phi29 DNA polymerase buffer. Add the Phi29 polymerase only immediately before addition to the sample. Add the amplification solution to the samples and incubate the coverslips for 90 min at 37° C. After three additional washing steps×1 min in 0.8×SSC/Tw add 2 pmol/μl fluorescence-labelled probe to hybridise for 30 min at 37° C. to the single-stranded RCA product in 0.8×SSC/Tw containing 1% BSA, 10 pmol/μl Poly(dT). Wash samples 3×1 min in 0.8×SSC/Tw, rinse once with water and mount the coverslips using an aqueous mounting medium ensuring no air bubbles get trapped under the coverslip. Nail polish can be used to seal the edges.

Alternatively, Horse Radish Peroxidise (HRP)-labelled probes can be used instead of fluorescence-labelled probes. The HRP enzyme in the presence of substrate (e.g. NovaRED, Vector Laboratories) produces a red reaction product in a brightfield microscope. After incubation with a peroxidase (HRP) detection system, rinse well. Incubate samples with the substrate working solution at room temperature until suitable staining develops. Development times should be determined by the investigator but generally 2-15 minutes provides good staining intensity. Wash samples 5 min in water and mount the coverslips as described above.

B—Detection by Direct Hybridisation Using a Fluorescence-Labelled Probe

Dilute the ss/ds PrA-DR5 (Sequence 9a, 100 pmol/μl) 1:1,000 in 0.8× sodium citrate buffer (0.8×SSC: 120 mM NaCl, 12 mM sodium citrate) containing 0.1% Tween 20 (0.8×SSC/Tw) with additionally 1% BSA, 10 pmol/μl Poly(dT). Wash the coverslips 3×1 min in 0.8×SSC/Tw, immediately add the ss/ds PrA-DR5 reagent to the samples and incubate for 1 h at RT. Next, dilute the fluorescence-labelled DNA probe (100 pmol/μl) 1:500 in 0.8×SSC/Tw, containing 1% BSA, 10 pmol/μl Poly(dT). Wash the coverslips 3×1 min in 0.8×SSC/Tw and immediately add the fluorescence-labelled probe to hybridise directly to the ss/ds PrA-DR5 (Sequence 9a) and incubate for 1 h at RT. Wash samples 3×1 min in 0.8×SSC/Tw, rinse once with water and mount the coverslips as described above.

Collect images using a fluorescence microscope equipped with i) excitation/emission filters compatible with fluorophore/s and nuclear or cytoplasmic stain excitation/emission; ii) software for image acquisition. At least 20× magnification should be used.

C—Detection by Quantum Dot (Qdot) Nanocrystals

This protocol uses streptavidin quantum dots, which contain streptavidin covalently attached to quantum dot nanocrystals for binding biotinylated probes (typically 5-10 streptavidins/Qdot conjugate) (Invitrogen).

Dilute the biotinylated-ds PrA-DR5 (Sequence 9a, 100 pmol/μl) 1:1,000 in 0.8× sodium citrate buffer (0.8×SSC: 120 mM NaCl, 12 mM sodium citrate) containing 0.1% Tween 20 (0.8×SSC/Tw) with additionally 1% BSA, 10 pmol/μl Poly (dT). Wash the coverslips 3×1 min in 0.8×SSC/Tw, immediately add the biotinylated-ds PrA-DR5 reagent to the samples and incubate for 1 h at RT. Next, dilute the Streptavidin conjugated Qdots by adding 2 μl of the stock (1 μM) into 100 μl of 0.8×SSC/Tw, 1% BSA, 10 pmol/μl Poly(dT) prior to use to obtain the Qdot streptavidin conjugate concentration of 20 nM (it is preferable to use between 10 nM and 40 nM Qdot streptavidin conjugate final concentration). Use the diluted Qdot streptavidin conjugate immediately. Incubate the samples for 1 h at RT. Wash samples 3×1 min in 0.8×SSC/Tw, rinse once with water and mount the coverslips in Qmount Qdot mounting media (Invitrogen) to preserve the fluorescence signal of Qdot nanocrystals.

It is possible to visualise single Qdot nanocrystals under a fluorescence microscope equipped with excitation/emission filters optimised for the excitation and emission of the Qdot conjugates in use. Single Qdot nanocrystals can be visualised at 60× magnification. Single crystal blinking can be detected by eye. A list of filter recommendations for Qdot nanocrystals can be found at www.omeqafilters.com or www.chroma.com.

Alternatively, Qdot nanocrystals can be cross linked to DNA probes (Qdot Oligo Conjugation Kit, Quantum Dot Corporation, www.qdots.com) to capture the DNA targets, for example, to capture the ss/ds PrA-DR5 reagent (Sequence 9a). Oligo-conjugated Qdot nanocrystal probe are very well suited for multicolour analysis when using different single stranded conjugated oligonucleotides.

D—Detection by Total Internal Reflection Fluorescence (TIRF)

TIRF employs the phenomenon of total internal reflection, which occurs at the interface between optically dense medium, such as glass, and optically less dense aqueous solution. At particular angles of incidence the excitation beam, although fully reflected, generates at the interface with water an evanescent field, which extends beyond the interface and into the aqueous solution. Only molecules that are at the TIRF surface will fluoresce while fluorophores at the distances larger than 100-200 nm are not excited and, respectively, do not fluoresce. Thus, TIRF efficiently rejects background signal from the bulk of the solution and therefore detection of nucleic acids bound to a target at the interface can be carried out without removing unbound material.

The protocol for performing TIRF microscopy can be set up as for standard experiments, as described above on coverslips, with the only exception that the final washing steps can be omitted for example when the invention is worked in an embodiment in which unbound nucleic acid is not removed before detection. Mounting media ideally should have an aqueous-like refractive index.

E—Detection by Forster Resonance Energy Transfer imaging (FRET)

FRET is a detection technique which involves the transfer of energy from an excited donor fluorophore to an acceptor fluorophore which has an excitation spectrum that overlaps with the donor emission spectrum and is ≤9 nm away. Based on this principle, the detection protocol involves the use of a ss/ds PrA-DR5—Cy3 as a donor (Sequence 30) in combination with a FITC-PrA as an acceptor (Sequence 30).

In the circumstances where the FITC-PrA anneals to the ss/ds PrA-DR5—Cy3 donor, the donor and the acceptor fluorophores will be close enough to generate a FRET signal. This can be followed in various ways, but is best detected by monitoring the changing lifetime of the acceptor flouorophore. These techniques are well established and microscopy platforms are available commercially. The protocol to generate a FRET signal is as described in section B with the exception that the ss/ds PrA-DR5 is fluorescently-labelled (ss/ds PrA-DR5-Cy3); moreover it will be noted that the final washing steps can be omitted for example when the invention is worked in an embodiment in which unbound nucleic acid is not removed before detection.

F—Detection by Fluorescence Polarisation (FP)

Fluorescence polarisation spectroscopy refers to a technique that allows the detection of the change in polarisation properties of a substance associated with its changing rotation. A fluorescent DNA probe tumbling free in solution will have a distinct polarisation property compared to when bound to an immobilised protein or complex. The detection of polarised emissions from a fluorophore attached to DR5 or of a fluorescent DNA-probe binding to DR5 in the context of DR5 capture as outline in "B" provides a method for the measurement of bound DR5 and hence coincidence detection in the context of free DR5 or of the free DNA-probe. It will of course be noted that the final washing steps can be omitted for example when the invention is worked in an embodiment in which unbound nucleic acid is not removed before detection.

G—Detection by Scintillation Proximity Technology

The detection of bound DR5 by scintillation proximity for example employing FlashPlate® is another homogeneous format in which DR5 can be monitored. The protocol for this is essentially identical to that specified in B (except that the final washing steps can be omitted for example when the invention is worked in an embodiment in which unbound nucleic acid is not removed before detection) excepting the use of radiochemically modified DR5 (eg $^{32}$P-phosphate labeled) and appropriate vessels for the incubations and detection (mutliwell FlashPlate® would be a preferred format).

Advantages

The fusion proteins and kits of the invention are cheap to manufacture, simpler to use, of higher information content, more efficient and versatile than prior art materials.

The invention can be used to detect diverse protein pathways involved in cancer and other diseases or as a simple research tool to investigate cellular events/protein interactions.

The materials of the invention are cheap to manufacture. The invention is very easy to implement in standard and routine laboratory procedures.

Analysis can be multiplexed and therefore it is a very powerful new tool.

The total amount of target protein is easier to detect and quantify versus the one containing the post-translational modification. In prior art such as duolink it is not possible to detect or quantify the total amount of target protein.

No conjugation process is required in the invention, whereas duolink requires conjugation of antibodies to oligonucleotides, which can be problematic.

The invention advantageously eliminates covalent linkage (s) and ligation step(s) which are technically challenging and essential to the known duolink techniques.

The invention permits the use of a wide range of protein domains that recognise specific post-translational modifications or domains of the target protein as recognition domains. By contrast the duolink method uses solely primary antibodies that must be of two different species, which can be a restrictive drawback.

Preformed Complex Embodiment

In one embodiment it is possible to add the two fusion proteins and the nucleic acid in a single step. In other words the trimeric complex may be preformed and added. In this context steps (ii) to (v) (i.e. the steps of Contacting the sample with fusion protein/s (ii)/incubating (iii)/contacting the sample with nucleic acid) may be combined into a single step, and removing unbound fusion/s (iv)/may be omitted.

In this embodiment the invention provides a method of detecting the coincidence of two biomolecular structures in a solid phase sample, said method comprising (i) providing a first and a second fusion protein, each fusion protein comprising (a) a detection domain, said detection domain comprising a DNA binding domain; said detection domain capable of binding a cognate specific nucleotide sequence in co-operation with a further detection domain;

(b) a recognition domain, said recognition domain capable of binding a target biomolecular structure; and (c) a connector domain; said connector domain being fused at one end to the detection domain and being fused at the other end to the recognition domain;

wherein at least two of (a), (b) and (c) are heterologous to one another;

wherein the recognition domains of said first and said second fusion proteins are capable of binding to first and second biomolecular structures;

(ii) contacting the sample with said first and second fusion proteins and incubating to allow binding and contacting the sample with nucleic acid comprising said cognate specific nucleotide sequence;

(iii) incubating to allow heterotrimeric binding of the nucleic acid (iv) detecting nucleic acid bound to the sample wherein detection of nucleic acid in step (iv) indicates that the two biomolecular structures are present coincidentally in said sample.

It is possible that this embodiment offers a greater sensitivity when the binding of the recognition domain(s) to their target(s) is weak.

It is possible that this embodiment carries a greater risk of false positive signal; care must be taken in interpreting the results of this embodiment.

Suitably in this embodiment the oligonucleotide sequence is DR5.

Oligonucleotide Capture for Biological Readout

Oligonucleotide capture may be used for readout sensitisation. An alternative and simple use of DNA BD biodetectors is to enhance readout sensitivity in fixed cells/tissue samples and/or in western blot analysis. Low abundance proteins are difficult targets to detect when using standard antibody procedures. Using this novel approach low abundance proteins can be easily recognised and visualised.

For example, recognition domains such as phospho-specific SH2 domains/DARPins/scFvs can be expressed in frame with a DNA BD which is able to bind in a specific manner to a DNA sequence without the necessity of coincidence DNA recognition. Any antibody of choice can also be recognised through a Protein G (or protein A or protein L)-DNA BD fusion detector reagent.

For oligonucleotide capture embodiments e.g. for biological readout, in principle suitable recognition and/or detection domains may be selected from those described above in connection with coincidence detection. Recognition domains can be of any species such as SH2 domains, ProteinA/G/L, scFv, antibody variable heavy or light chains, polypeptides which specifically bind a post translationally modified amino acid residue or a backbone protein sequence. For the DNA binding domain, any DNA BD able to recognise specifically a DNA sequence without the necessity of coincidence DNA recognition can be employed.

Alternate fusion proteins having different recognition/detection domains may be used in multiplexing with different reagents and different sequence-specific DBs.

In some embodiments suitably the recognition domain does not comprise scFv.

Suitably the recognition domain may comprise, or may be, an SH2 domain.

For oligonucleotide capturing, any DNA BD able to recognise specifically a DNA sequence can be employed. The cognate DNA sequence will contain a suitable flanking region that can be specifically amplified for example using rolling circle amplification reaction (RCA). The amplified DNA can be visualised with fluorescently (or other) labelled oligonucleotide probes as previously described.

This approach will allow a very sensitive readout (down to single molecules) allowing the study of those molecules which are otherwise very difficult to be distinguished and visualised with standard techniques. This is discussed in more detail in Example 7 and FIG. 14.

Well suited DNA BDs that can be used for this purpose are the zinc finger domains of the Cys2His2 type. This class of zinc fingers differ from the structure of zinc fingers of nuclear receptors in having two cysteines and two histidines forming the zinc finger instead of four cysteines. An example is the zinc finger DNA BD of Zif268 (Sequence 23) which contains three zinc finger domains that bind the major groove in a simple tandem arrangement. Each finger is able to recognise 3-4 base pairs of DNA specifically; the α-helix (recognition helix) fits into the major groove and residues at key positions in each of the α-helices of Zif268 make specific DNA base contacts. The three zinc fingers of Zif268, in addition to several other domains of the same class, provide an attractive framework from which to choose, design and select novel DNA binding proteins with different DNA specificities to be utilised for multiplexing purposes.

It will be apparent that the connector domain need not be used in this embodiment i.e. the DNA BD and the recognition domain may be directly fused in this embodiment. If steric problems are encountered then a connector domain may be included between the DNA BD and the recognition domain.

Thus in another aspect the invention relates to a fusion protein, said fusion protein comprising:

i) a detection domain, said detection domain comprising a DNA binding domain; said detection domain capable of binding a cognate specific nucleotide sequence;

ii) a recognition domain, said recognition domain capable of binding a target biological molecule;

the detection domain and the recognition domain being fused; wherein (i) and (ii) are heterologous to one another.

Suitably said recognition domain is capable of binding a phosphopeptide molecule.

Suitably said recognition domain comprises protein G or protein A or protein L, most suitably protein G or A, most suitably protein G.

Suitably the DNA binding domain comprises a Cys2His2 type zinc finger, suitably the DNA binding domain of Zif268 (SEQ ID NO:23).

In a preferred embodiment the recognition domain is Protein G and the detection domain is Zif268.

The principle of oligonucleotide capture for biological readout is to detect the target by applying a fusion protein of the invention and a nucleic acid. If the target is present (and available for binding by the fusion protein) then the nucleic acid will be localised to the target. The nucleic acid can then be detected. The mode of detection of the nucleic acid can be chosen to provide amplification of the signal e.g. by rolling circle amplification or other modes of nucleic acid detection/readout as described above in connection with coincidence detection.

Thus the invention relates to a method of detection a target in a sample, the method comprising (i) contacting the sample with a fusion protein as described above (ii) contacting the sample with a cognate nucleic acid capable of being bound by the fusion protein of (i); and (iii) detecting bound nucleic acid and inferring presence of the target in the sample.

In another embodiment the fusion protein may be added and any excess/unbound fusion protein washed away before adding nucleic acid. This has the advantage of reducing background and/or improving signal to noise ratio. In this embodiment the method described above suitably comprises step (ia) removing unbound fusion protein.

In another embodiment the nucleic acid may be added and any excess/unbound nucleic acid washed away before detection. This has the advantage of reducing background and/or improving signal to noise ratio. In this embodiment the method described above suitably comprises step (iia) removing unbound nucleic acid.

In one embodiment, the nucleic acid may be added with the fusion protein. The nucleic acid and fusion protein may be premixed or preincubated, or may simply be added at the sequentially or simultaneously. This advantageously reduces the number of steps in detection and simplifies the method. In this embodiment the method described above is suitably conducted by combining steps (i) and (ii) into a step of contacting the sample with a fusion protein as described above and with a cognate nucleic acid capable of being bound by the fusion protein.

In another aspect, the invention relates to a kit comprising (a) a fusion protein as described above; and (b) a nucleic acid comprising a cognate specific nucleotide sequence as described above;

wherein binding of the detection domain to the specific nucleotide sequence is by formation of dimer. (I.e. one fusion protein and one nucleic acid molecule; multiple fusion protein molecules are not required in this embodiment since binding is not required to be co-operative in this embodiment.)

BRIEF DESCRIPTION OF THE DRAWINCIS

FIG. 1 shows DR hormone response elements with varying length spacers. HRE-DR5 (SEQ ID NO. 73); HRE-DR4 (SEQ ID NO. 74); HRE-DR3 (SEQ ID NO. 75); HRE-DR2 (SEQ ID NO. 76); and HRE-DR1 (SEQ ID NO. 77).

FIG. 2 shows the dimeric structure of the nuclear receptor DBDs, in association with HRE-DR5 (SEQ ID NO. 73) shown as a double-stranded molecule.

FIG. 3 shows a schematic representation of the RXR-RAR DBDs in heterotrimeric complex with the retinoic acid response element DR5, HRE-DR5 (SEQ ID NO. 73) shown as a double-stranded molecule.

FIGS. 4A-C show a schematic view of the invention.

Figure 4:
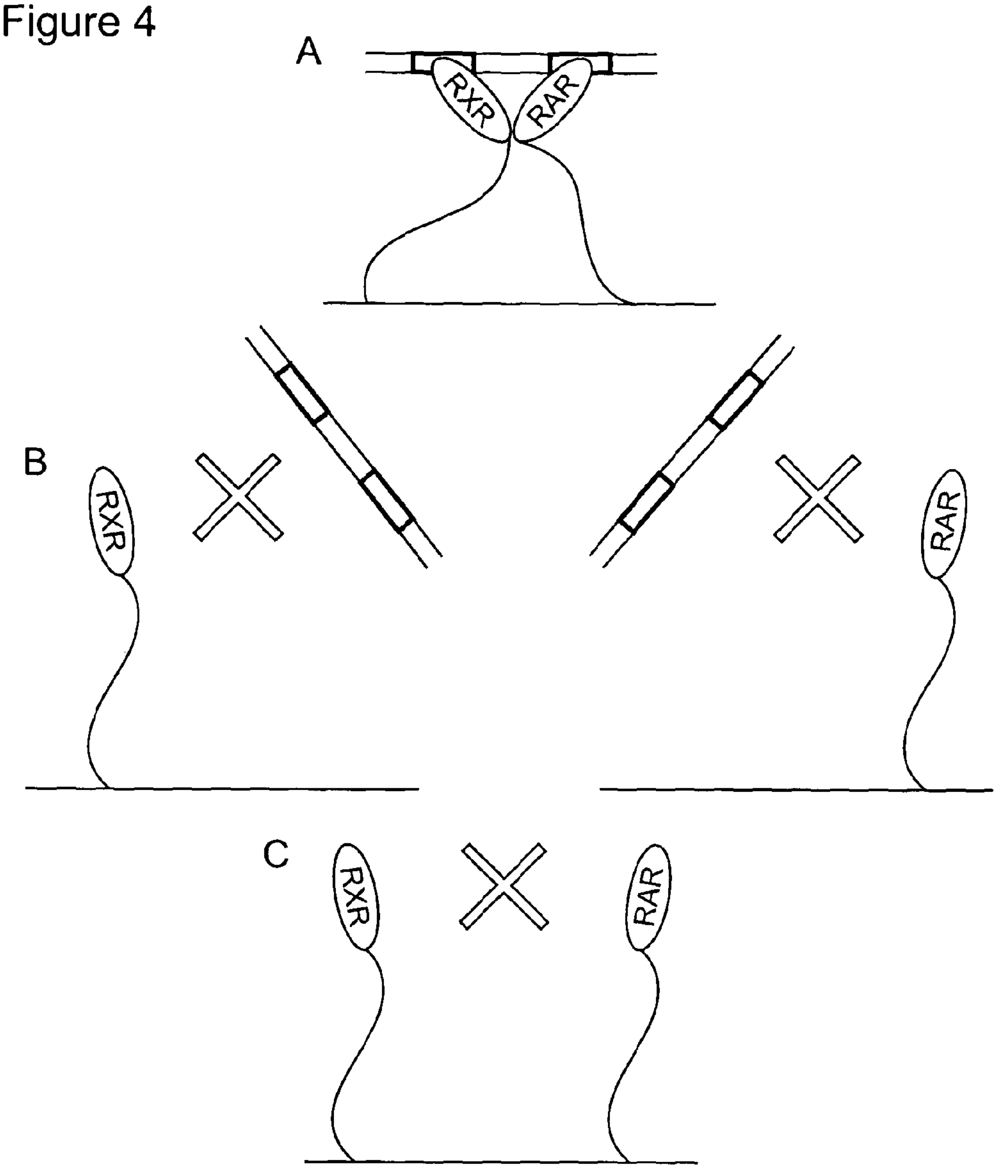
Figure 4D:
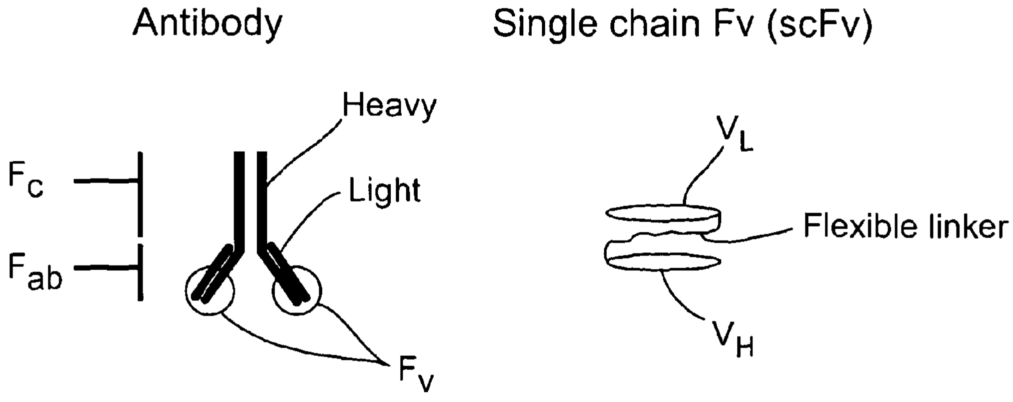

FIG. 4D shows diagrams of antibody and scFv structures.

FIGS. 5A-B show a schematic representation of the arm lengths that connect the recognition modules to the detection modules.

Figure 6:
Figure 6:
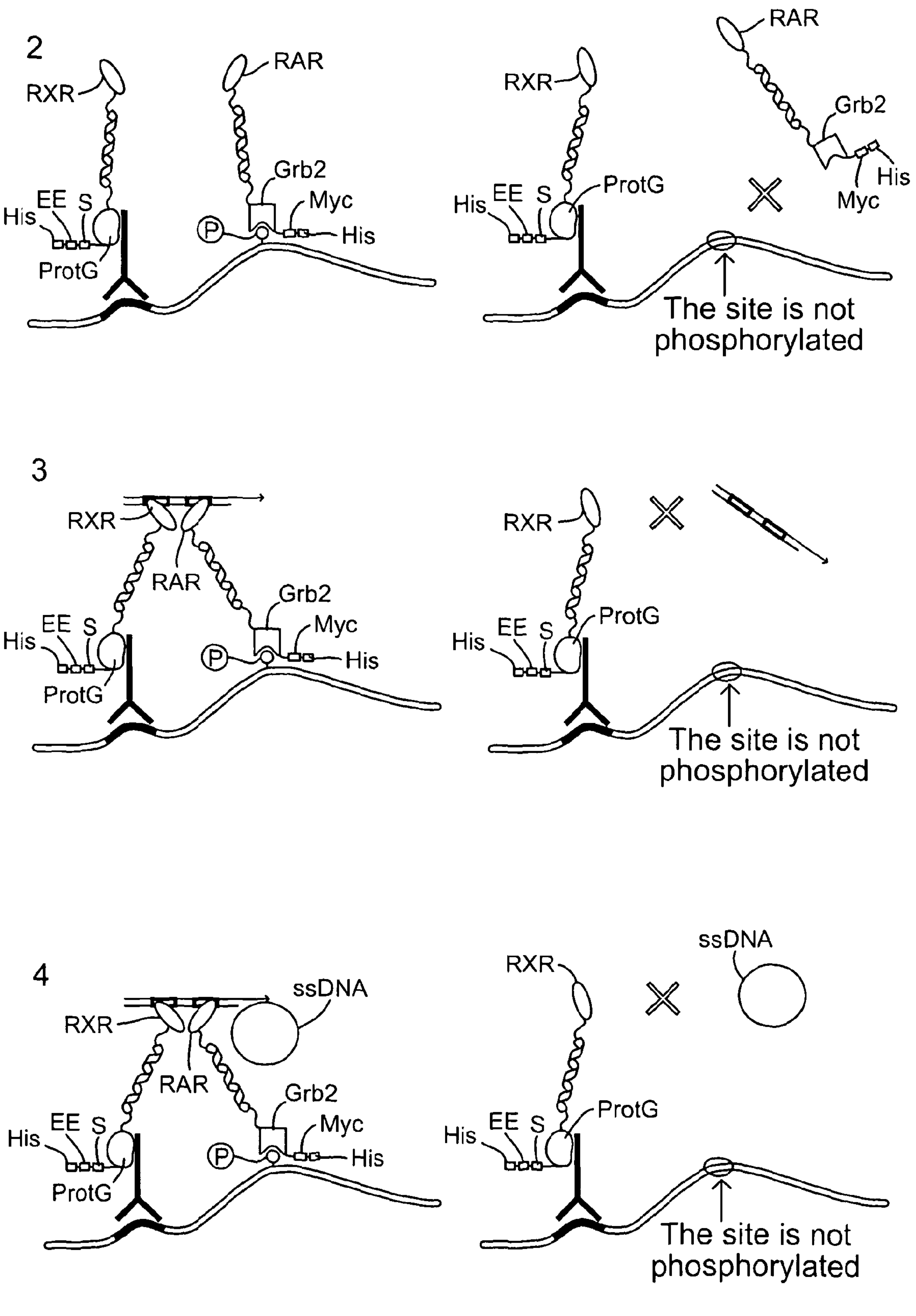
Figure 6:
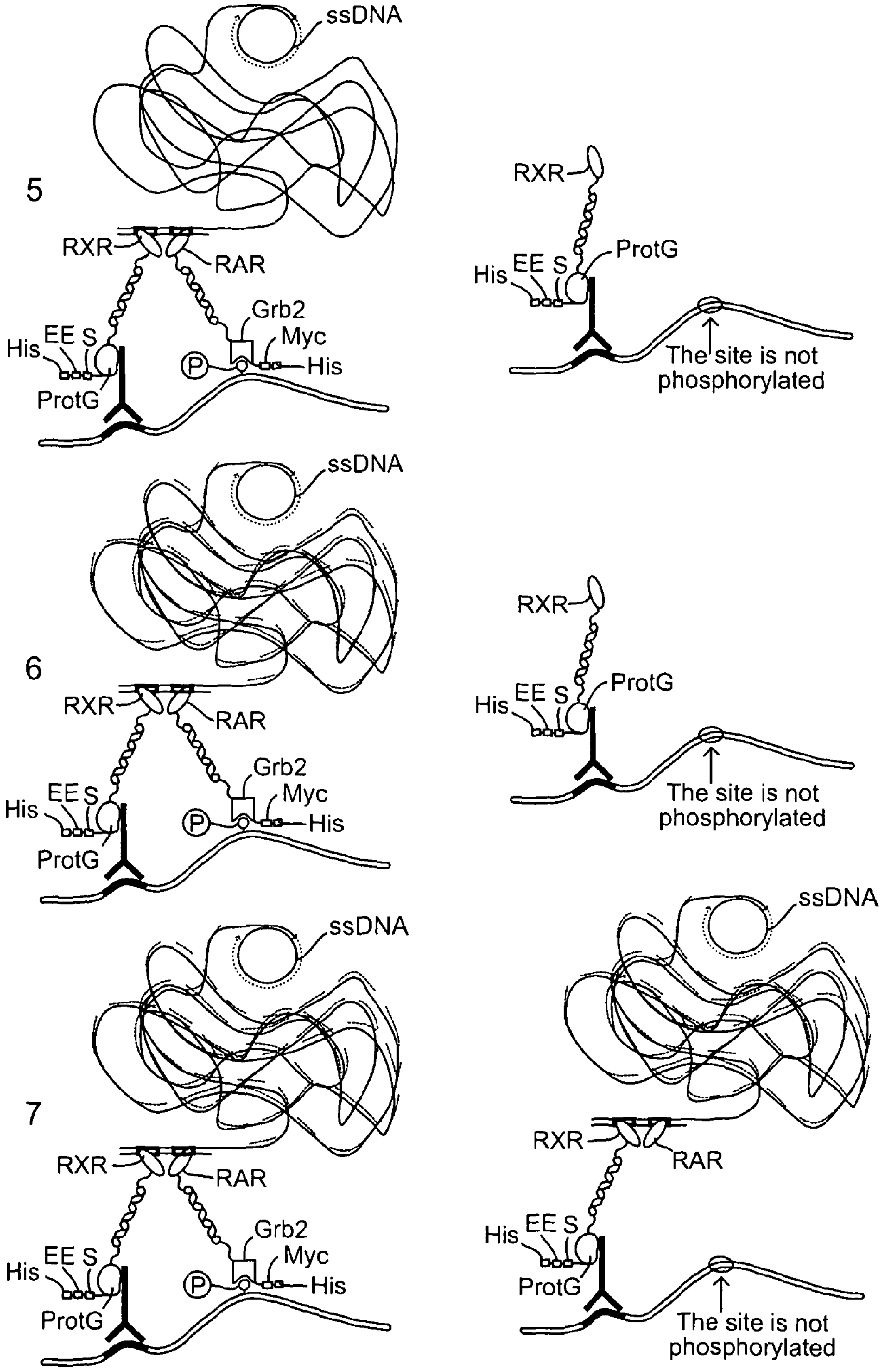

FIG. 6 shows diagrams illustrating the invention.

The principle of the biodetector described in steps 1 to 7; starting materials are membrane-bound denatured proteins from cell lysates or fixed cells or tissues on microscope slides. The principle is described using the example of the Grb2SH2 domain and the Protein G Ig binding domain binding α-EGFR 1. The Grb2SH2 domain and the Protein G/α-EGFR1 are the pair of detectors that may be used as explained herein and can be regarded as proof of principle by western blot analysis of lysates and imaging fixed cells and tissues. A pair of fully recombinant detectors may have ScFv instead of the Protein G and in this case step 1 is omitted.

Figure 7:
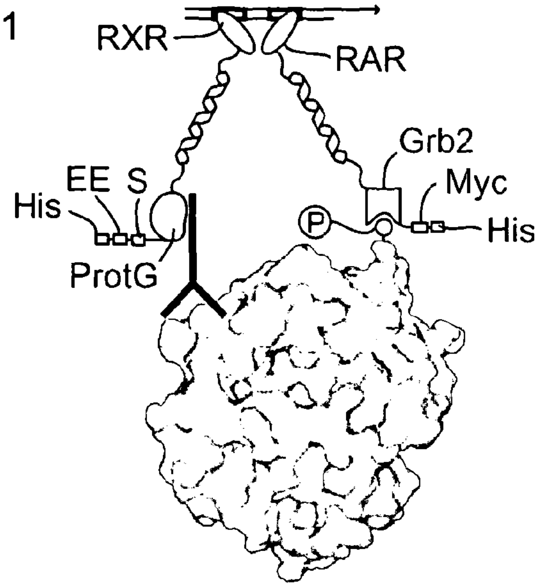
Figure 8:
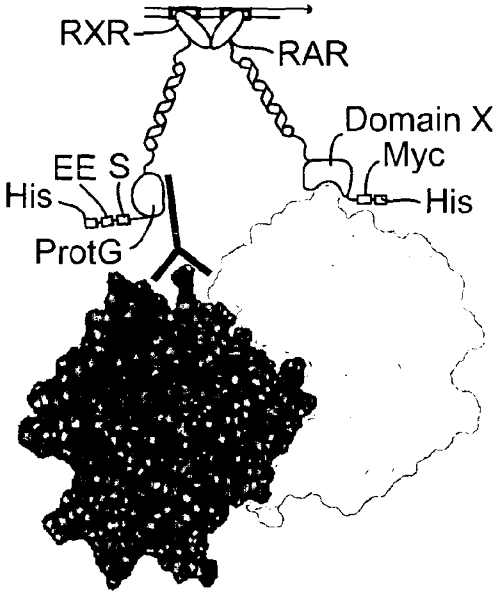
Figure 9:
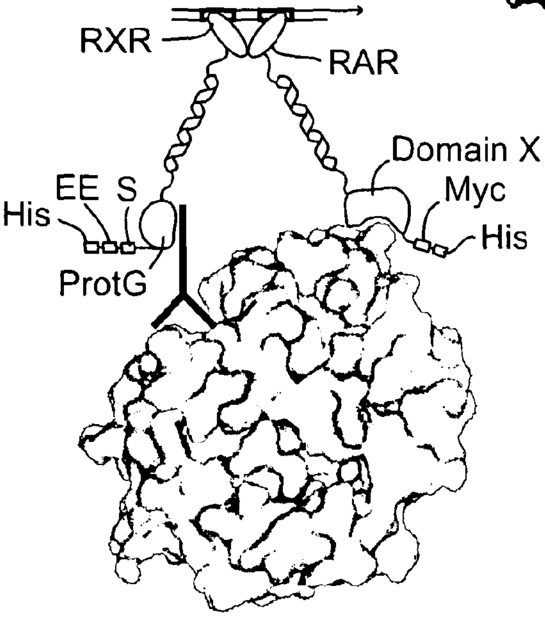

FIGS. 7, 8 and 9 show illustrations of different applications of the invention.

Figure 10A:
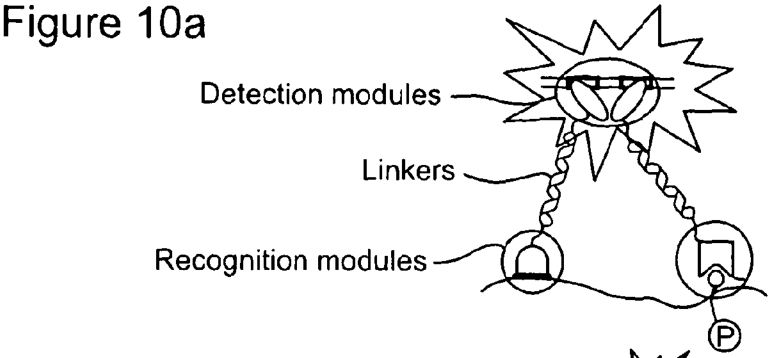

FIGS. 10*a* and *b* show the principle of the biodetector and the assay readouts. 10*a*: the principle of the biodetector: the signal is generated only when the two recognition modules bind their specific epitopes in close proximity; 10*b*: assay & readouts: a specific signal is generated using 5'-biotinylated oligos in combination with streptavidin-HRP conjugated or Rolling Circle Amplification (RCA). The biodetector has the ability to generate a specific signal only when RXR and RAR are in close proximity and simultaneously bind the DR5 DNA consensus sequence to form a heterotrimeric structure with their cognate DNA (DR5). Thus, only when RXR, RAR and DR5 are in a trimeric complex can the signal be generated; monomeric RXR and monomeric RAR do not bind to DR5; RXR and RAR do not form heterodimers in the absence of DR5.

Figure 11:
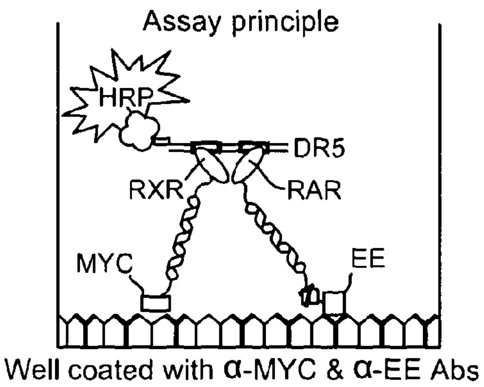
Figure 11:
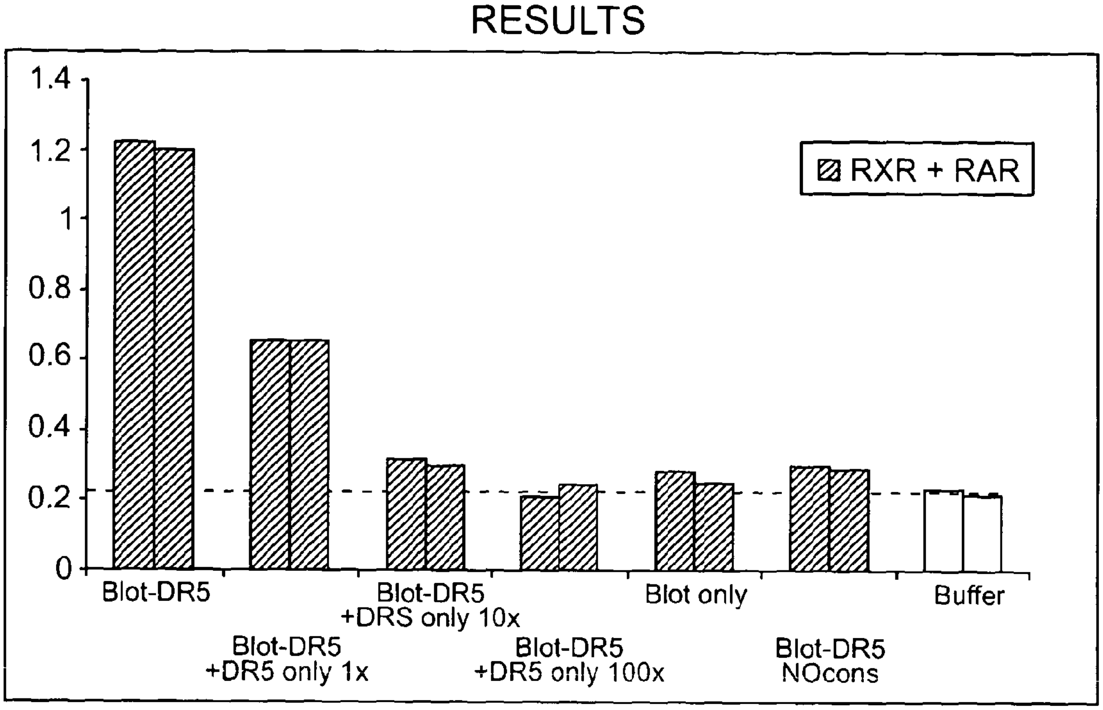

FIG. 11 shows ELISA assays and the readout specificity of the biodetector.

The reagents are added in the following order:

RXR-MYC+RAR-S-EE
Biotinylated dsOligo DR5
Streptavidin-HRP conjugated
TMB substrate.

Method: 96-well microtiter plates were coated with α-EE (Y) and α-MYC (Y) at 10 ng/μl in 100 mM NaHCO3/Na2CO3 (pH 9.6). Excess antibody was removed and wells were blocked using 3% BSA. The biodetectors were then captured in the well as indicated in figures followed by the addition of 50 μl/well of biotinylated-DR5 DNA sequence (BIO-DR5, 5 pmol/μl). Control for specificity is the non-consensus oligo (BIO-non consensus) and un-biotinylated DR5 (competitor) to establish signal specificity. Washes were performed at each step to assure the removal of unbound reagents. Streptavidin-HRP was incubated for 30 min at RT, and after three washes, binding was assessed using TMB substrate. Absorbance was measured at 450 nm. Samples are in duplicate.

Figure 12:
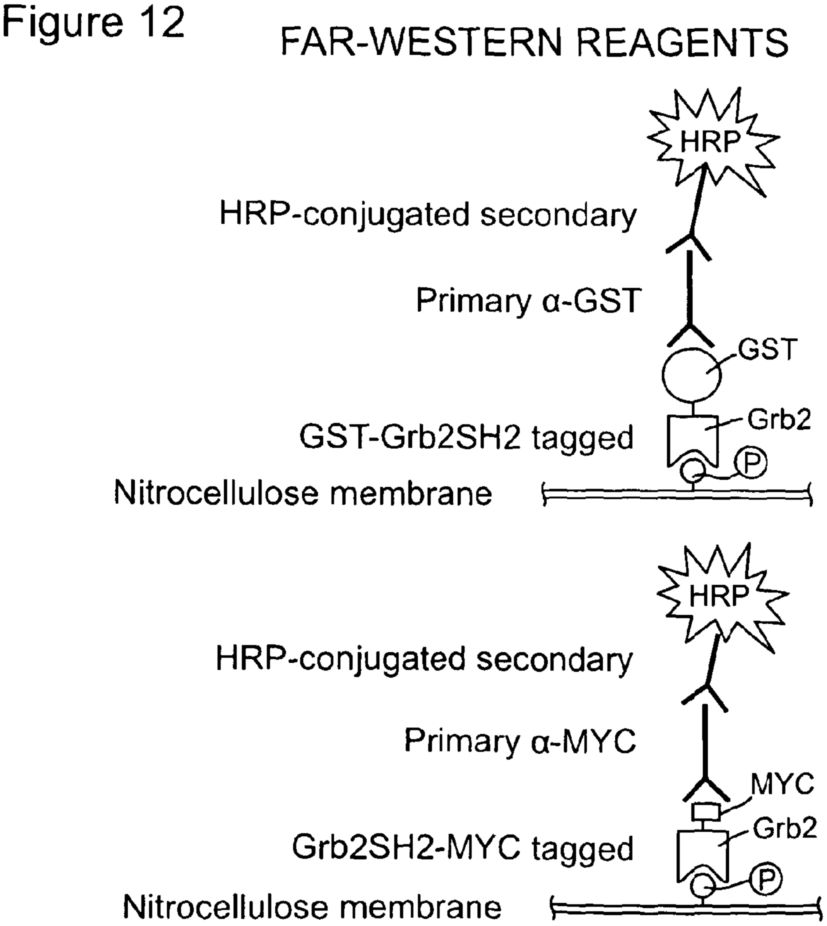
Figure 12A:
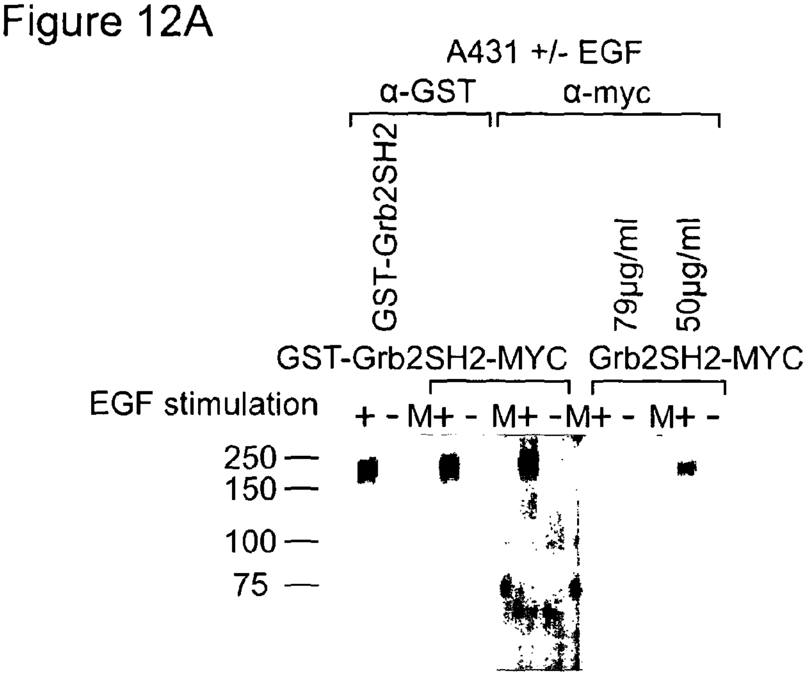
Figure 12B:
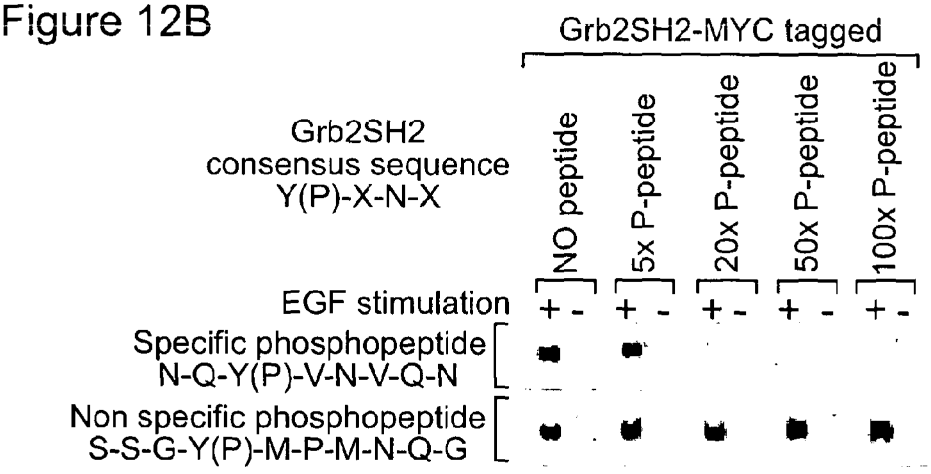
Figure 12C:
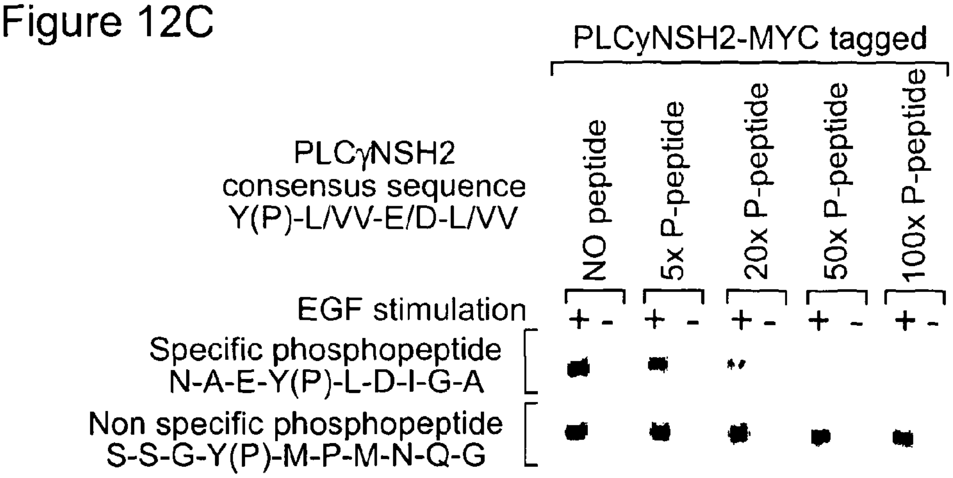

FIGS. 12A-C show by far-westerns that the genetically encoded P-Tyrosine detection Grb2-SH2 & PLCγ-NSH2 are functional.

A. GST-Grb2SH2 & Grb2SH2-MYC tagged domains show a robust and specific interaction with phosphorylated EGFR 1.

Far-westerns using A431 cell lysates detecting EGFR1 which contains Grb2SH2 binding sites when phosphorylated. Cells were stimulated with 50 ng/ml EGF (+) or left untreated (−) and probed with Grb2SH2 tagged with either MYC or GST or both and detected using either α-GST or α-MYC antibody. GST-tagged constructs were used at 50 μg/ml. MYC-tagged constructs were used at 19 μg/ml (molar equivalent of the GST-Grb2SH2 construct) and at 50 μg/ml as indicated.

B. Grb2SH2-MYC tagged domain shows a robust and specific interaction with phosphorylated EGFR1.

A phospho-peptide (P-peptide) containing the Grb2SH2 specific phospho-tyrosine motif (Y(P)-X-N-X), or a non-specific phospho-tyrosine motif, were incubated with the Grb2SH2-MYC tagged domain at increasing concentrations. The concentration of the Grb2SH2-MYC tagged domain is 19 μg/ml. A 20× molar excess of specific peptide competes efficiently with Grb2SH2-MYC for binding.

C. PLCγNSH2-MYC tagged domain shows a robust and specific interaction with phosphorylated EGFR1.

A phospho-peptide (P-peptide) containing the PLCγNSH2 specific phospho-tyrosine motif (Y(P)-L/I/V-E/D-L/I/V), or a non-specific phospho-tyrosine motif, were incubated with the PLCγSH2-MYC tagged domain at increasing concentrations. The concentration of the PLCγSH2-MYC tagged domain is 2.5 μg/ml. A 50× molar excess of specific peptide competes efficiently with PLCγNSH2-MYC for binding.

Figure 13:
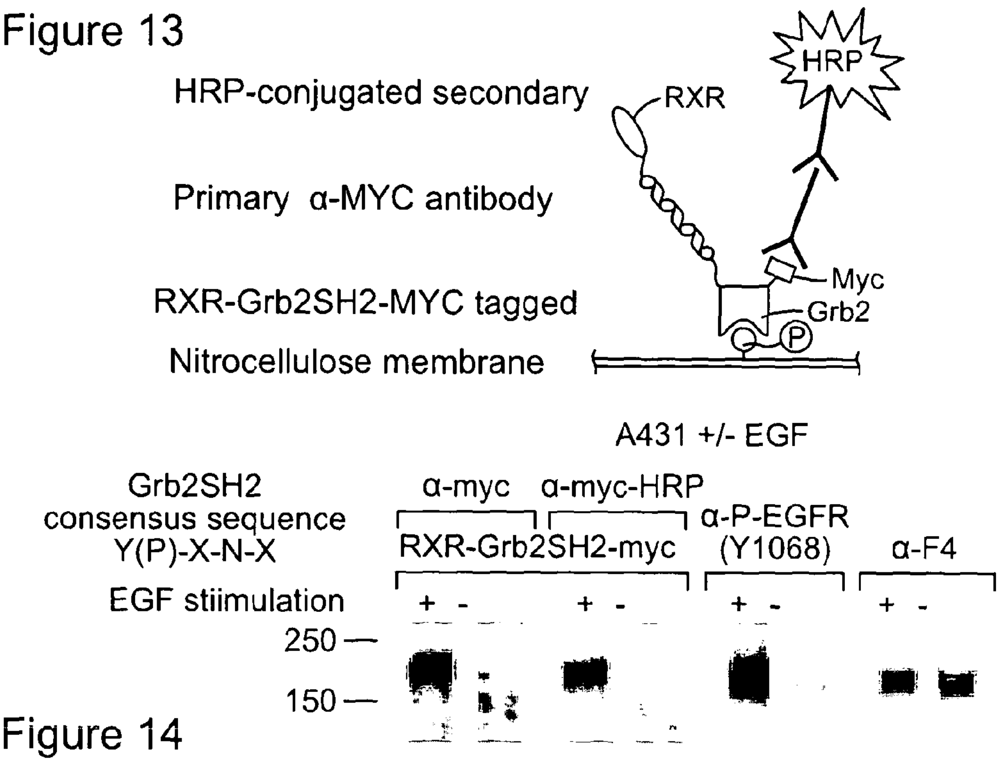

FIG. 13 shows by far-western that the RXR-Grb2-MYC detector reagent is functional. RXR-Grb2SH2-MYC detector reagent shows a robust and specific interaction with phosphorylated EGFR1

Far-westerns using A431 cell lysates detecting EGFR1 which contains Grb2SH2 binding sites when phosphorylated. Cells were stimulated with 50 ng/ml EGF (+) or left untreated (−) and probed with RXR-Grb2SH2 tagged with MYC and detected using either α-MYC antibody or directly conjugated α-MYC-HRP. RXR-Grb2SH2 construct was used at 40 μg/ml (molar equivalent of the GST-Grb2SH2 construct).

Figure 14:
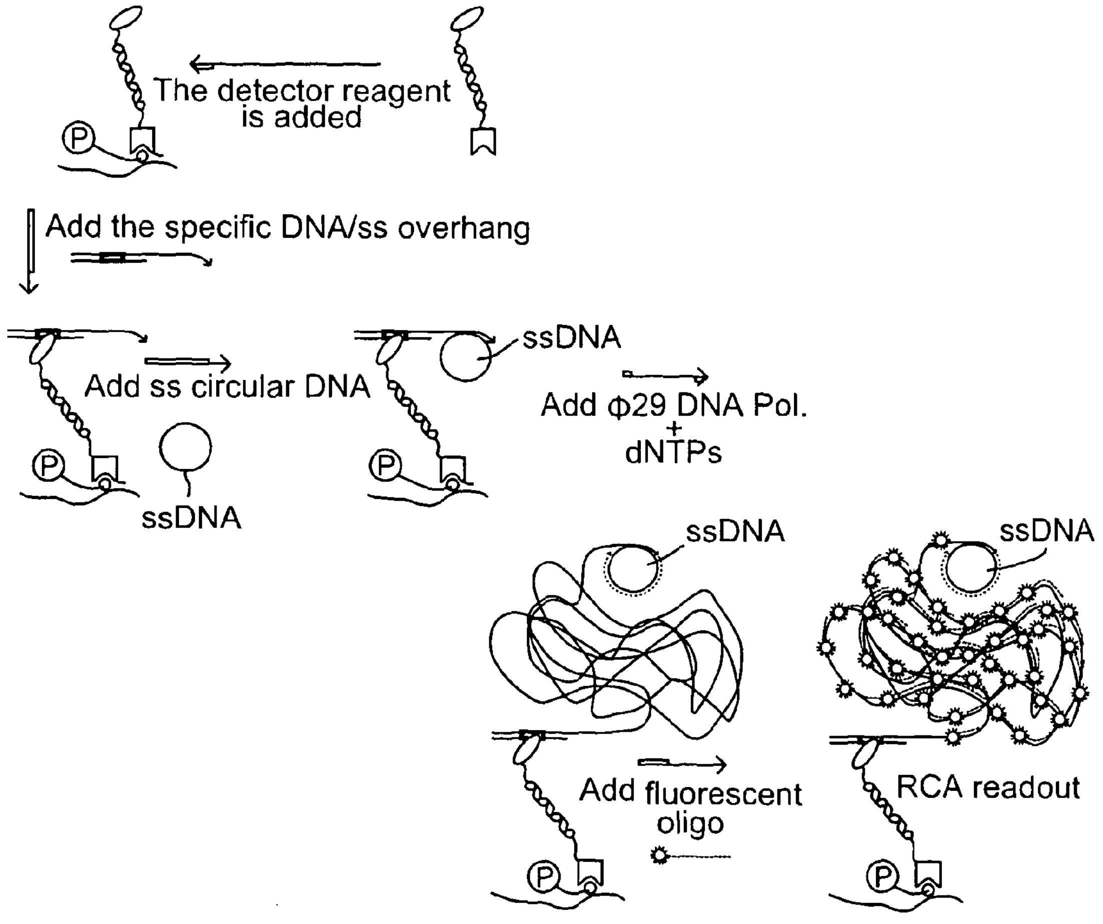

FIG. 14 shows oligonucleotide capture for readout sensitisation

FIGS. 15A-B show the RXR and RAR DNA BDs sequences with the recognition α-helix underlined. Highlighted in blue are the unique restriction sites suitable for cloning, for cassette mutagenesis and for constructing the library; in yellow are highlighted the amino acids responsible for the DNA recognition.

FIG. 15A—RXR DNA sequence (SEQ ID NO. 78), shown as a double-stranded molecule; and RXR polypeptide (SEQ ID NO. 79).

FIG. 15B—RAR DNA sequence (SEQ ID NO. 80), shown as a double-stranded molecule; and RAR polypeptide (SEQ ID NO. 81).

FIG. 16 shows a diagram and a photograph. Far-westerns using A431 cell lysates detecting EGFRI which contains PLCgNSH2 binding sites when phosphorylated. Cells were stimulated with 50 ng/ml EGF (+) or left untreated (−) and extracts fractionated by PAGE and then probed with RAR-PLCgNSH2 tagged with HA and detected using α-HA antibody. RAR-PLCgNSH2 construct was used at 20 μg/ml (100 μg in 5 ml, ~2.5 nmoles).

FIGS. 17A-B show a photograph and a diagram. Western Blot—Block with 5% BSA in TBS/Tw 1 h RT—anti-EE mouse monoclonal 1:500 in TBS/Tw, 1% BSA 1h RT—anti-Mouse-HRP 1:15,000 in TBS/Tw, 1% BSA 30 min RT FIGS. 18A-B show a bar chart and a diagram. The reagents are added in the following order: RXR-Grab2-MYC+RAR-PLCgN-EE: Biotinylated dsOligo DR5; Streptavidin-HRP conjugated; TMB substrate.

FIGS. 19A-B show a bar chart and a diagram. Bis-phosphorylated biotin-oligopetide The reagents are added in the following order: RXR-Grb2SH2-MYC tagged; Primary α-MYC antibody; HRP-conjugated secondary; TMB substrate.

FIGS. 20A-B show a bar chart and a diagram. The reagents are added in the following order: Bis-phosphorylated biotin-oligopetide; Free biotin block; RXR-Grb2SH2 & RAR-PLCgN; Biotin-DR5; HRP-conjugated secondary; TMB substrate FIGS. 21A-B show a bar chart and a diagram The reagents are added in the following order: Bis-phosphorylated biotin-oligopetide: Free biotin block; RXR-Grb2SH2 & RAR-PLCgN+/−competitor; Biotin-DR5; HRP-conjugated secondary; TMB substrate.

FIGS. 22A-B show a bar chart and a diagram The reagents are added in the following order Zif-G/S-PrG-EE or Zif-E3-PrG-EE; Biotinylated dsOligo Zif268-DNA; Streptavidin-HRP conjugated; TMB substrate.

FIGS. 23A-B show a bar chart and a diagram. The reagents ore added in the following order: Zif-G/S-PrG-EE or Zif-E3-PrG-EE+/−anti-F4 Ab (competitor); Biotinylated dsOligo Zif268-DNA; Streptavidin-HRP conjugated; TMB substrate.

FIGS. 24A-B show a bar chart and a diagram. The reagents are added in the following order: Zif-G/S-PrG-EE or Zif-E3-PrG-EE; Biotinylated dsOligo Zif268-DNA+/−non-Biotinylated Zif268-DNA (competitor); Streptavidin-HRP conjugated; TMB substrate.

The invention is now described by way of example. These examples are intended to be illustrative, and are not intended to limit the appended claims.

EXAMPLES

Example 1

Principle of the Invention

The principle of the invention is described in FIG. 6 in steps 1 to 3.

FIG. 6 steps 4-7 show the use of Rolling Circle Amplification (RCA) that can be utilised as a readout and/or as a robust strategy for probe/signal amplification to enhance the sensitivity of the invention.

Typical starting materials (samples) comprise fixed cells or tissues on microscope slides, or membrane-bound denatured proteins from cell lysates.

The principle is described using the example of the Grb2-SH2 domain and the Protein G Ig binding domain binding anti-EGFR1 as the recognition domains on the two fusion proteins of the detection system.

The Grb2-SH2 domain and the Protein G/anti-EGFR1 are the two recognition modules that are used as examples of coincidence detection by western blot analysis of lysates and imaging fixed cells and tissues. If (for example) an scFv is used instead of the Protein G or A or L as a recognition domain then step 1 (addition of an antibody to the epitope of interest) is omitted.

Working the Invention

In this example the samples are incubated with a primary antibody (e.g. anti-EGFR1) that binds the protein epitope.

This is shown in FIG. 6-1.

The fusion proteins (chimeric proteins A and B) are added and incubated.

This is shown in FIG. 6-2.

The cognate specific nucleotide sequence (in this example the DR5 DNA response element) is added and incubated.

This is shown in FIG. 6-3.

Thus, only in those cases where a specific antibody (or an scfv) is close enough to a given modular domain (or two given modular domains/scFvs are in close proximity), (i.e. only when the biomolecular structures bound by the two recognition domains are in close proximity), can RXR-RAR heterodimerisation take place in the presence of DR5.

Once the trimeric complex RXR-RAR-DR5 is formed, the specific DNA sequence flanking the response element can be specifically detected or read out, for example, with oligonucleotide probes and/or PCR techniques, and the complexes are then visualised.

The example given below shows the DR53' end being single stranded, and being used to act as a primer for a Rolling Circle Amplification (RCA) reaction, using single stranded circular DNA as a template for detection.

The single stranded circular DNA is added and incubated.

This is shown in FIG. 6-4.

The amplification solution containing nucleotides together with polymerase is added (nucleotides and polymerase are not shown in figure). The DR53' end acts as a primer for the Rolling Circle Amplification (RCA) reaction generating a repeated sequence product.

Figure 5:
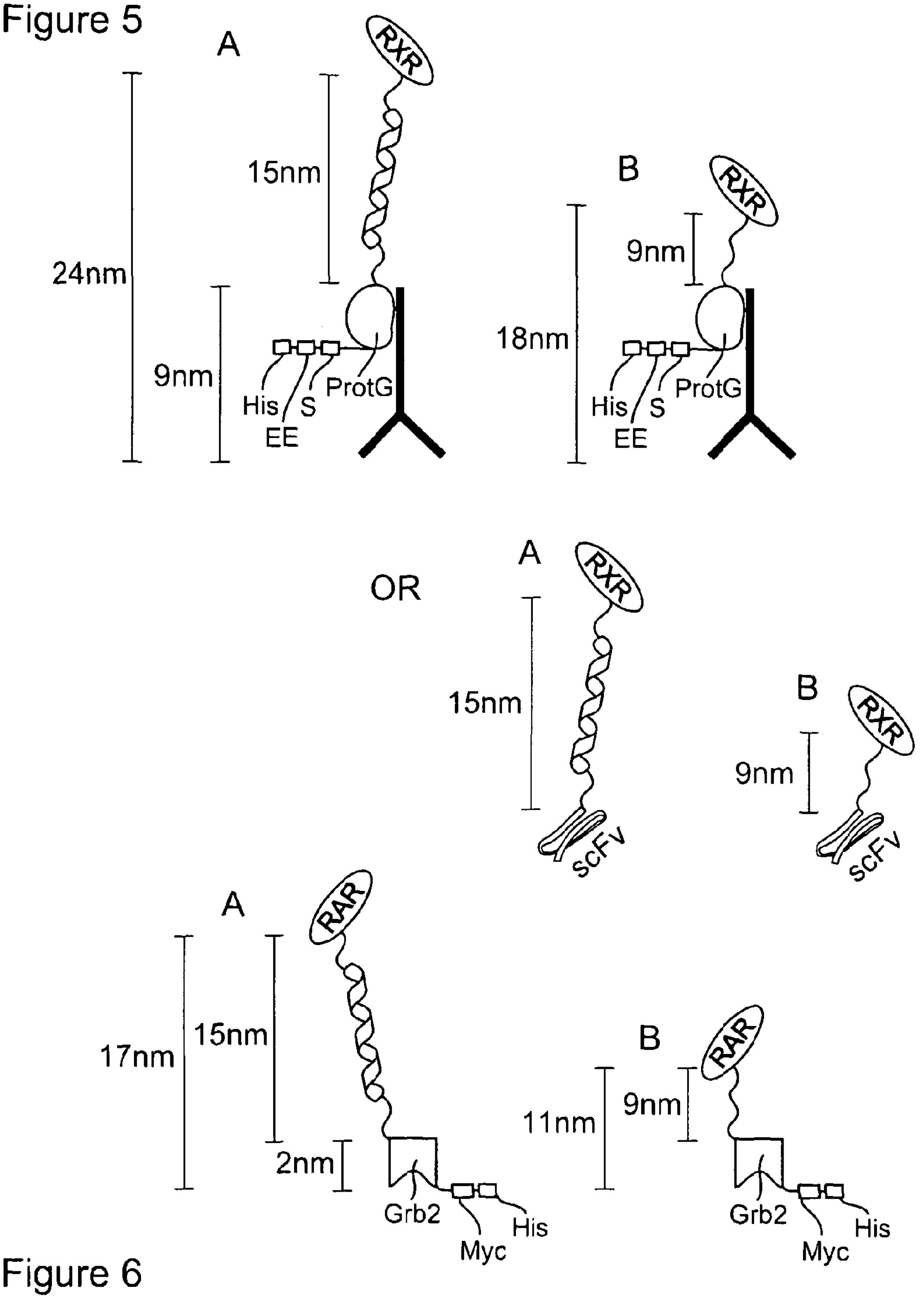

This is shown in FIG. 6-5.

Standard fluorescently labelled oligonucleotides are added and hybridise to the RCA product giving a bright intense spot for detection.

This is shown in FIG. 6-6.

Optional Quantification

The total amount of target protein can be subsequently detected and quantified. This can be achieved by using a free detection module (which in this example is RAR) to bind the other detection module attached to the protein backbone, and still free when in absence of the post-translational modification of interest, so that a trimeric complex can be formed in the presence of the cognate DNA response element. In this example, it is the RAR detection module without the arm and without the Grb2-SH2 recognition module that forms trimeric complexes with the RXR detection modules attached to EGFR1, when in the presence of the DR5 DNA response element. The DR5 response element bound to the newly formed trimeric complex contains different DR5 flanking sequences and can be detected and quantified with a different fluorophore. This is shown in FIG. 6-7.

Example 2

Read Out by Detection of Cognate Nucleic Acid Binding

In example 1, attention has focused on the 9-cis retinoid acid receptor (retinoid X receptor, RXR) which forms heterodimers with many other nuclear receptors including the all-trans retinoic acid receptor (RAR), the thyroid hormone receptor (TR), the vitamin D3 receptor (VDR), the peroxisome proliferator activated receptor (PPAR) and the nerve growth factor induced-B receptor (NGFI-B). All RXR heterodimers preferentially bind DNA response elements composed of two AGGTCA sites arranged in a direct. repeat (DR) configuration with an inter-half-site spacing of 1 to 5 base pair (bp) known as DR1, DR2, DR3, DR4 and DR5 respectively.

FIG. 1 shows a schematic representation of DR response elements, where N represents any nucleotide.

The heterodimer formation between the 9-cis retinoid acid receptor (retinoid X receptor, RXR) and the all-trans retinoic acid receptor (RAR) binding selectively to the direct repeat DR5 is illustrated in FIG. 3.

Example 3

Applications of the Invention

The invention can be used in any setting where it is desired to detect coincidence of biomolecular structures. In particular, the following illustrative applications may be considered.

Detection and Quantification of Proteins and their Post-Translational Modifications.

In one embodiment one fusion protein is used to detect a particular protein and the second fusion protein is used to detect a particular post-translational modification. In this way, signal is only achieved when the modification is found in close proximity to the protein epitope, which finding is taken to infer post translational modification of that protein.

In FIG. 7 the first fusion protein recognition domain is protein G; thus a preliminary step of adding an antibody to the first protein is carried out before addition of the first fusion protein. The second fusion protein comprises Grb2 as the recognition domain. Thus the invention is applied to detect post translational modification (phospho-tyrosine) on the protein of interest.

Detection and Quantification of Protein Proximity

This may be of particular interest e.g. in detecting whether two proteins are part of the same complex.

In FIG. 8 the first fusion protein recognition domain is protein G; thus a preliminary step of adding an antibody to the first protein is carried out before addition of the first fusion protein. The second fusion protein comprises a recognition domain capable of specifically binding a second protein. In this manner a signal is detected only when the two proteins are in close proximity to one another for example as part of the same complex.

An extension of this application gives the possibility of visualising proteins in close proximity to DNA promoters; this can be achieved using sequence specific DNA binding domains like zinc fingers, or investigating the proximity to active promoters, for example using Bromodomains or Chromodomains which specifically recognise acetylated or methylated histones as one of the recognition domains.

Detection and Quantification of Protein Expression

This embodiment permits detection and quantification of a protein with high specificity.

In FIG. 9 the first fusion protein comprises a recognition domain binding a first epitope on a protein of interest; the second fusion protein comprises a recognition domain binding a second epitope on the same protein of interest. In this way, signal is only achieved when BOTH recognition domains bind the protein. This can provide enhanced specificity for single protein detection. This can also be useful in 'footprinting' or masking studies to detect whether particular epitopes are available or soluble or otherwise presented for access by the recognition domain under particular conditions.

Example 4

Manufacture of Fusion Proteins

The fusion proteins of the invention are sometimes referred to as "biodetectors". The oligonucleotide sequences used to clone the range of protein fusions are purchased from MWG Eurofins (http://www.eurofinsdna.com) and full gene synthesis is acquired from GeneArt (http://www.geneart.com). The MultiSite Gateway Three-Fragment technology (Invitrogen, http://products.invitrogen.com) is used to clone the modules of the biodetector and to assemble it; the appropriate cloning flanking regions of each construct, containing the specific Gateway recombination sites, were designed according to the manufacturer's instructions. Invitrogen Gateway technology is a cloning method based on the bacteriophage lambda, which exploits the integrase/att site-specific recombination system. This method provides a rapid and efficient way to clone three DNA segments directionally and in a specific order into a destination vector (pDEST) which contains the recombinant cassette called attR4-attR3. To achieve this, firstly, the PCR products (which in our case are the modules of the bipartite biodetector) are recombined (BP recombination) into pDONOR vectors to generate pENTRY clones; then the pENTRY clones are sub-cloned in frame, by LR recombination, into the destination vector containing the attR4-attR3 cassette. To assemble the biodetector together the pGEX-4T1 (GE Healthcare) expression vector was modified with the Gateway recombination attR4-attR3 cassette to convert pGEX-4T1 into a MultiSite Gateway destination vector that we named pGEX-4T1-DEST(attR4-attR3). The attR4 and attR3 recombination sites were cloned into pGEX-4T1 by PCR and restriction enzyme digestion together with the ccdB and Chloramphenicol resistance genes as it is in the original pDEST R4-R3 cassette of the MultiSite Gateway three-fragment vector construction kit (amino acids 37-2188). Hence, the pGEX-4T1 vector expresses the Glutathione S-transferase (GST) gene in frame with any of the three modules of choice allowing expression and purification from *E. coli* cells. In addition, RXR and RAR detection modules had been generated with an HRV 3C Protease site-specific cleavage site at their N-terminal ends which allows purified protein to be obtained virtually free of vector-encoded sequences (Sequences 1 and 2).

The Gateway technology has been used to carry out the cloning of the three DNA segments (modules) of the detection reagents directionally and in a specific order; however it must be noted, that this technology is not a pre-requisite for producing the detection reagents. Constructs expressing the detection reagents without any gateway recombination sites can be produced or purchased from any source, for example GeneArt (http://www.geneart.com).

Fusion Proteins are expressed and purified using standard laboratory procedures described below.

Example 5

Designing Novel Amino Acid Sequences to Generate Alternative Sequence Recognition Modules The DNA binding domain of RXR and RAR (Sequences 1 and 2) interacts with the DNA major groove through the α-helix of the first zinc finger (FIG. 2). This region is called the recognition helix, and contains at most six exposed residues responsible for discrimination between different half-site DNA sequences. Furthermore, the second zinc finger is involved in forming the dimerisation interface and it is important for the orientation of the heterodimer on its cognate DNA. These features show that the DNA recognition and the heterodimer interactions are separated in the molecular structure and this will allow substitution of the recognition helix with different α-helixes which will discern dissimilar half-site sequences.

For example, the α-helix of RXR and RAR, which recognise the half-site AGGTCA, can be substituted with the helical segment of the glucocorticoid receptor (GR), which recognises the sequence AGAACA instead (Sequences 9a and 9b). This can be achieved by substituting the E with a G in position 42, the G with an S in position 43 and the G with a V in position 46 (FIGS. 15*a* and *b*, Sequences 7 and 8). Thus, to isolate DNA BDs (of established pairs) with different DNA specificity it is necessary to alter the part of the protein sequence responsible for the DNA recognition. There are several possible ways to do this and three especially suitable ways are listed and described below:

Changing Sequence Specificity by Design

1. Sequence substitution of established pairs using directional cloning into plasmid vectors.
2. In vitro mutagenesis of established pairs using double-stranded DNA templates.

Changing Sequence Specificity by Selection

3. Site-directed mutagenesis library creating pools of mutants by "cassette mutagenesis".

1. Sequence Substitution of Established Pairs Using Directional Cloning into Plasmid Vectors Directional cloning requires that the plasmid expressing the DNA BD of interest be cleaved with two restriction enzymes to remove the sequence responsible for the DNA recognition. The two restriction enzymes ideally generate incompatible termini and cut at sites flanking the DNA BD region responsible for the DNA recognition. In our example, Bsu36I and FspI are two restriction enzymes suitable for this purpose aiming to substitute the α-helix of RXR, which recognises the half-site AGGTCA, with the helical segment of the glucocorticoid receptor (GR) which recognises the sequence AGAACA instead (FIG. 15*a*); for the RAR sequence Bsu36I and PmlI restriction enzymes could be used for the same purpose (FIG. 15*b*). The insert to be cloned into the plasmid is a sequence encoding a polypeptide region which is able to recognise a DNA sequence with an alternative specificity, in this case with the GR specificity (FIGS. 15*a* and *b*). The insert has to carry termini that are compatible with those of the double restricted vector.

Protocol 1: Directional Cloning into Plasmid Vectors

Digest the vector and insert (1-2 μg) with the two appropriate restriction enzymes following the manufacturer's instructions. Alternatively the insert is synthesized with the appropriate flanking regions for suitable restriction digestion.

Purify the plasmid vector and insert using a gel purification kit (e.g. Wizard SV Gel and PCR Clean-Up System, Promega) and resuspend them with a suitable amount of $H_2O$ (15-50 μl).

Calculate the concentration of the purified DNAs (in fmol/μl, recommended concentration 10-100 fmol/μl).

Transfer appropriate amounts of the DNAs to sterile 0.5 ml microfuge tubes and add 1 μl of 10×T4 DNA Ligase buffer (containing ATP) and 0.5 μl of T4 DNA Ligase (400 units/μi) in a 10 μl reaction.

The molar ratio of plasmid vector to insert DNA fragment should be approx. 1:1, 1:3 or 1:5 in the ligation reaction.

The DNA fragments can be added to the tubes together with the $H_2O$ and then warmed to 45° C. for 5 minutes to melt any cohesive termini that have re-annealed during fragment preparation. Chill the DNA solution to 0° C. before the remaining ligation reagents are added.

Incubate the reaction mixtures overnight at 16° C. or for 1-2 h at 20° C.

Transform competent *E. coli* with the ligation reactions.

2. In Vitro Mutagenesis of Established Pairs Using Double-Stranded DNA Templates.

In vitro mutagenesis of established pairs using double-stranded DNA templates, aims to specifically alter key amino acids responsible for the DNA recognition which interact with specific DNA bases. In our example, FIGS. 15 *a* and *b* show the six key amino acids of the RXR and RAR DNA BD sequences involved in the DNA recognition highlighted in yellow. In order to achieve the mutations, two oligonucleotides are used to prime DNA synthesis catalyzed by a high-fidelity thermostable polymerase on a denatured plasmid template. The two oligonucleotides both contain the desired mutation and occupy the same starting and ending positions on opposite strands of the plasmid DNA. During several rounds of thermal cycling, both strands of the plasmid DNA are amplified in a linear fashion generating a mutated plasmid containing staggered nicks on opposite strands. The amplified reaction is treated with the restriction enzyme DpnI, which specifically cleaves fully adenomethylated GATC sequences. DpnI will therefore digest the bacterially generated DNA used as template for amplification but will not digest DNA synthesized during the course of the reaction in vitro. DpnI resistant molecules, which contain the desired mutation, are recovered by transforming *E. coli* and selecting with the appropriate antibiotic resistance.

Protocol 2: In Vitro Mutagenesis Using Double-Stranded DNA Templates

In sterile 0.2 ml microfuge tubes, set up a 50 ul reaction mixture containing plasmid DNA (10 ng) and each of the two oligonucleotide primers.

10× reaction buffer (5 μl)
Template plasmid DNA (10 ng)
Oligonucleotide primer 1 (15 pmoles)
Oligonucleotide primer 2 (15 pmoles)
dNTP mixture (0.3 mM each)
$H_2O$ to a final volume of 50 μl
Then add 1 μl of Pfx DNA polymerase (2.5 u/μl).

It is important to add the enzyme at the end.

Place the tubes in the thermal cycler.

Amplify the nucleic acids using the denaturation, annealing, and polymerization times and temperatures listed below.

First step: 2 min at 94° C.
2-18 cycles: 15 sec at 95° C., 30 sec at 52-58° C., 1 min/kb of plasmid DNA at 68° C.
Last step: 5 min at 68° C., 4° C. for ever.

Times and Temperatures May Need to be Adapted to Suit the Particular Reaction Conditions.

After amplification of the DNA verify that the target DNA was amplified by analyzing 10 μl of each reaction by electrophoresis through a 0.8% agarose gel containing 0.5 μg/ml ethidium bromide. As standards, load 50 ng of unamplified linearised plasmid DNA and a 1 kb DNA ladder into the outer lanes of the gel. Digest the amplified DNA by adding 10 units of DpnI directly to the rest of the amplification reaction mix and incubate for 1 h at 37° C.

Transform competent *E. coli* with 1 μl of DNA according to standard laboratory procedures.

Prepare plasmid DNA from at least 10 independent transformants. Screen the DNA preparations for mutations by DNA sequencing or by restriction digestion of plasmid DNA if a site was created or destroyed by the introduced mutation, or if an insertion or deletion was introduced into the template.

Sequence the entire segment of target DNA to verify that the desired mutation has been generated and that no spurious mutations occurred during amplification. More rounds of in situ mutagenesis may be required to mutate the desired sequence.

3. Site-Directed Mutagenesis Library Creating Pools of Mutants by "Cassette Mutagenesis".

A different approach is to select for different DNA binding specificities by analyzing large numbers of variants that are created by cassette mutagenesis in key regions (e.g. the α-helix of the first zinc finger of a specific DNA BD, FIGS. 15*a* and *b*). Methods have been devised to use degenerate pools of oligonucleotides to create large populations of mutants in a single round of site-directed mutagenesis. Thus, a library can be constructed by replacing unique codons with degenerate codons (which encode more than one amino acid) by using designed synthetic oligonucleotides. By utilising appropriately designed oligonucleotides to mutate the sequence responsible for the DNA recognition, the amount of diversity introduced at each position can be varied in a controlled manner. This approach will generate pools of mutants by "cassette mutagenesis". This can be configured to replace the wild type sequence, e.g. the α-helix of RXR and/or RAR which recognises the half-site AGGTCA, with a synthetic pool of double-stranded oligonucleotides encoding for segments with potentially altered DNA specificities. For this purpose there is the necessity for unique restriction sites at both ends of the cassette as described in 1/Protocol 1. These restriction sites are required to be unique to shuttle the synthetic double-stranded oligonucleotide into the correct location, they cannot occur anywhere else in either the plasmid vector or the segment of the wild type gene that it carries. Furthermore, for oriented insertion, the cassette would carry different restriction sites at each end (see FIGS. 15*a* and *b*). Naturally occurring restriction sites in a sequence may not always fulfil these criteria, if this is the case it is necessary to carry out one or more rounds of site-directed mutagenesis (Protocol 2) to create suitable restriction sites at the appropriate locations in the wild type gene. If the introduction of these sites changes the amino acid sequence encoded by the gene, it is also advisable to check that the resulting protein displays appropriate characteristics.

To create a library, two separate sets of oligonucleotides are synthesized that are complementary to the opposite strands of the target DNA. One of these sets consists of a single species of oligonucleotide that is exactly complementary to the sequence of one of the strands of the wild type target DNA (in this example an oligonucleotide at the 5' end containing, at this end, the Bsu36I restriction site, FIGS. 15*a* and *b* is synthesized). The other set consists of a degenerate pool of oligonucleotides that are complementary to the opposite strand (containing FspI (RXR) or PmlI (RAR) restriction sites at the 5' end of the oligonucleotide pool) and that carry the desired mutations in the amino acid positions highlighted in yellow in FIGS. 15*a* and *b*. These two sets of oligonucleotides which are complementary to the target DNA sequence are then mixed together with the target DNA of choice which in this example is the vector encoding for the RXR or RAR DNA BD. Under low stringency conditions, that will allow mismatched sequences to anneal, a polymerase chain reaction (PCR) will be carried out to amplify the pool of mutagenised cassettes containing the appropriate flanking restriction sites. If the oligonucleotides have been designed to yield double-stranded cassettes that carry the appropriate restriction sites at both ends, cohesive termini can be created by digesting the double-stranded cassettes with the suitable restriction enzymes and the cassettes can be inserted directly into the vector of choice in place of the homologous wild type sequence. The mismatches in the recombinant plasmids are repaired in vivo, after the recombinant plasmids have been introduced into competent bacteria. Subsequent replication of the plasmid DNA and segregation into daughter cells allows clones to be isolated that are derived from each DNA strand of the plasmid originally used for transformation. The number of potential variations that can be created with this approach, even in a circumscribed region of the protein, is extremely large.

The choice of how many positions to mutate, and how diversely to mutate them, depends on standard considerations of the library size versus theoretical diversity. In one example, we could use the RXR and RAR DNA BD sequences and would randomize those positions, highlighted in yellow in FIGS. 15*a* and *b*, which make direct contacts with the base pairs of the DNA. In addition, we might also randomize some positions which are adjacent (or lie between) these, as their identity could well influence the fine structure of the DNA recognition helix. In general we would not aim to mutate those amino acids which make contact with the DNA backbone, as the crystal structure of the RXR and RAR BDs suggests that they do not play a major role in sequence recognition although they are undoubtedly important in binding.

The objective is to select for DNA BDs that have very low or no affinity for their cognate DNA sequence as monomers (they will not bind with enough strength as monomeric entities) but they will bind cooperatively as a pair to their cognate DNA sequence forming a stable trimeric complex. To select from a library using these criteria we need to break the overall screening design into a set of simpler selection steps. In order to do this the two zinc fingers of choice (in our example RXR and RAR DNA BDs) have to be linked together for example with a simple Glycine-Serine linker (e.g. pAK100-RXR-G/S-RAR DNA BDs phage display construct). The first round of selection would be with a library created with only the first zinc finger randomised. This will allow selection for a novel first half site DNA binding sequence retaining the same DNA specificity for the second zinc finger. In parallel, the second zinc finger can be randomised following the same selecting criteria. Then the selected randomised fingers can be matched and linked together to create novel heterodimers to be again selected for their ability to bind only as obligate heterodimers. In order to do so the screening would be carried out in the presence of a soluble DNA competitor coding for only the half site DNA recognition sequence so that any domain binding as a monomeric entity would be minimised and those acting as obligate heterodimers would be enriched. The selected heterodimer/s can then be cloned separately in a suitable expressing vector, following standard laboratory procedures, so that the two monomeric parts are expressed individually. Affinity and specificity of the novel selected pair/s can be measured and evaluated as described in protocols 6 and 7.

Protocol 3: Library Cassette Construction

Design and synthesize a set of oligonucleotides, each between 50-70 bases in length that anneal at the ends of the library cassette and with the appropriate flanking restriction sites.

Generate full length double-stranded cassettes by PCR amplification using the RXR and RAR DNAs as templates. Set up the PCR reaction by mixing the following in order:

10× reaction buffer (5 μl)
Template plasmid DNA (10-100 ng)
Oligonucleotide primer (15-100 pmoles)
Degenerated oligonucleotide primer (15-100 pmoles)
dNTP mixture (0.3 mM each)
$H_2O$ to a final volume of 50 μl
Then add 1 μl of Pfx DNA polymerase (2.5 u/μl).

It is important to add the enzyme at the end.

Set up as many tubes as necessary to achieve the right complexity. Place the tubes in the thermal cycler. Amplify the nucleic acids using the denaturation, annealing, and polymerization times and temperatures listed below.

First step: 2 min at 94° C.

2-18 cycles: 15 sec at 95° C., 30 sec at 52-60° C., 1 min/kb of plasmid DNA at 68° C.

Last step: 5 min at 68° C., 4° C. indefinite.

Verify that the PCR product is of the correct size by agarose gel electrophoresis. PCR conditions may need to be optimized in each individual case.

Purify the PCR product using a PCR purification kit (e.g. Wizard SV Gel and PCR Clean-Up System, Promega) and resuspend them with a suitable amount of $H_2O$.

Calculate the concentration of the purified DNAs (in fmol/μl, recommended concentration 10-100 fmol/μl).

Digest the purified DNA cassettes using the appropriate restriction enzymes to produce cohesive termini.

Prepare the digested DNA cassette for cloning by using agarose gel purification: run the digested cassette on a 2% low melting point agarose gel in 1×TAE containing 0.5 μg/ml ethidium bromide. Excise the band of interest from the gel and extract the DNA using a gel purification kit.

Quantitate the DNA yield by absorbance at 260 nm and store the cassette in distilled water at −20° C.

Protocol 4: Preparing the Phage Vector DNA and Cloning the DNA BD Library

Transform a suitable strain of *E. coli* (e.g. TG1) with a phage display vector, for example pAK100 expressing the RXR and RAR DNA BDs fused in frame with the gene coding the filamentous phage gene III (gIII). For cloning RXR and RAR DNA BDs into the phage display vector pAK100 both the RXR/RAR DNA BDs and the phage display pAK100 have to be digested with the SfiI restriction enzyme for 3 to 4 h at 50° C. Following protocol 1 for cloning into plasmid vectors will generate the pAK100-RXR DNA BD or pAK100-RAR DNA BD phage display constructs.

Using the pAK100-RXR DNA BD phage display construct as an example, transform the *E. coli* TG1 cells with the pAK100-RXR DNA BD phage display construct. Plate the tranformant colonies on TYE agar plates supplemented with 25 μg/ml chloramphenicol.

Using a single transformant colony, inoculate a 2 ml "starter" culture in 2×TY containing 25 μg/ml chloramphenicol. Incubate with shaking for 4 h at 37° C. and then transfer the culture into a 2 L flask containing 1 L of the same medium. Incubate with shaking for up to 15 h at 37° C.

Purify the double-stranded replicative form phage DNA from the 1 L bacterial culture using a standard plasmid purification kit such as the Wizard Maxiprep kit from Promega. Digest 20 μg of the pAK100-RXR DNA BD phage display construct with the appropriate restriction enzymes. For cloning into pAK100-RXR DNA BD phage display construct these enzymes are Bsu36Iand FspI.

To prepare the randomized gene cassette see Protocol 3.

Prepare the vector for cloning using agarose gel purification: run the digested vector on a 0.8% low melting point agarose gel in 1×TAE buffer containing 0.5 μg/ml ethidium bromide. Excise the band of interest from the gel under long wave UV light and extract the DNA using a gel purification kit.

Perform ligations with a molar ratio of insert to vector of between 3:1 and 5:1. It is often worthwhile to carry out small scale trial ligations to identify those giving optimum ligation efficiency. For library construction, ligate 0.2-0.5 μg of digested vector DNA and the appropriate amount of digested randomized gene cassette (from Protocol 2) in a reaction mix containing 1×T4 DNA ligase buffer and 800 units of T4 DNA ligase in a volume of 10-30 μl. Incubate the reaction mix at 16° C. for 15 h.

Ethanol precipitate the ligated DNA. Carefully wash the pellet in 70% ethanol DNA to remove excess salt which could cause arcing during electroporation. Resuspend the dried pellet in MilliQ $H_2O$ to a final concentration of 0.2-0.5 μg/μl.

Electroporate the purified ligated DNA in 1 μl aliquots into electrocompetent *E. coli* strain TG1, use TYH plates and medium supplemented with 25 μg/ml chloramphenicol.

Phage Selections

Having constructed a phage display library, DNA BD variants with novel DNA binding properties can be rapidly isolated through sequential rounds of affinity selection. This is conveniently done by screening the library against synthetic, biotinylated DNA targets, which are captured on a streptavidin-coated matrix (e.g. streptavidin-coated tubes or plates or streptavidin-coated paramagnetic beads such as those manufactured by Dynal).

Unbound clones are washed away while selected clones are retained, eluted and amplified by passaging through a bacterial host. By altering binding and washing conditions, a range of DNA BDs with varying affinity can be generated. In addition, the inclusion of soluble competitor DNA allows selection for variants with predetermined binding specificity for one sequence over another. A general method developed for use with zinc finger domains and applicable for DNA binding selections is described in Protocol 5.

Analysis of Selected Phage Clones

The DNA sequences of phage clones recovered from selections for DNA binding can be identified by sequencing the appropriate part of the phage genome using standard methods.

Protocol 5: Phage DNA Binding Selections

A. Preparation of phage

Transfer cells from fresh or frozen bacterial library stock to 200 ml of 2×TY containing 25 μg/ml chloramphenicol. Transfer a number of viable bacterial cells approximately 10 fold in excess of the library size, to ensure the library diversity is maintained. Viable cell concentration in the frozen stock can be determined by plating out serial dilutions on to appropriate plates.

Incubate the culture with orbital mixing at 250 rpm for 16 h at 30° C. Prepare the phage supernatant by centrifuging the overnight culture at 4000 g for 15 min. Remove and keep the supernatant and store at 4° C. The supernatant can be titered using standard laboratory procedures.

B. Selections

Synthesize the desired target DNA oligonucleotides and include a 5'-biotin group. For dsDNA sites, synthesize a complementary non-biotinylated second strand and anneal the two complementary oligonucleotides by mixing 10 μl of each oligonucleotide strand, from 10 pmol/μl stocks. Heat the samples for 3 min at 94° C., and then cool them to 4° C., at a rate of 0.5° C. per min in a thermocycler block. When cool, dilute the solution to 1 pmol/μl final concentration with water and store it at −20° C.

Add biotinylated target sites (typically 1 pmol) in 50 μl PBS to streptavidin-coated tubes. Incubate the tubes for 30 min at 20° C.

Add 1 ml of PBS containing 5% BSA to the tube to block non-specific binding sites. Incubate the tubes for 1 h at 20° C.

Dilute the phage supernatant 1:10 in 1 ml PBS containing 1% BSA, 0.1% Tween-20 and 20 μg/ml sonicated salmon sperm DNA. To improve the specificity of the selection, add target-related soluble competitor oligonucleotides.

Add up to 100-fold excess of competitor relative to the amount of biotinylated target site.

Discard the blocking solution from the nucleic acid-coated tube and apply 1 ml of the diluted phage supernatant solution. Incubate the tube for 1 h at 20° C.

Discard the binding mixture and wash the tube 3-5 times with 1 ml PBS containing 1% BSA, 0.1% Tween-20 and once with 1 ml PBS alone.

Elute the retained phage by adding 100 μl of 0.1 M triethanolamine and incubating for 15 sec. Transfer the solution to a new tube and immediately neutralize it with an equal volume of 1 M Tris (pH 7.4).

Prepare a logarithmic phase culture of *E. coli* TG1 by inoculating a sample of 2×TY with 1/100 volume of an overnight culture and incubating at 37° C. for approximately 2 h. The inoculum must be derived from colonies grown on a plate of M9 minimal agar to ensure expression of the F' pilus as this is required for phage infection.

Infect 0.3 ml logarithmic-phase *E. coli* TG1 with 50 μl of eluted phage by mixing and incubating the mixture for 1 h at 37° C. without shaking.

Transfer the infected bacterial cultures to 2-5 ml of 2×TY containing 25 μg/ml chloramphenicol. Incubate the cultures with orbital mixing at 250 rpm for 16 h at 30° C. in order to produce phage for subsequent rounds of selection.

Repeat the selection procedure for 3-5 rounds using, instead of streptavidin-coated tubes, microtitre plates or streptavidin-coated paramagnetic beads to reduce selection of non-specific binding.

After the final round, spread the infected bacteria on plates containing TYE agar with 25 μg/ml chloramphenicol. The selected clones are now ready for further characterization as described below.

Testing Specificity Using the Electrophoretic Mobility Shift Assay (EMSA)

The electrophoretic mobility shift assay (EMSA) can be used to characterize protein-DNA interactions. The technique is based on the observation that the electrophoretic mobility of DNA can be decreased when a protein is bound to it. The assay is easy to perform and its results are highly reproducible. Protocol 6 describes how to label the DNA for use in EMSA experiments, while Protocol 7 provides the method for performing the assay.

In the EMSA assay, a radiolabelled DNA probe (that contains a specific DNA sequence recognised by the selected DNA BDs) is mixed together with the two DNA BDs that we want to test for their ability to form obligate heterodimers. The mix will contain free protein, free DNA probe and DNA-protein complexes if the DNA BDs bind their cognate DNA. Any homodimer formation will be analysed by incubating the two DNA BDs with the same DNA sequence separately. These components can be separated by non-denaturing acrylamide gel electrophoresis following standard laboratory procedures. The rate of migration of each component will be determined by its net charge, its mass, and its shape. The free DNA probe will migrate more rapidly through the gel than will DNA that is bound to protein.

Specificity can be determined by adding non-radiolabelled competitor DNA to the mix; the non-radiolabelled DNA will compete with the labelled probe for the DNA binding sites. The relative concentrations and relative affinities of the labelled and unlabelled DNA in the mix will determine the intensity of the retarded band. Specificity can also be tested by showing that a non-specific competitor DNA (DNA with unrelated sequence) cannot prevent the DNA BDs from binding to their cognate DNA; if the non-specific competitor is able to displace equimolar concentrations of the probe then the DNA-protein interaction has low sequence affinity and specificity. On the other hand, if the non-specific competitor in 100× molar excess does not displace the DNA-protein interaction the complex has good affinity and specificity. Participation of both receptors in the heterodimeric complex can also be demonstrated by performing supershift experiments using antibodies that recognize the individual DNA binding proteins as described in Protocol 7.

Protocol 6: Preparation of End-Labelled Oligonucleotide Probes Using T4 Polynucleotide Kinase (T4-PNK)

Mix 100 ng of oligonucleotide DNA together with 25 μCi [γ-32P]ATP in 50 μl of T4-PNK buffer. Add 10 units of T4-PNK enzyme and incubate at 37° C. for 1 h.

Add cold ATP to the reaction tube to a final concentration of 200 μM.

Separate the free nucleotides from the labelled probe using a 1 ml Sephadex G50 spin column.

Mix 100 ng of labelled DNA with 100 ng of the complementary unlabelled probe strand. Anneal the oligonucleotides.

Protocol 7: Electrophoretic Mobility Shift Assay (EMSA)

Express and purify the DNA BDs as described in Protocol 12.

Set up a non-denaturing 4-8% acrylamide gel using 0.5× TBE running buffer (1×TBE is 90 mM Tris-borate pH 8.5, 1 mM EDTA).

Incubated DNA BDs either together or alone (30 ng) with approximately 0.5-1 ng of $^{32}P$-labelled DNA probe with or without 100-fold molar excess of cold competitor or non-specific competitor oligonucleotide.

Incubate the mix for 10 min at RT in a 20 ul reaction in EMSA binding buffer (10 mM Hepes pH 7.9, 40 mM KCl, 1 mM DTT, 0.05% NP-40, 2 ug poly(dl-dC), and 6% glycerol).

Perform supershift experiments by adding antibodies to the binding reaction, and incubate at RT for an additional 10 min.

Load the reaction mix onto the gel. Run the electrophoresis at 7.5-12.5 V/cm for 90-120 min. The progress of the electrophoresis may be monitored by loading a blank binding reaction containing 0.01% (w/v) xylene cyanol and 0.01% (w/v) methylene blue. In a 5% non-denaturing gel, the methylene blue will co-migrate with a 30 nucleotide probe.

Transfer the gel to moistened filter paper and dry by heating to 70° C. under vacuum. Perform autoradiography with an enhancing screen at −80° C. for 6-24 h.

Example 6

Using RXR-DBD and RAR-DBD

We have demonstrate the invention for coincidence detection through development of a bipartite biodetector co-captured in an ELISA format (FIG. 10*a*).

Figure 10B:
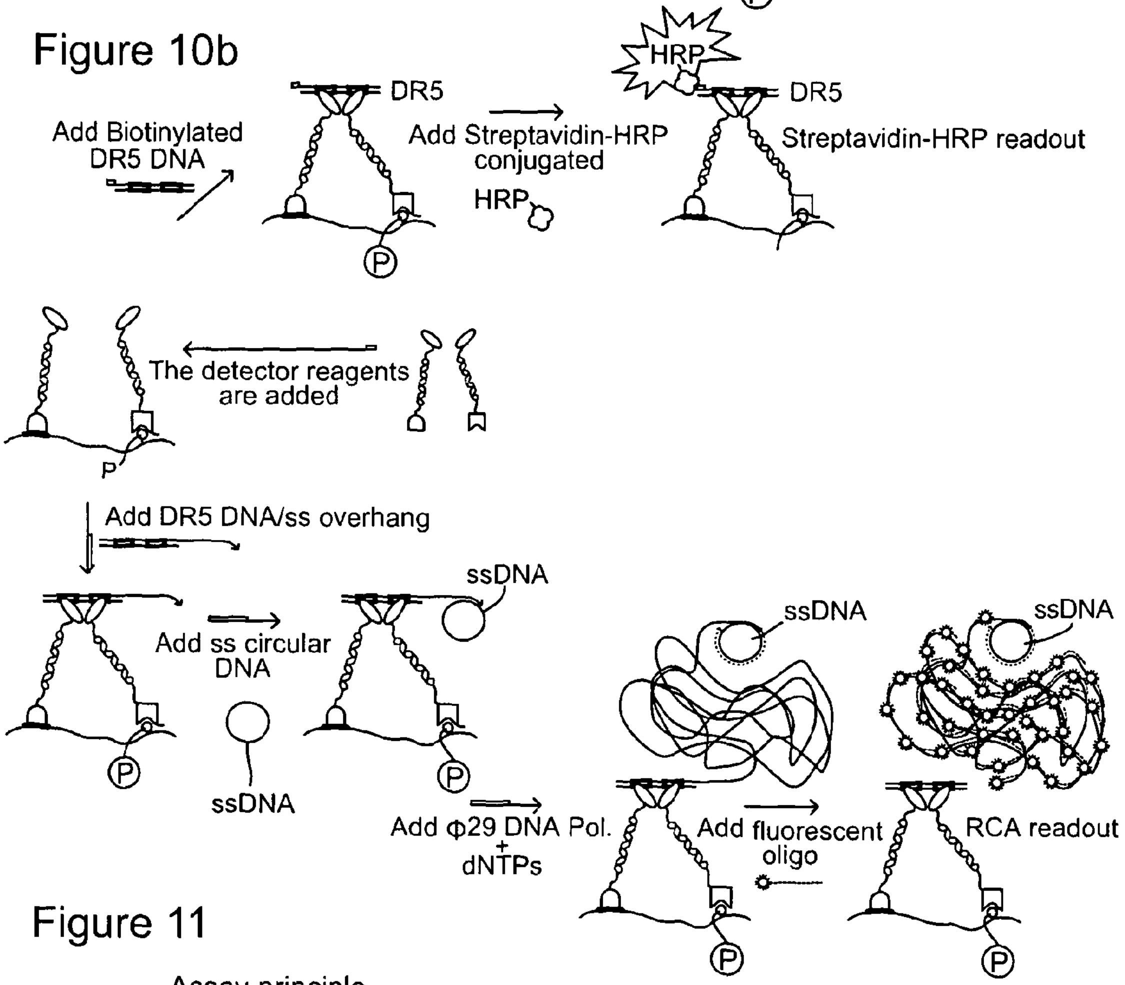

We have exemplified this using the 9-cis and the all-trans retinoic acid receptor DNA binding domains (DBDs; RXR-DBD and RAR-DBD) which bind to the direct DNA repeat DR5 as obligate heterodimers. The principle of the detection is described using the RXR and RAR DBDs expressed in frame with MYC and S-EE tags, respectively (RXR-MYC and RAR-S-EE, sequences 15 and 16). The MYC and S-EE tags expressed in the exemplary biodetector are surrogates for the recognition modules that are required for antigen recognition. When the RXR-MYC and RAR-S-EE DBD fusion constructs are captured in suitably close proximity, the DBDs are able to form a heterotrimeric complex with the double-stranded DNA DR5 which may contain any flanking sequence for suitable readout. The readout associated with binding can be amplified using a range of means including the coupling of biotin to the DR5 oligomer in conjunction with HRP based detection or using a rolling circle amplification reaction (RCA) (FIG. 10*b*). The two recombinant proteins comprising the prototype have been shown to be produced efficiently and have been purified from bacteria under native conditions. We have carried out successfully ELISA experiments with the prototype using antibody capture of the two components, providing a solid foundation for the functionality of the device (FIG. 11). Based on differential antibody plating density we also established a detection range of 22 nm for the current prototype device. Meaning 22 nm is the maximum suitable length to span the distance between the binding sites of the two recognition modules required for antigen/post-translational modification recognition; if the distance is more than 22 nm the trimeric complex cannot be formed because the two elements of the bipartite biodetector are too far apart.

Furthermore, we have characterised the SH2 domain from Grb2 and PLCγN (Grb2-SH2 and PLCγN-SH2, sequences 17 and 18) as having robust interactions with phosphorylated EGFR1, and their specificities have been established (FIG. 12). We have also fused Grb2-SH2 to one element of the exemplified coincidence biodetector (RXR) and established that this modular fusion protein (RXR-Grb2-MYC, sequence 20) will express well in bacteria, can be purified and is functional (FIG. 13).

In combination, the data indicate that the novel coincidence detector itself can be produced in recombinant form and exhibits the desired coincidence behaviour. Moreover when fused to a recognition module the fusion protein remains soluble, can be purified and retains function.

Protocol 8: Enzyme-Linked Immunosorbent Assay (ELISA)—(FIG. 11)

ELISA assays were carried out by coating 500 ng of α-MYC and α-EE antibodies diluted in 100 mM bicarbonate buffer (50 ul/well, pH 9.6). Antibodies were coated for 2 h at RT in a microtiter plate (MaxiSorp, Nunc). The wells were then washed once with 200 ul of PBS buffer (pH 7.3) and incubated 0/N at 4° C. with 200 ul of blocking buffer (PBS+3% BSA). The biodetectors where then added at the concentration of 0.7 pmol/well (50 ul/well in 150 mM NaCl, 50 mM Tris pH 7.6, 10% glycerol and 1% BSA) and incubated for 1 h at RT. After washing three times with 200 ul of PBS/0.1% Tween-20 (PBS/Tw), 50 μl of biotinylated-DR5 DNA sequence (Biot-DR5, 5 pmol/μl in PBS/Tw+1% BSA) were added to the wells and plates were incubated for 1 h at RT. After washing three times with PBS/Tw, each well was incubated with Streptavidin-HRP conjugated diluted 1:3,000 in PBS/Tw+1% BSA. Plates were then washed three times with PBS/Tw and 100 ul of TMB (Thermo Scientific) was added and incubated for 5-10 min. The reaction was stopped by adding 100 ul of 2 M $H_2SO_4$ and the optical density (O.D.) was read at the wavelength of 450 nm.

Western and Far-Western Blotting—(FIGS. 12 and 13)

Far-western blotting is a convenient method to characterize protein-protein interactions, in which protein samples of interest are immobilized on a membrane and then probed with a non-antibody protein. In contrast to western blotting, which uses specific antibodies to detect target proteins, far-western blotting detects proteins on the basis of the presence or the absence of binding sites for the protein probe. When specific modular protein binding domains are used as probes, this approach allows characterization of protein-protein interactions involved in biological processes such as signal transduction, including interactions regulated by post-translational modification.

Protocol 9: Western Blotting 100 mM DTT was added to the denatured cell lysates (Protocol 9) and 5 μl was loaded onto an 8% polyacrylamide gel. The gel was run for 20 minutes at 100V; once the solvent front passed through the stacking buffer, the voltage was increased to 120V and the gel run for ~1 h.

The gel was transferred to a nitrocellulose membrane in transfer buffer (48 mM Tris, 39 mM glycine, 0.0375% SDS, 10% methanol) for 1 h at 100V. The membrane was blocked in 5% BSA in Tris buffered saline (TBS) for 1 h at RT or in 3% BSA O/N at 4° C. and then incubated with one of the following antibodies:

Mouse monoclonal F4 anti-EGFR1 antibody (Santa Cruz Biotechnology) at 1:1,000 dilution in 1% BSA 0.1% Tween for 1 h at RT.

Rabbit monoclonal anti-phospho-EGF receptor (Tyrosine 1068) antibody (Abcam) at 1:50,000 dilution in 1% BSA TBS 0.1% Tween for 1 h at RT.

The membranes were washed three times in TBS with 0.1% Tween and then incubated with polyclonal goat anti-mouse or anti-rabbit immunoglobulins conjugated to HRP (Dako) at 1:2,000 dilution in 1% BSA in TBS with 0.1% Tween for 30 minutes at RT.

The membranes were washed twice for five minutes in TBS with 0.1% Tween and once for 10 minutes in TBS with 0.1% Tween. Bound probe was detected by chemiluminescence using the ECL kit (Amersham Pharmacia).

Protocol 10: Far-Western Blotting

Lysates were separated by SDS/PAGE and transferred to nitrocellulose. The membrane was blocked in 5% BSA in TBS for 1 h at RT or in 3% BSA O/N at 4° C. Membranes were incubated with the appropriate GST-tagged or MYC-tagged probe as indicated in the figures for 1 h at RT, then washed twice with TBS and incubated with one of the following mouse monoclonal anti-GST or anti-MYC antibodies:

Mouse monoclonal anti-GST (Novagen) 1:10,000 dilution in 1% BSA in TBS with 0.1% Tween at RT for 1 h.

Mouse monoclonal anti-MYC 1:500 dilution in 1% BSA in TBS with 0.1% Tween at RT for 1 h.

Membranes were washed three times in TBS with 0.1% Tween and then incubated with HRP conjugated anti mouse monoclonal antibody at 1:15,000 dilution in 1% BSA 0.1% Tween for 30 minutes at RT.

The membranes were washed twice for five minutes in TBS with 0.1% Tween and once for 10 minutes in TBS with 0.1% Tween. Bound probe was detected by chemiluminescence using the ECL kit (Amersham Pharmacia).

Protocol 11: Preparation of A431 Cell Lysate

Cells were cultured in DMEM containing 10% Foetal Bovine Serum, glutamax and antibiotics. Cells were plated in 10 cm dishes with $1\times10^6$ cells per dish. 70% confluent cells were serum starved in DMEM containing 0.1% FBS for 16 h and then treated with 50 ng/ml EGF for 10 minutes at 37° C. The cells were gently rinsed twice with cold PBS and were harvested in 2.5 ml sample buffer (50 mM Tris-Cl pH6.8, 2% w/v SDS, 0.1% bromophenol blue, 10% v/v glycerol). The harvested cells were passed through a 19 gauge needle 20 times and placed at 95° C. for 10 minutes. The lysate was spun down at 13,000 rpm for 5 minutes to clear debris and aliquots of 100 μl were taken and stored at −80° C.

Protocol 12: Protein Expression and Purification of the GST-Tagged and MYC-Tagged SH2 Domains, and of the Detector Reagent RXR-Grb2-MYC BL21 plysS (Invitrogen) bacteria were transformed with pGEX (GE Healthcare) vectors expressing the SH2 domains of interest or the RXR-Grb2-MYC detector reagent. 250-500 ml cultures were grown and expression was induced with 1 mM IPTG for 4 h at 37° C. (SH2 domains) or 2 h at RT (RXR-Grb2-MYC detector reagent). Bacteria were harvested by centrifugation at 4,500 rpm (3,076 g) for 15 minutes at 4° C. The cell pellets were resuspended in a suitable amount of BugBuster reagent (5-10 ml) following the manufacturer's instructions. Soluble proteins were separated from insoluble material by centrifugation at 27,000 g for 15 minutes at 4° C. Protein purifications from the soluble fractions were carried out with standard laboratory procedures using Immobilised Glutathione (Thermo Scientific).

The purification procedure was monitored by running samples of each step of the purification procedure on a 12% polyacrylamide gel. Elution fractions containing protein were pooled and dialysed overnight at 4° C. against 50 mM Tris pH7.6, 150 mM NaCl, 50% glycerol, 1 mM DTT and then aliquoted and stored at −20° C.

Protocol 13: Enzyme-Linked Immunosorbent Assay (ELISA) on Peptide Captured Plate—(FIGS. 18-21)

ELISA assays were carried out by coating 125 ng/well (2.4 pmol/well) of streptavidin diluted in 100 mM bicarbonate buffer (50 μl/well, pH 9.6). Streptavidin was coated for 2 h at RT in a microtiter plate (MaxiSorp, Nunc). The wells were then washed once with 200 ul of 0.8× sodium citrate buffer (0.8×SSC: 120 mM NaCl, 12 mM sodium citrate) and incubated 0/N at 4° C. with 200 μl of blocking buffer (3% BSA in 0.8×SSC). The appropriate biotinylated phospho-peptide/s were then added at the concentration of 1.2 pmol/well in 0.8×SSC with additionally 1% BSA and incubated for 1 h at RT. After washing three times with 0.8×SSC containing 0.1% Tween 20 (0.8×SSC/Tw) a blocking step was carried out using biotin at the concentration of 40 ng/well (160 pmol/well in 0.8×SSC buffer). Biotin was incubated for 10 min at RT. The wells were then washed three times with 200 ul of 0.8×SSC containing 0.1% Tween 20 and the biodetectors were then added at the concentration of 2 pmol/well (50 ul/well in 0.8×SSC buffer, 1% BSA).

The biodetectors were incubated for 1 h at RT. After washing three times with 200 ul of 0.8×SSC/Tw, 50 μl of biotinylated-DR5 DNA sequence (Biot-DR5, 5 pmol/well in 0.8×SSC/Tw buffer, 1% BSA) were added to the wells and plates were incubated for 1 h at RT. After washing three times with 0.8×SSC/Tw, each well was incubated with Streptavidin-HRP conjugated diluted 1:3,000 in 0.8×SSC/Tw containing 1% BSA. Plates were then washed three times with 0.8×SSC/Tw and 100 ul of TMB (Thermo Scientific) was added and incubated for 5-20 min. The reaction was stopped by adding 100 ul of 2 M $H_2SO_4$ and the optical density (O.D.) was read at the wavelength of 450 nm.

Protocol 14: Cell Culture and Preparation of Fixed Cells

Plate out cells at a density of $1\times10^5$ in 500 ul media on 13 mm coverslips in a four well plate and allow them to adhere overnight. Once the cells have attached, rinse twice with PBS, starve them in the appropriate medium without FBS for 2 h at 37° C. or in medium containing 0.1% FBS for 16 hours and then stimulate with untagged EGF or fluorescently-tagged EGF (70 nM), for the desired time. Wash cells twice with PBS and fix them in 4% Paraformaldehyde for 20 minutes at RT. After three additional washes with PBS, fixed cells can be stored in IFF medium (1% BSA, 2% FBS in PBS) at 4° C. and kept in the dark when necessary.

Protocol 15: Coincidence Detection in Fixed Cells

Permeabilise cells in 0.2% Triton X-100 in 0.8× Sodium Citrate buffer (0.8×SSC: 120 mM NaCl, 12 mM Sodium Citrate) for 5 minutes, wash three times with 0.8×SSC buffer containing 0.1% Tween 20 (0.8×SSC/Tw) and block in 5% BSA, 50 ng/μl RNase A, 10 pmol/μl Poly(dT), in 0.8×SSC/Tw buffer for 30 min at 37° C. Cell fixation, permeabilisation and antigen retrieval conditions should be optimised, if necessary, accordingly to standard laboratory procedures; 100 μl of reagent per 13 mm coverslip is recommended or use volumes corresponding to your delimited reaction area. Afterwards, dilute the detectors to suitable concentrations in 0.8×SSC, 1% BSA (recommended starting concentration is 2 pmol/coverslip). Rinse coverslips once with 0.8×SSC/Tw and immediately add the biodetectors solution. Incubate for 1 h at RT. Do not allow the samples to dry as this will cause background. The conditions for the biodetectors may need to be optimised with respect to blocking solution, concentrations, temperature and incubation time.

It is important that all incubations are performed in a humid environment to prevent evaporation.

Example 7

A Distinct, Non-Coincidence Use of Oligonucleotide Capture for Biological Readouts An alternative and simple use of DNA BD biodetectors is to enhance readout sensitivity in fixed cells/tissue samples and/or in western blot analysis.

In this example, the recognition domain may be phospho-specific SH2 domains/DARPins/scFvs.

These may be fused in frame with a DNA BD which is able to bind in a specific manner to a DNA sequence without the necessity of coincidence DNA recognition.

In another embodiment the recognition domain may be protein G and the fusion protein is therefore a Protein G-DNA BD fusion detector reagent.

In this example the cognate DNA sequence will contain a suitable flanking region that can be specifically amplified using rolling circle amplification reaction (RCA). The amplified DNA can be visualised with fluorescently (or other) labelled oligonucleotide probes as previously described.

An example of oligonucleotide capture for high-sensitivity readout is shown in FIG. 14.

In this example the DNA binding domain is the zinc finger DNA BD of Zif268 (Sequence 23). This contains three zinc finger domains that bind the major groove in a simple tandem arrangement.

Furthermore, FIG. 6 step 7 can be considered an example of single capture (showing how to detect the total amount of the target protein).

Design, selection, in situ mutagenesis and testing of specificity are described in protocols 1-7.

Example 8

Coincidence Detection

We have fused PLCg-SH2 to the other element of the exemplified coincidence biodetector (RAR) and shown that this modular fusion protein (RAR-PLCg-HA, Sequence 21) can also express well in bacteria, remain soluble and retain functionality (FIG. 16). A pull down assay shows that when Protein G is expressed in frame with RAR (RAR-Protein G, Sequence 22) the RAR-Protein G fusion retains functionality and binds specifically to antibodies. In our example RAR-Protein G is able to specifically pull down the F4 antibody (FIG. 17), which is an IgG1 mouse monoclonal raised against amino acids 985-996 of EGFR (Epidermal Growth Factor Receptor).

ELISA experiments (n=4, FIG. 18A) were carried out using RXR-Grb2 and RAR-PLCgN. Antibody-captured experiments show specificity and functionality for the detection modules RXR and RAR DBDs.

We have characterised the SH2 domain fusions from Grb2 and PLCgN as having robust interactions with their specific phospho-peptide (FIG. 19, Protocol 13). This involved bis-phosphotyrosine oligopeptides captured onto the wells instead of antibody-coated plates (FIG. 19B). Specificity (FIG. 19A) was determined by non-recognition of a non-specific bis-phosphorylated oligopeptide.

We have demonstrated functionality and specificity for coincidence readout using bis- and mono-phosphorylated oligopeptide-captured plates (FIG. 20 and FIG. 21, Protocol 13). FIG. 20 (n=5) displays the requirement of combined RXR/RAR detection reagents to obtain a signal compared to the use of either detection reagent alone. The specificity of epitope recognition was confirmed using specific versus non-specific bis-phosphorylated oligopeptides as epitope targets (FIG. 20A) and employing bis- and mono-phosphorylated oligopeptides as competitors (FIG. 21A).

The purified RXR-Grb2 and RAR-PLCgN reagents and the dataset generated provide a compelling demonstration of coincidence detection according to the present invention.

Example 9

Oligonucleotide Capture for Biological Readout

We provide examples of the use of the non-coincidence oligonucleotide capture for readout sensitisation. ELISA experiments were carried out to demonstrate the technology.

The technology is exemplified here with two examples, using i) the fusion reagent Zif268-EKElinker-ProteinG and ii) the fusion reagent Zif268-G/Slinker-ProteinG (Sequences 27 and 28).

Positive results were established by the strong signal-to-noise readout versus buffer alone when Zif268-EKElinker-ProteinG or Zif268-G/Slinker-ProteinG fusions were captured on an antibody-coated 96-well plate (FIG. 22A). The reagents were captured using an anti-EE antibody which recognises the EE-tag expressed at the C-terminus of the fusions; this allows testing of the functionality of the detection module Zif268 DBD without relying on any functionality of Protein G (FIG. 22B, Protocol 8).

ELISA experiments were then carried out using Zif268-EKElinker-ProteinG or Zif268-G/Slinker-ProteinG on an antibody-coated 96-well plate coated with the anti-F4 antibody (mouse monoclonal antibody raised against amino acids 985-996 of EGFR) (FIG. 23). Here, we have characterised the Protein G fusions as having a robust and specific interaction with the anti-F4 antibody thus, we have demonstrated them to be functional. Specificity of Protein G recognition was also confirmed by successfully competing away the signal using the anti-F4 antibody (FIG. 23).

Furthermore, the functionality and specificity of Zif268 DNA BD was established employing as a competitor the ds non-biotinylated Zif268 DNA sequence (ds NO BIO Zif268) (Sequence 29) recognized by Zif268 DNA BD. Excess of Zif268-DNA competitor in this assay successfully competed away the signal (FIG. 24). The experiments above, combined together, show that the two biodetectors are functional in all their parts. The purified Zif268-EKElinker-ProteinG and Zif268-G/Slinker-ProteinG reagents provide a compelling demonstration of oligonucleotide capture for readout sensitisation.

All publications mentioned in the above specification are herein incorporated by reference. Various modifications and variations of the described aspects and embodiments of the present invention will be apparent to those skilled in the art without departing from the scope of the present invention. Although the present invention has been described in connection with specific preferred embodiments, it should be understood that the invention as claimed should not be unduly limited to such specific embodiments. Indeed, various modifications of the described modes for carrying out the invention which are apparent to those skilled in the art are intended to be within the scope of the following claims.

The invention claimed is:

1. A method of detecting the coincidence of two biomolecular structures in a solid phase sample, said method comprising (i) providing a first and a second fusion protein, each fusion protein comprising (a) a detection domain, said detection domain comprising a DNA binding domain; said detection domain capable of binding a cognate specific nucleotide sequence in co-operation with a further detection domain;

(b) a recognition domain, said recognition domain capable of binding a target biomolecular structure; and (c) a connector domain; said connector domain being fused at one end to the detection domain and being fused at the other end to the recognition domain;

wherein at least two of (a), (b) and (c) are heterologous to one another;

wherein the recognition domains of said first and said second fusion proteins are capable of binding to first and second biomolecular structures;

(ii) contacting the sample with said first and second fusion proteins (iii) incubating to allow binding (iv) removing unbound fusion protein (v) contacting the sample with nucleic acid comprising said cognate specific nucleotide sequence (vi) incubating to allow heterotrimeric binding of the nucleic acid (vii) detecting nucleic acid bound to the sample wherein detection of nucleic acid in step (vii) indicates that the two biomolecular structures are present coincidentally in said sample.

2. A method according to claim 1 wherein the step of detecting nucleic acid bound to the sample comprises detection by total internal reflection (TIRF) analysis, by fluorescent polarisation (FP), by scintillation proximity technology or by fluorescence resonance energy transfer (FRET).

3. A method according to claim 1 wherein the step of detecting nucleic acid bound to the sample comprises (a) removing unbound nucleic acid; and (b) detecting nucleic acid bound to the sample.

4. A method according to claim 3 wherein detection of the nucleic acid bound to the sample is by polymerase chain reaction (PCR), by hybridisation to an oligonucleotide probe, by binding to a quantum dot nanocrystal, or by rolling circle amplification.

5. A method according to claim 1 wherein the sample is first contacted with an antibody capable of binding to a first molecular structure and wherein the recognition domain of one of said first or second fusion proteins is capable of binding to said antibody.

6. A method according to claim 5 wherein the recognition domain of said first or second fusion protein capable of binding to said antibody comprises amino acid sequence of an antigen binding fragment or scFv of a secondary antibody capable of binding to said antibody.

7. A method according to claim 5 wherein the recognition domain of said first or second fusion protein capable of binding to said antibody comprises amino acid sequence of protein A or protein G or protein L.

8. A method according to claim 1 wherein said DNA binding domain comprises amino acid sequence derived from a nuclear receptor and said specific nucleotide sequence comprises a hormone response element.

9. A method according to claim 1 wherein said connector domain comprises a flexible amino acid sequence of approximately 5 to 15 nm in length.

* * * * *

SEQUENCE LISTING

```
<160> NUMBER OF SEQ ID NOS: 81

<210> SEQ ID NO 1
<211> LENGTH: 318
<212> TYPE: DNA
<213> ORGANISM: Artificial Sequence
<220> FEATURE:
<223> OTHER INFORMATION: recombinant protein
<220> FEATURE:
<221> NAME/KEY: CDS
<222> LOCATION: (1)..(318)

<400> SEQUENCE: 1

ggt ggc ctg gaa gtt ctg ttc cag ggg ccc tcc ttc acc aag cac atc       48
Gly Gly Leu Glu Val Leu Phe Gln Gly Pro Ser Phe Thr Lys His Ile
1               5                   10                  15

tgc gcc atc tgc ggg gac cgc tcc tca ggc aag cac tat gga gtg tac       96
Cys Ala Ile Cys Gly Asp Arg Ser Ser Gly Lys His Tyr Gly Val Tyr
            20                  25                  30

agc tgc gag ggg tgc aag ggc ttc ttc aag cgg acg gtg cgc aag gac      144
Ser Cys Glu Gly Cys Lys Gly Phe Phe Lys Arg Thr Val Arg Lys Asp
        35                  40                  45

ctg acc tac acc tgc cgc gac aac aag gac tgc ctg att gac aag cgg      192
Leu Thr Tyr Thr Cys Arg Asp Asn Lys Asp Cys Leu Ile Asp Lys Arg
    50                  55                  60
```

-continued cag cgg aac cgg tgc cag tac tgc cgc tac cag aag tgc ctg gcc atg 240
Gln Arg Asn Arg Cys Gln Tyr Cys Arg Tyr Gln Lys Cys Leu Ala Met
65 70 75 80 ggc atg aag cgg gaa gcc gtg cag gag gag cgg cag cgt ggc aag gac 288
Gly Met Lys Arg Glu Ala Val Gln Glu Glu Arg Gln Arg Gly Lys Asp
85 90 95 cgg aac gag aat gag gtg gag tcg acc agc 318
Arg Asn Glu Asn Glu Val Glu Ser Thr Ser
100 105

<210> SEQ ID NO 2
<211> LENGTH: 106
<212> TYPE: PRT
<213> ORGANISM: Artificial Sequence
<220> FEATURE:
<223> OTHER INFORMATION: Synthetic Construct

<400> SEQUENCE: 2

Gly Gly Leu Glu Val Leu Phe Gln Gly Pro Ser Phe Thr Lys His Ile
1 5 10 15

Cys Ala Ile Cys Gly Asp Arg Ser Ser Gly Lys His Tyr Gly Val Tyr
20 25 30

Ser Cys Glu Gly Cys Lys Gly Phe Phe Lys Arg Thr Val Arg Lys Asp
35 40 45

Leu Thr Tyr Thr Cys Arg Asp Asn Lys Asp Cys Leu Ile Asp Lys Arg
50 55 60

Gln Arg Asn Arg Cys Gln Tyr Cys Arg Tyr Gln Lys Cys Leu Ala Met
65 70 75 80

Gly Met Lys Arg Glu Ala Val Gln Glu Glu Arg Gln Arg Gly Lys Asp
85 90 95

Arg Asn Glu Asn Glu Val Glu Ser Thr Ser
100 105

<210> SEQ ID NO 3
<211> LENGTH: 106
<212> TYPE: PRT
<213> ORGANISM: Artificial Sequence
<220> FEATURE:
<223> OTHER INFORMATION: Recombinant protein

<400> SEQUENCE: 3

Gly Gly Leu Glu Val Leu Phe Gln Gly Pro Ser Phe Thr Lys His Ile
1 5 10 15

Cys Ala Ile Cys Gly Asp Arg Ser Ser Gly Lys His Tyr Gly Val Tyr
20 25 30

Ser Cys Glu Gly Cys Lys Gly Phe Phe Lys Arg Thr Val Arg Lys Asp
35 40 45

Leu Thr Tyr Thr Cys Arg Asp Asn Lys Asp Cys Leu Ile Asp Lys Arg
50 55 60

Gln Arg Asn Arg Cys Gln Tyr Cys Arg Tyr Gln Lys Cys Leu Ala Met
65 70 75 80

Gly Met Lys Arg Glu Ala Val Gln Glu Glu Arg Gln Arg Gly Lys Asp
85 90 95

Arg Asn Glu Asn Glu Val Glu Ser Thr Ser
100 105

<210> SEQ ID NO 4
<211> LENGTH: 318
<212> TYPE: DNA
<213> ORGANISM: Artificial Sequence
<220> FEATURE:
<223> OTHER INFORMATION: Recombinant protein

<400> SEQUENCE: 4
ggtggcctgg aagttctgtt ccaggggccc ccccgcatct acaagccttg ctttgtctgt 60
caggacaagt cctcaggcta ccactatggg gtcagcgcct gtgagggctg caagggcttc 120
ttccgccgca gcatccagaa gaacatggtg tacacgtgtc accgggacaa gaactgcatc 180
atcaacaagg tgacccggaa ccgctgccag tactgccgac tgcagaagtg ctttgaagtg 240
ggcatgtcca aggagtctgt gagaaacgac cgaaacaaga agaagaagga ggtgcccaag 300
cccgagtgct ctgagagc 318

<210> SEQ ID NO 5
<211> LENGTH: 106
<212> TYPE: PRT
<213> ORGANISM: Artificial Sequence
<220> FEATURE:
<223> OTHER INFORMATION: Recombinant protein

<400> SEQUENCE: 5

Gly Gly Leu Glu Val Leu Phe Gln Gly Pro Pro Arg Ile Tyr Lys Pro
1 5 10 15

Cys Phe Val Cys Gln Asp Lys Ser Ser Gly Tyr His Tyr Gly Val Ser
20 25 30

Ala Cys Glu Gly Cys Lys Gly Phe Phe Arg Arg Ser Ile Gln Lys Asn
35 40 45

Met Val Tyr Thr Cys His Arg Asp Lys Asn Cys Ile Ile Asn Lys Val
50 55 60

Thr Arg Asn Arg Cys Gln Tyr Cys Arg Leu Gln Lys Cys Phe Glu Val
65 70 75 80

Gly Met Ser Lys Glu Ser Val Arg Asn Asp Arg Asn Lys Lys Lys Lys
85 90 95

Glu Val Pro Lys Pro Glu Cys Ser Glu Ser
100 105

<210> SEQ ID NO 6
<211> LENGTH: 93
<212> TYPE: PRT
<213> ORGANISM: Homo sapiens

<400> SEQUENCE: 6

Leu Asp Lys Asp Glu Leu Cys Val Val Cys Gly Asp Lys Ala Thr Gly
1 5 10 15

Tyr His Tyr Arg Cys Ile Thr Cys Glu Gly Cys Lys Gly Phe Phe Arg
20 25 30

Arg Thr Ile Gln Lys Asn Leu His Pro Ser Tyr Ser Cys Lys Tyr Glu
35 40 45

Gly Lys Cys Val Ile Asp Lys Val Thr Arg Asn Gln Cys Gln Glu Cys
50 55 60

Arg Phe Lys Lys Cys Ile Tyr Val Gly Met Ala Thr Asp Leu Val Leu
65 70 75 80

Asp Asp Ser Lys Arg Leu Ala Lys Arg Lys Leu Ile Glu
85 90

<210> SEQ ID NO 7
<211> LENGTH: 93
<212> TYPE: PRT
<213> ORGANISM: Homo sapiens

<400> SEQUENCE: 7

Arg Asn Val Pro Arg Ile Cys Gly Val Cys Gly Asp Arg Ala Thr Gly
1 5 10 15

Phe His Phe Asn Ala Met Thr Cys Glu Gly Cys Lys Gly Phe Phe Arg
20 25 30

Arg Ser Met Lys Arg Lys Ala Leu Phe Thr Cys Pro Phe Asn Gly Asp
35 40 45

Cys Arg Ile Thr Lys Asp Asn Arg Arg His Cys Gln Ala Cys Arg Leu
50 55 60

Lys Arg Cys Val Asp Ile Gly Met Met Lys Glu Phe Ile Leu Thr Asp
65 70 75 80

Glu Glu Val Gln Arg Lys Arg Glu Met Ile Leu Lys Arg
85 90

<210> SEQ ID NO 8
<211> LENGTH: 126
<212> TYPE: PRT
<213> ORGANISM: Saccharomyces cerevisiae

<400> SEQUENCE: 8

Met Asp Asp Ile Cys Ser Met Ala Glu Asn Ile Asn Arg Thr Leu Phe
1 5 10 15

Asn Ile Leu Gly Thr Glu Ile Asp Glu Ile Asn Leu Asn Thr Asn Asn
20 25 30

Leu Tyr Asn Phe Ile Met Glu Ser Asn Leu Thr Lys Val Glu Gln His
35 40 45

Thr Leu His Lys Asn Ile Ser Asn Asn Arg Leu Glu Ile Tyr His His
50 55 60

Ile Lys Lys Glu Lys Ser Pro Lys Gly Lys Ser Ser Ile Ser Pro Gln
65 70 75 80

Ala Arg Ala Phe Leu Glu Gln Val Phe Arg Arg Lys Gln Ser Leu Asn
85 90 95

Ser Lys Glu Lys Glu Glu Val Ala Lys Lys Cys Gly Ile Thr Pro Leu
100 105 110

Gln Val Arg Val Trp Phe Ile Asn Lys Arg Met Arg Ser Lys
115 120 125

<210> SEQ ID NO 9
<211> LENGTH: 210
<212> TYPE: PRT
<213> ORGANISM: Saccharomyces cerevisiae

<400> SEQUENCE: 9

Met Asn Lys Ile Pro Ile Lys Asp Leu Leu Asn Pro Gln Ile Thr Asp
1 5 10 15

Glu Phe Lys Ser Ser Ile Leu Asp Ile Asn Lys Lys Leu Phe Ser Ile
20 25 30

Cys Cys Asn Leu Pro Lys Leu Pro Glu Ser Val Thr Thr Glu Glu Glu
35 40 45

Val Glu Leu Arg Asp Ile Leu Gly Phe Leu Ser Arg Ala Asn Lys Asn
50 55 60

Arg Lys Ile Ser Asp Glu Glu Lys Lys Leu Leu Gln Thr Thr Ser Gln
65 70 75 80

Leu Thr Thr Thr Ile Thr Val Leu Leu Lys Glu Met Arg Ser Ile Glu
85 90 95

```
Asn Asp Arg Ser Asn Tyr Gln Leu Thr Gln Lys Asn Lys Ser Ala Asp
            100                 105                 110

Gly Leu Val Phe Asn Val Val Thr Gln Asp Met Ile Asn Lys Ser Thr
        115                 120                 125

Lys Pro Tyr Arg Gly His Arg Phe Thr Lys Glu Asn Val Arg Ile Leu
    130                 135                 140

Glu Ser Trp Phe Ala Lys Asn Ile Glu Asn Pro Tyr Leu Asp Thr Lys
145                 150                 155                 160

Gly Leu Glu Asn Leu Met Lys Asn Thr Ser Leu Ser Arg Ile Gln Ile
                165                 170                 175

Lys Asn Trp Val Ser Asn Arg Arg Arg Lys Glu Lys Thr Ile Thr Ile
            180                 185                 190

Ala Pro Glu Leu Ala Asp Leu Leu Ser Gly Glu Pro Leu Ala Lys Lys
        195                 200                 205

Lys Glu
210


<210> SEQ ID NO 10
<211> LENGTH: 106
<212> TYPE: PRT
<213> ORGANISM: Artificial Sequence
<220> FEATURE:
<223> OTHER INFORMATION: Recombinant protein

<400> SEQUENCE: 10

Gly Gly Leu Glu Val Leu Phe Gln Gly Pro Ser Phe Thr Lys His Ile
1               5                   10                  15

Cys Ala Ile Cys Gly Asp Arg Ser Ser Gly Lys His Tyr Gly Val Tyr
            20                  25                  30

Ser Cys Gly Ser Cys Lys Val Phe Phe Lys Arg Thr Val Arg Lys Asp
        35                  40                  45

Leu Thr Tyr Thr Cys Arg Asp Asn Lys Asp Cys Leu Ile Asp Lys Arg
    50                  55                  60

Gln Arg Asn Arg Cys Gln Tyr Cys Arg Tyr Gln Lys Cys Leu Ala Met
65                  70                  75                  80

Gly Met Lys Arg Glu Ala Val Gln Glu Glu Arg Gln Arg Gly Lys Asp
                85                  90                  95

Arg Asn Glu Asn Glu Val Glu Ser Thr Ser
            100                 105


<210> SEQ ID NO 11
<211> LENGTH: 106
<212> TYPE: PRT
<213> ORGANISM: Artificial Sequence
<220> FEATURE:
<223> OTHER INFORMATION: Recombinant protein

<400> SEQUENCE: 11

Gly Gly Leu Glu Val Leu Phe Gln Gly Pro Pro Arg Ile Tyr Lys Pro
1               5                   10                  15

Cys Phe Val Cys Gln Asp Lys Ser Ser Gly Tyr His Tyr Gly Val Ser
            20                  25                  30

Ala Cys Gly Ser Cys Lys Val Phe Phe Arg Arg Ser Ile Gln Lys Asn
        35                  40                  45

Met Val Tyr Thr Cys His Arg Asp Lys Asn Cys Ile Ile Asn Lys Val
    50                  55                  60

Thr Arg Asn Arg Cys Gln Tyr Cys Arg Leu Gln Lys Cys Phe Glu Val
65                  70                  75                  80
```

```
Gly Met Ser Lys Glu Ser Val Arg Asn Asp Arg Asn Lys Lys Lys Lys
                85                  90                  95

Glu Val Pro Lys Pro Glu Cys Ser Glu Ser
            100                 105


<210> SEQ ID NO 12
<211> LENGTH: 47
<212> TYPE: DNA
<213> ORGANISM: Artificial Sequence
<220> FEATURE:
<223> OTHER INFORMATION: DNA Probe
<220> FEATURE:
<221> NAME/KEY: misc_feature
<223> OTHER INFORMATION: Biotinylated

<400> SEQUENCE: 12

tggtatctag ttattgctca gcgtgccagg tcaccgaaag gtcagag                   47


<210> SEQ ID NO 13
<211> LENGTH: 45
<212> TYPE: DNA
<213> ORGANISM: Artificial Sequence
<220> FEATURE:
<223> OTHER INFORMATION: DNA Probe
<220> FEATURE:
<221> NAME/KEY: misc_feature
<222> LOCATION: (1)..(1)
<223> OTHER INFORMATION: Biotinylated

<400> SEQUENCE: 13

tgcgtctatt tagtggagcc ttgccaggtc accgaaaggt cagag                     45


<210> SEQ ID NO 14
<211> LENGTH: 45
<212> TYPE: DNA
<213> ORGANISM: Artificial Sequence
<220> FEATURE:
<223> OTHER INFORMATION: DNA Probe
<220> FEATURE:
<221> NAME/KEY: misc_feature
<222> LOCATION: (1)..(1)
<223> OTHER INFORMATION: Biotinylated

<400> SEQUENCE: 14

gcccgctgta aacatagaca ttgccagaac accgaaagaa cagag                     45


<210> SEQ ID NO 15
<211> LENGTH: 44
<212> TYPE: DNA
<213> ORGANISM: Artificial Sequence
<220> FEATURE:
<223> OTHER INFORMATION: DNA Probe
<220> FEATURE:
<221> NAME/KEY: misc_feature
<222> LOCATION: (1)..(1)
<223> OTHER INFORMATION: Biotinylated

<400> SEQUENCE: 15

gcccgctgta aacatagaca ttgccaggtc accgaaggtc agag                      44


<210> SEQ ID NO 16
<211> LENGTH: 43
<212> TYPE: DNA
<213> ORGANISM: Artificial Sequence
<220> FEATURE:
<223> OTHER INFORMATION: DNA Probe
<220> FEATURE:
<221> NAME/KEY: misc_feature
```

<222> LOCATION: (1)..(1)
<223> OTHER INFORMATION: Biotinylated

<400> SEQUENCE: 16
gcccgctgta aacatagaca ttgccaggtc accgaggtca gag 43

<210> SEQ ID NO 17
<211> LENGTH: 45
<212> TYPE: DNA
<213> ORGANISM: Artificial Sequence
<220> FEATURE:
<223> OTHER INFORMATION: DNA Probe
<220> FEATURE:
<221> NAME/KEY: misc_feature
<222> LOCATION: (1)..(1)
<223> OTHER INFORMATION: Biotinylated

<400> SEQUENCE: 17
tgcgtctatt tagtggagcc tttacatgta aaaatttaca tcata 45

<210> SEQ ID NO 18
<211> LENGTH: 24
<212> TYPE: DNA
<213> ORGANISM: Artificial Sequence
<220> FEATURE:
<223> OTHER INFORMATION: DNA Probe
<220> FEATURE:
<221> NAME/KEY: misc_signal
<222> LOCATION: (1)..(1)
<223> OTHER INFORMATION: Cyanine Cy3

<400> SEQUENCE: 18
tggtatctag ttattgctca gcgt 24

<210> SEQ ID NO 19
<211> LENGTH: 47
<212> TYPE: DNA
<213> ORGANISM: Artificial Sequence
<220> FEATURE:
<223> OTHER INFORMATION: DNA Probe
<220> FEATURE:
<221> NAME/KEY: misc_signal
<222> LOCATION: (1)..(1)
<223> OTHER INFORMATION: Cyanine Cy3

<400> SEQUENCE: 19
tggtatctag ttattgctca gcgtgccagg tcaccgaaag gtcagag 47

<210> SEQ ID NO 20
<211> LENGTH: 20
<212> TYPE: DNA
<213> ORGANISM: Artificial Sequence
<220> FEATURE:
<223> OTHER INFORMATION: DNA Probe
<220> FEATURE:
<221> NAME/KEY: misc_signal
<222> LOCATION: (1)..(1)
<223> OTHER INFORMATION: Cyanine Cy3

<400> SEQUENCE: 20
tgcgtctatt tagtggagcc 20

<210> SEQ ID NO 21
<211> LENGTH: 45
<212> TYPE: DNA
<213> ORGANISM: Artificial Sequence
<220> FEATURE:
<223> OTHER INFORMATION: DNA Probe
<220> FEATURE:

<221> NAME/KEY: misc_signal
<222> LOCATION: (1)..(1)
<223> OTHER INFORMATION: Cyanine Cy3

<400> SEQUENCE: 21
tgcgtctatt tagtggagcc ttgccaggtc accgaaaggt cagag 45

<210> SEQ ID NO 22
<211> LENGTH: 20
<212> TYPE: DNA
<213> ORGANISM: Artificial Sequence
<220> FEATURE:
<223> OTHER INFORMATION: DNA Probe
<220> FEATURE:
<221> NAME/KEY: misc_signal
<222> LOCATION: (1)..(1)
<223> OTHER INFORMATION: Cyanine Cy3

<400> SEQUENCE: 22
gcccgctgta aacatagaca 20

<210> SEQ ID NO 23
<211> LENGTH: 45
<212> TYPE: DNA
<213> ORGANISM: Artificial Sequence
<220> FEATURE:
<223> OTHER INFORMATION: DNA Probe
<220> FEATURE:
<221> NAME/KEY: misc_signal
<222> LOCATION: (1)..(1)
<223> OTHER INFORMATION: Cyanine Cy3

<400> SEQUENCE: 23
gcccgctgta aacatagaca ttgccagaac accgaaagaa cagag 45

<210> SEQ ID NO 24
<211> LENGTH: 20
<212> TYPE: DNA
<213> ORGANISM: Artificial Sequence
<220> FEATURE:
<223> OTHER INFORMATION: DNA Probe
<220> FEATURE:
<221> NAME/KEY: misc_signal
<222> LOCATION: (1)..(1)
<223> OTHER INFORMATION: Cyanine Cy3

<400> SEQUENCE: 24
gcccgctgta aacatagaca 20

<210> SEQ ID NO 25
<211> LENGTH: 44
<212> TYPE: DNA
<213> ORGANISM: Artificial Sequence
<220> FEATURE:
<223> OTHER INFORMATION: DNA Probe
<220> FEATURE:
<221> NAME/KEY: misc_signal
<222> LOCATION: (1)..(1)
<223> OTHER INFORMATION: Cyanine Cy3

<400> SEQUENCE: 25
gcccgctgta aacatagaca ttgccaggtc accgaaggtc agag 44

<210> SEQ ID NO 26
<211> LENGTH: 20
<212> TYPE: DNA
<213> ORGANISM: Artificial Sequence
<220> FEATURE:
<223> OTHER INFORMATION: DNA Probe

```
<220> FEATURE:
<221> NAME/KEY: misc_signal
<222> LOCATION: (1)..(1)
<223> OTHER INFORMATION: Cyanine Cy3

<400> SEQUENCE: 26

gcccgctgta aacatagaca                                               20


<210> SEQ ID NO 27
<211> LENGTH: 43
<212> TYPE: DNA
<213> ORGANISM: Artificial Sequence
<220> FEATURE:
<223> OTHER INFORMATION: DNA Probe
<220> FEATURE:
<221> NAME/KEY: misc_signal
<222> LOCATION: (1)..(1)
<223> OTHER INFORMATION: Cyanine Cy3

<400> SEQUENCE: 27

gcccgctgta aacatagaca ttgccaggtc accgaggtca gag                     43


<210> SEQ ID NO 28
<211> LENGTH: 22
<212> TYPE: DNA
<213> ORGANISM: Artificial Sequence
<220> FEATURE:
<223> OTHER INFORMATION: DNA Probe
<220> FEATURE:
<221> NAME/KEY: misc_signal
<222> LOCATION: (1)..(1)
<223> OTHER INFORMATION: Cyanine Cy3

<400> SEQUENCE: 28

tgcgtctatt tagtggagcc tt                                            22


<210> SEQ ID NO 29
<211> LENGTH: 45
<212> TYPE: DNA
<213> ORGANISM: Artificial Sequence
<220> FEATURE:
<223> OTHER INFORMATION: DNA Probe
<220> FEATURE:
<221> NAME/KEY: misc_signal
<222> LOCATION: (1)..(1)
<223> OTHER INFORMATION: Cyanine Cy3

<400> SEQUENCE: 29

tgcgtctatt tagtggagcc tttacatgta aaaatttaca tcata                   45


<210> SEQ ID NO 30
<211> LENGTH: 72
<212> TYPE: DNA
<213> ORGANISM: Artificial Sequence
<220> FEATURE:
<223> OTHER INFORMATION: RCA circular ssDNA

<400> SEQUENCE: 30

actcatgtat ccttttgcgt ctatttagtg gagccttttg cgtctattta gtggagcctt   60

tccagtgctt gt                                                       72


<210> SEQ ID NO 31
<211> LENGTH: 72
<212> TYPE: DNA
<213> ORGANISM: Artificial Sequence
<220> FEATURE:
<223> OTHER INFORMATION: RCA circular ssDNA
```

<400> SEQUENCE: 31
actcatgtat cctttgcccg ctgtaaacat agacatttgc ccgctgtaaa catagacatt 60
tccagtgctt gt 72

<210> SEQ ID NO 32
<211> LENGTH: 84
<212> TYPE: DNA
<213> ORGANISM: Artificial Sequence
<220> FEATURE:
<223> OTHER INFORMATION: Linker + MultiSite Gateway flanking sequences

<400> SEQUENCE: 32
gcaagtttgt acaaaaaagc aggctccggt ggcggccagc ttggcggtag ctcgagcaac 60
ccagctttct tgtacaaagt gggt 84

<210> SEQ ID NO 33
<211> LENGTH: 28
<212> TYPE: PRT
<213> ORGANISM: Artificial Sequence
<220> FEATURE:
<223> OTHER INFORMATION: Linker + MultiSite Gateway flanking sequences

<400> SEQUENCE: 33

```
Ala Ser Leu Tyr Lys Lys Ala Gly Ser Gly Gly Gly Gln Leu Gly Gly
1               5                   10                  15

Ser Ser Ser Asn Pro Ala Phe Leu Tyr Lys Val Gly
            20                  25
```

<210> SEQ ID NO 34
<211> LENGTH: 141
<212> TYPE: DNA
<213> ORGANISM: Artificial Sequence
<220> FEATURE:
<223> OTHER INFORMATION: Linker + MultiSite Gateway flanking sequences

<400> SEQUENCE: 34
gcaagtttgt acaaaaaagc aggctccggc ggtggtggcg agatcgctgc actggagaag 60
gagattgccg ctctggaaaa ggagatcgcg gcactggaga agggtggtgg cgggtaccca 120
gctttcttgt acaaagtggg t 141

<210> SEQ ID NO 35
<211> LENGTH: 47
<212> TYPE: PRT
<213> ORGANISM: Artificial Sequence
<220> FEATURE:
<223> OTHER INFORMATION: Recombinant protein

<400> SEQUENCE: 35

```
Ala Ser Leu Tyr Lys Lys Ala Gly Ser Gly Gly Gly Gly Glu Ile Ala
1               5                   10                  15

Ala Leu Glu Lys Glu Ile Ala Ala Leu Glu Lys Glu Ile Ala Ala Leu
            20                  25                  30

Glu Lys Gly Gly Gly Gly Tyr Pro Ala Phe Leu Tyr Lys Val Gly
        35                  40                  45
```

<210> SEQ ID NO 36
<211> LENGTH: 138
<212> TYPE: DNA
<213> ORGANISM: Artificial Sequence
<220> FEATURE:
<223> OTHER INFORMATION: Linker + MultiSite Gateway flanking sequences

<400> SEQUENCE: 36
gcaagtttgt acaaaaaagc aggctccggc ggtggtggca agatcgctgc actgaaggag 60
aaaattgccg ctctgaaaga gaagatcgct gccctgaagg aaggtggtgg cgggtaccca 120
gctttcttgt acaaagtg 138

<210> SEQ ID NO 37
<211> LENGTH: 46
<212> TYPE: PRT
<213> ORGANISM: Artificial Sequence
<220> FEATURE:
<223> OTHER INFORMATION: Linker + MultiSite Gateway flanking sequences

<400> SEQUENCE: 37

Ala Ser Leu Tyr Lys Lys Ala Gly Ser Gly Gly Gly Gly Lys Ile Ala
1 5 10 15

Ala Leu Lys Glu Lys Ile Ala Ala Leu Lys Glu Lys Ile Ala Ala Leu
20 25 30

Lys Glu Gly Gly Gly Gly Tyr Pro Ala Phe Leu Tyr Lys Val
35 40 45

<210> SEQ ID NO 38
<211> LENGTH: 213
<212> TYPE: DNA
<213> ORGANISM: Artificial Sequence
<220> FEATURE:
<223> OTHER INFORMATION: Linker + MultiSite Gateway flanking sequences

<400> SEQUENCE: 38
gcaagtttgt acaaaaaagc aggctccggt ggcggccgca aaaaaaaaca gcaggaagag 60
gaagcagaac gtctgcgtcg tattcaagaa gaaatggaaa aggaacgcaa acgccgtgaa 120
gaagacgaaa aacgtcgccg caaggaagag gaggaacgtc gtatgaagct tggcggtagc 180
tcgagcaacc cagctttctt gtacaaagtg ggt 213

<210> SEQ ID NO 39
<211> LENGTH: 71
<212> TYPE: PRT
<213> ORGANISM: Artificial Sequence
<220> FEATURE:
<223> OTHER INFORMATION: Linker + MultiSite Gateway flanking sequences

<400> SEQUENCE: 39

Ala Ser Leu Tyr Lys Lys Ala Gly Ser Gly Gly Gly Arg Lys Lys Lys
1 5 10 15

Gln Gln Glu Glu Glu Ala Glu Arg Leu Arg Arg Ile Gln Glu Glu Met
20 25 30

Glu Lys Glu Arg Lys Arg Arg Glu Glu Asp Glu Lys Arg Arg Arg Lys
35 40 45

Glu Glu Glu Glu Arg Arg Met Lys Leu Gly Gly Ser Ser Ser Asn Pro
50 55 60

Ala Phe Leu Tyr Lys Val Gly
65 70

<210> SEQ ID NO 40
<211> LENGTH: 1236
<212> TYPE: DNA
<213> ORGANISM: Artificial Sequence
<220> FEATURE:
<223> OTHER INFORMATION: Recombinant protein

<400> SEQUENCE: 40

-continued

```
atgtcccta tactaggtta ttggaaaatt aagggccttg tgcaacccac tcgacttctt     60

ttggaatatc ttgaagaaaa atatgaagag catttgtatg agcgcgatga aggtgataaa    120

tggcgaaaca aaaagtttga attgggtttg gagtttccca atcttcctta ttatattgat    180

ggtgatgtta aattaacaca gtctatggcc atcatacgtt atatagctga caagcacaac    240

atgttgggtg gttgtccaaa agagcgtgca gagatttcaa tgcttgaagg agcggttttg    300

gatattagat acggtgtttc gagaattgca tatagtaaag actttgaaac tctcaaagtt    360

gattttctta gcaagctacc tgaaatgctg aaaatgttcg aagatcgttt atgtcataaa    420

acatatttaa atggtgatca tgtaacccat cctgacttca tgttgtatga cgctcttgat    480

gttgttttat acatggaccc aatgtgcctg gatgcgttcc caaaattagt ttgttttaaa    540

aaacgtattg aagctatccc acaaattgat aagtacttga aatccagcaa gtatatagca    600

tggcctttgc agggctggca agccacgttt ggtggtggcg accatcctcc aaaatcggat    660

ctggttccgc gtggatcccc ggaattccca ggaaacagct atgaccatga ttacgccaag    720

ctatcaactt tgtatagaaa agttggtggt ggcctggaag ttctgttcca ggggccctcc    780

ttcaccaagc acatctgcgc catctgcggg gaccgctcct caggcaagca ctatggagtg    840

tacagctgcg aggggtgcaa gggcttcttc aagcggacgg tgcgcaagga cctgacctac    900

acctgccgcg acaacaagga ctgcctgatt gacaagcggc agcggaaccg gtgccagtac    960

tgccgctacc agaagtgcct ggccatgggc atgaagcggg aagccgtgca ggaggagcgg   1020

cagcgtggca aggaccggaa cgagaatgag gtggagtcga ccagcgcaag tttgtacaaa   1080

aaagcaggct ccggcggtgg tggcgagatc gctgcactgg agaaggagat tgccgctctg   1140

gaaaaggaga tcgcggcact ggagaagggt ggtggcgggt acccagcttt cttgtacaaa   1200

gtggaacaaa aactcatctc agaagaggat ctgtaa                              1236
```

```
<210> SEQ ID NO 41
<211> LENGTH: 411
<212> TYPE: PRT
<213> ORGANISM: Artificial Sequence
<220> FEATURE:
<223> OTHER INFORMATION: Recombinant protein

<400> SEQUENCE: 41

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140
```

-continued

```
Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Val Pro Arg
    210                 215                 220

Gly Ser Pro Glu Phe Pro Gly Asn Ser Tyr Asp His Asp Tyr Ala Lys
225                 230                 235                 240

Leu Ser Thr Leu Tyr Arg Lys Val Gly Gly Gly Leu Glu Val Leu Phe
                245                 250                 255

Gln Gly Pro Ser Phe Thr Lys His Ile Cys Ala Ile Cys Gly Asp Arg
            260                 265                 270

Ser Ser Gly Lys His Tyr Gly Val Tyr Ser Cys Glu Gly Cys Lys Gly
        275                 280                 285

Phe Phe Lys Arg Thr Val Arg Lys Asp Leu Thr Tyr Thr Cys Arg Asp
    290                 295                 300

Asn Lys Asp Cys Leu Ile Asp Lys Arg Gln Arg Asn Arg Cys Gln Tyr
305                 310                 315                 320

Cys Arg Tyr Gln Lys Cys Leu Ala Met Gly Met Lys Arg Glu Ala Val
                325                 330                 335

Gln Glu Glu Arg Gln Arg Gly Lys Asp Arg Asn Glu Asn Glu Val Glu
            340                 345                 350

Ser Thr Ser Ala Ser Leu Tyr Lys Lys Ala Gly Ser Gly Gly Gly Gly
        355                 360                 365

Glu Ile Ala Ala Leu Glu Lys Glu Ile Ala Ala Leu Glu Lys Glu Ile
    370                 375                 380

Ala Ala Leu Glu Lys Gly Gly Gly Gly Tyr Pro Ala Phe Leu Tyr Lys
385                 390                 395                 400

Val Glu Gln Lys Leu Ile Ser Glu Glu Asp Leu
                405                 410
```

<210> SEQ ID NO 42
<211> LENGTH: 1287
<212> TYPE: DNA
<213> ORGANISM: Artificial Sequence
<220> FEATURE:
<223> OTHER INFORMATION: Recombinant protein

<400> SEQUENCE: 42

```
atgtccccta tactaggtta ttggaaaatt aagggccttg tgcaacccac tcgacttctt      60

ttggaatatc ttgaagaaaa atatgaagag catttgtatg agcgcgatga aggtgataaa     120

tggcgaaaca aaaagtttga attgggtttg gagtttccca atcttcctta ttatattgat     180

ggtgatgtta aattaacaca gtctatggcc atcatacgtt atatagctga caagcacaac     240

atgttgggtg gttgtccaaa agagcgtgca gagatttcaa tgcttgaagg agcggttttg     300

gatattagat acggtgtttc gagaattgca tatagtaaag actttgaaac tctcaaagtt     360

gattttctta gcaagctacc tgaaatgctg aaaatgttcg aagatcgttt atgtcataaa     420

acatatttaa atggtgatca tgtaacccat cctgacttca tgttgtatga cgctcttgat     480

gttgttttat acatggaccc aatgtgcctg gatgcgttcc caaaattagt ttgttttaaa     540
```

```
aaacgtattg aagctatccc acaaattgat aagtacttga aatccagcaa gtatatagca    600

tggcctttgc agggctggca agccacgttt ggtggtggcg accatcctcc aaaatcggat    660

ctggttccgc gtggatcccc ggaattccca ggaaacagct atgaccatga ttacgccaag    720

ctatcaactt tgtatagaaa agttggtggt ggcctggaag ttctgttcca ggggcccccc    780

cgcatctaca agccttgctt tgtctgtcag gacaagtcct caggctacca ctatggggtc    840

agcgcctgtg agggctgcaa gggcttcttc cgccgcagca tccagaagaa catggtgtac    900

acgtgtcacc gggacaagaa ctgcatcatc aacaaggtga cccggaaccg ctgccagtac    960

tgccgactgc agaagtgctt tgaagtgggc atgtccaagg agtctgtgag aaacgaccga   1020

aacaagaaga agaaggaggt gcccaagccc gagtgctctg agagcgcaag tttgtacaaa   1080

aaagcaggct ccggcggtgg tggcaagatc gctgcactga aggagaaaat tgccgctctg   1140

aaagagaaga tcgctgccct gaaggaaggt ggtggcgggt acccagcttt cttgtacaaa   1200

gtgggtatga aagaaaccgc tgctgctaaa ttcgaacgcc agcacatgga cagcccagat   1260

ctgggtgagt atatgccgat ggaataa                                      1287
```

```
<210> SEQ ID NO 43
<211> LENGTH: 428
<212> TYPE: PRT
<213> ORGANISM: Artificial Sequence
<220> FEATURE:
<223> OTHER INFORMATION: Recombinant protein

<400> SEQUENCE: 43

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Val Pro Arg
    210                 215                 220
```

```
Gly Ser Pro Glu Phe Pro Gly Asn Ser Tyr Asp His Asp Tyr Ala Lys
225                 230                 235                 240

Leu Ser Thr Leu Tyr Arg Lys Val Gly Gly Gly Leu Glu Val Leu Phe
                245                 250                 255

Gln Gly Pro Pro Arg Ile Tyr Lys Pro Cys Phe Val Cys Gln Asp Lys
            260                 265                 270

Ser Ser Gly Tyr His Tyr Gly Val Ser Ala Cys Glu Gly Cys Lys Gly
        275                 280                 285

Phe Phe Arg Arg Ser Ile Gln Lys Asn Met Val Tyr Thr Cys His Arg
    290                 295                 300

Asp Lys Asn Cys Ile Ile Asn Lys Val Thr Arg Asn Arg Cys Gln Tyr
305                 310                 315                 320

Cys Arg Leu Gln Lys Cys Phe Glu Val Gly Met Ser Lys Glu Ser Val
                325                 330                 335

Arg Asn Asp Arg Asn Lys Lys Lys Lys Glu Val Pro Lys Pro Glu Cys
            340                 345                 350

Ser Glu Ser Ala Ser Leu Tyr Lys Lys Ala Gly Ser Gly Gly Gly Gly
        355                 360                 365

Lys Ile Ala Ala Leu Lys Glu Lys Ile Ala Ala Leu Lys Glu Lys Ile
    370                 375                 380

Ala Ala Leu Lys Glu Gly Gly Gly Gly Tyr Pro Ala Phe Leu Tyr Lys
385                 390                 395                 400

Val Gly Met Lys Glu Thr Ala Ala Ala Lys Phe Glu Arg Gln His Met
                405                 410                 415

Asp Ser Pro Asp Leu Gly Glu Tyr Met Pro Met Glu
            420                 425
```

<210> SEQ ID NO 44
<211> LENGTH: 417
<212> TYPE: DNA
<213> ORGANISM: Artificial Sequence
<220> FEATURE:
<223> OTHER INFORMATION: Recombinant protein

<400> SEQUENCE: 44

```
aagaactaca tagaaatgaa accacatccg tggtttttg gcaaaatccc cagagccaag     60

gcagaagaaa tgcttagcaa acagcggcac gatggggcct ttcttatccg agagagtgag    120

agcgctcctg ggacttctc cctctctgtc aagtttggaa acgatgtgca gcacttcaag    180

gtgctccgag atggagccgg gaagtacttc ctctgggtgg tgaagttcaa ttctttgaat    240

gagctggtgg attatcacag atctacatct gtctccagaa accagcagat attcctgcgg    300

gacatagaac aggtgccaca gcagccgaca tacgtccagg ccggtggtgg cgaacaaaaa    360

ctcatctcag aagaggatct gaatagcgcc gtcgaccacc accatcatca ccattaa       417
```

<210> SEQ ID NO 45
<211> LENGTH: 138
<212> TYPE: PRT
<213> ORGANISM: Artificial Sequence
<220> FEATURE:
<223> OTHER INFORMATION: Recombinant protein

<400> SEQUENCE: 45

```
Lys Asn Tyr Ile Glu Met Lys Pro His Pro Trp Phe Phe Gly Lys Ile
1               5                   10                  15

Pro Arg Ala Lys Ala Glu Glu Met Leu Ser Lys Gln Arg His Asp Gly
            20                  25                  30
```

-continued

```
Ala Phe Leu Ile Arg Glu Ser Glu Ser Ala Pro Gly Asp Phe Ser Leu
        35                  40                  45

Ser Val Lys Phe Gly Asn Asp Val Gln His Phe Lys Val Leu Arg Asp
    50                  55                  60

Gly Ala Gly Lys Tyr Phe Leu Trp Val Val Lys Phe Asn Ser Leu Asn
65                  70                  75                  80

Glu Leu Val Asp Tyr His Arg Ser Thr Ser Val Ser Arg Asn Gln Gln
                85                  90                  95

Ile Phe Leu Arg Asp Ile Glu Gln Val Pro Gln Gln Pro Thr Tyr Val
            100                 105                 110

Gln Ala Gly Gly Gly Glu Gln Lys Leu Ile Ser Glu Glu Asp Leu Asn
        115                 120                 125

Ser Ala Val Asp His His His His His His
    130                 135
```

<210> SEQ ID NO 46
<211> LENGTH: 447
<212> TYPE: DNA
<213> ORGANISM: Artificial Sequence
<220> FEATURE:
<223> OTHER INFORMATION: Recombinant protein

<400> SEQUENCE: 46

```
cactccaacg agaagtggtt ccacgggaag cttggggcgg gccgggatgg gcggcacatc     60

gccgagcgcc tgctcacgga gtactgcatt gagaccgggg cccccgacgg ctccttcctt    120

gtgcgcgaga gcgagacctt tgtgggcgac tacactctgt ccttctggcg gaatggcaaa    180

gtgcagcact gccggatcca ctcccggcag gacgcaggca cccccaagtt cttcctgacg    240

gacaacctcg tcttcgactc cctctatgac ctcatcacgc actaccagca ggtgcccctg    300

cgctgcaacg aatttgagat gcgcctctca gagccggtcc cgcagggtgg tggctaccca    360

tacgatgttc cagattacgc tcttggcggg tccgagtata tgccgatgga aaatagcgcc    420

gtcgaccacc accatcatca ccattaa                                        447
```

<210> SEQ ID NO 47
<211> LENGTH: 148
<212> TYPE: PRT
<213> ORGANISM: Artificial Sequence
<220> FEATURE:
<223> OTHER INFORMATION: Recombinant protein

<400> SEQUENCE: 47

```
His Ser Asn Glu Lys Trp Phe His Gly Lys Leu Gly Ala Gly Arg Asp
1               5                   10                  15

Gly Arg His Ile Ala Glu Arg Leu Leu Thr Glu Tyr Cys Ile Glu Thr
            20                  25                  30

Gly Ala Pro Asp Gly Ser Phe Leu Val Arg Glu Ser Glu Thr Phe Val
        35                  40                  45

Gly Asp Tyr Thr Leu Ser Phe Trp Arg Asn Gly Lys Val Gln His Cys
    50                  55                  60

Arg Ile His Ser Arg Gln Asp Ala Gly Thr Pro Lys Phe Phe Leu Thr
65                  70                  75                  80

Asp Asn Leu Val Phe Asp Ser Leu Tyr Asp Leu Ile Thr His Tyr Gln
                85                  90                  95

Gln Val Pro Leu Arg Cys Asn Glu Phe Glu Met Arg Leu Ser Glu Pro
            100                 105                 110

Val Pro Gln Gly Gly Gly Tyr Pro Tyr Asp Val Pro Asp Tyr Ala Leu
```

-continued

```
        115                 120                 125

Gly Gly Ser Glu Tyr Met Pro Met Glu Asn Ser Ala Val Asp His His
    130                 135                 140

His His His His
145
```

<210> SEQ ID NO 48
<211> LENGTH: 516
<212> TYPE: DNA
<213> ORGANISM: Artificial Sequence
<220> FEATURE:
<223> OTHER INFORMATION: Recombinant protein

<400> SEQUENCE: 48

```
ggctcgagca cctataagtt aatccttaac ggcaagacgt taaagggtga gaccaccacc      60

gaagctgttg atgctgctac cgcggagaag gtctttaagc agtatgcgaa tgataatggc     120

gtggacggcg aatggacgta cgacgacgcc accaaaacgt tcacagttac cgagaaacca     180

gaagtgatcg atgcgtctga attaacacca gccgtgacaa cttacaaact tgttattaat     240

ggtaaaacat tgaaaggcga aacaactact aaagcagtag acgcagaaac tgcagaaaaa     300

gccttcaaac aatacgctaa cgacaacggt gttgatggtg tttggactta tgatgatgcg     360

actaagacct ttacggtaac tgaaggtggt agcggcggcg gtatgaaaga aaccgctgct     420

gctaaattcg aacgccagca catggacagc ccagatctgg gtgagtatat gccgatggaa     480

aatagcgccg tcgaccacca ccatcatcac cattaa                              516
```

<210> SEQ ID NO 49
<211> LENGTH: 171
<212> TYPE: PRT
<213> ORGANISM: Artificial Sequence
<220> FEATURE:
<223> OTHER INFORMATION: Recombinant protein

<400> SEQUENCE: 49

```
Gly Ser Ser Thr Tyr Lys Leu Ile Leu Asn Gly Lys Thr Leu Lys Gly
1               5                   10                  15

Glu Thr Thr Thr Glu Ala Val Asp Ala Ala Thr Ala Glu Lys Val Phe
            20                  25                  30

Lys Gln Tyr Ala Asn Asp Asn Gly Val Asp Gly Glu Trp Thr Tyr Asp
        35                  40                  45

Asp Ala Thr Lys Thr Phe Thr Val Thr Glu Lys Pro Glu Val Ile Asp
    50                  55                  60

Ala Ser Glu Leu Thr Pro Ala Val Thr Thr Tyr Lys Leu Val Ile Asn
65                  70                  75                  80

Gly Lys Thr Leu Lys Gly Glu Thr Thr Thr Lys Ala Val Asp Ala Glu
                85                  90                  95

Thr Ala Glu Lys Ala Phe Lys Gln Tyr Ala Asn Asp Asn Gly Val Asp
            100                 105                 110

Gly Val Trp Thr Tyr Asp Asp Ala Thr Lys Thr Phe Thr Val Thr Glu
        115                 120                 125

Gly Gly Ser Gly Gly Gly Met Lys Glu Thr Ala Ala Ala Lys Phe Glu
    130                 135                 140

Arg Gln His Met Asp Ser Pro Asp Leu Gly Glu Tyr Met Pro Met Glu
145                 150                 155                 160

Asn Ser Ala Val Asp His His His His His His
                165                 170
```

<210> SEQ ID NO 50
<211> LENGTH: 1623
<212> TYPE: DNA
<213> ORGANISM: Artificial Sequence
<220> FEATURE:
<223> OTHER INFORMATION: Recombinant protein

<400> SEQUENCE: 50
atgtccccta tactaggtta ttggaaaatt aagggccttg tgcaacccac tcgacttctt 60
ttggaatatc ttgaagaaaa atatgaagag catttgtatg agcgcgatga aggtgataaa 120
tggcgaaaca aaaagtttga attgggtttg gagtttccca atcttcctta ttatattgat 180
ggtgatgtta aattaacaca gtctatggcc atcatacgtt atatagctga caagcacaac 240
atgttgggtg gttgtccaaa agagcgtgca gagatttcaa tgcttgaagg agcggttttg 300
gatattagat acggtgtttc gagaattgca tatagtaaag actttgaaac tctcaaagtt 360
gattttctta gcaagctacc tgaaatgctg aaaatgttcg aagatcgttt atgtcataaa 420
acatatttaa atggtgatca tgtaacccat cctgacttca tgttgtatga cgctcttgat 480
gttgttttat acatggaccc aatgtgcctg gatgcgttcc caaaattagt ttgttttaaa 540
aaacgtattg aagctatccc acaaattgat aagtacttga aatccagcaa gtatatagca 600
tggcctttgc agggctggca agccacgttt ggtggtggcg accatcctcc aaaatcggat 660
ctggttccgc gtggatcccc ggaattccca ggaaacagct atgaccatga ttacgccaag 720
ctatcaactt tgtatagaaa agttggtggt ggcctggaag ttctgttcca ggggccctcc 780
ttcaccaagc acatctgcgc catctgcggg gaccgctcct caggcaagca ctatggagtg 840
tacagctgcg aggggtgcaa gggcttcttc aagcggacgg tgcgcaagga cctgacctac 900
acctgccgcg acaacaagga ctgcctgatt gacaagcggc agcggaaccg gtgccagtac 960
tgccgctacc agaagtgcct ggccatgggc atgaagcggg aagccgtgca ggaggagcgg 1020
cagcgtggca aggaccggaa cgagaatgag gtggagtcga ccagcgcaag tttgtacaaa 1080
aaagcaggct ccggcggtgg tggcgagatc gctgcactgg agaaggagat tgccgctctg 1140
gaaaaggaga tcgcggcact ggagaagggt ggtggcgggt acccagcttt cttgtacaaa 1200
gtgggtaaga actacataga aatgaaacca catccgtggt tttttggcaa aatccccaga 1260
gccaaggcag aagaaatgct tagcaaacag cggcacgatg ggcctttcct tatccgagag 1320
agtgagagcg ctcctgggga cttctccctc tctgtcaagt ttggaaacga tgtgcagcac 1380
ttcaaggtgc tccgagatgg agccgggaag tacttcctct gggtggtgaa gttcaattct 1440
ttgaatgagc tggtggatta tcacagatct acatctgtct ccagaaacca gcagatattc 1500
ctgcgggaca tagaacaggt gccacagcag ccgacatacg tccaggccgg tggtggcgaa 1560
caaaaactca tctcagaaga ggatctgaat agcgccgtcg accaccacca tcatcaccat 1620
taa 1623

<210> SEQ ID NO 51
<211> LENGTH: 540
<212> TYPE: PRT
<213> ORGANISM: Artificial Sequence
<220> FEATURE:
<223> OTHER INFORMATION: Recombinant protein

<400> SEQUENCE: 51

Met Ser Pro Ile Leu Gly Tyr Trp Lys Ile Lys Gly Leu Val Gln Pro
1 5 10 15

-continued

Thr Arg Leu Leu Leu Glu Tyr Leu Glu Glu Lys Tyr Glu Glu His Leu
20 25 30

Tyr Glu Arg Asp Glu Gly Asp Lys Trp Arg Asn Lys Lys Phe Glu Leu
35 40 45

Gly Leu Glu Phe Pro Asn Leu Pro Tyr Tyr Ile Asp Gly Asp Val Lys
50 55 60

Leu Thr Gln Ser Met Ala Ile Ile Arg Tyr Ile Ala Asp Lys His Asn
65 70 75 80

Met Leu Gly Gly Cys Pro Lys Glu Arg Ala Glu Ile Ser Met Leu Glu
85 90 95

Gly Ala Val Leu Asp Ile Arg Tyr Gly Val Ser Arg Ile Ala Tyr Ser
100 105 110

Lys Asp Phe Glu Thr Leu Lys Val Asp Phe Leu Ser Lys Leu Pro Glu
115 120 125

Met Leu Lys Met Phe Glu Asp Arg Leu Cys His Lys Thr Tyr Leu Asn
130 135 140

Gly Asp His Val Thr His Pro Asp Phe Met Leu Tyr Asp Ala Leu Asp
145 150 155 160

Val Val Leu Tyr Met Asp Pro Met Cys Leu Asp Ala Phe Pro Lys Leu
165 170 175

Val Cys Phe Lys Lys Arg Ile Glu Ala Ile Pro Gln Ile Asp Lys Tyr
180 185 190

Leu Lys Ser Ser Lys Tyr Ile Ala Trp Pro Leu Gln Gly Trp Gln Ala
195 200 205

Thr Phe Gly Gly Gly Asp His Pro Pro Lys Ser Asp Leu Val Pro Arg
210 215 220

Gly Ser Pro Glu Phe Pro Gly Asn Ser Tyr Asp His Asp Tyr Ala Lys
225 230 235 240

Leu Ser Thr Leu Tyr Arg Lys Val Gly Gly Gly Leu Glu Val Leu Phe
245 250 255

Gln Gly Pro Ser Phe Thr Lys His Ile Cys Ala Ile Cys Gly Asp Arg
260 265 270

Ser Ser Gly Lys His Tyr Gly Val Tyr Ser Cys Glu Gly Cys Lys Gly
275 280 285

Phe Phe Lys Arg Thr Val Arg Lys Asp Leu Thr Tyr Thr Cys Arg Asp
290 295 300

Asn Lys Asp Cys Leu Ile Asp Lys Arg Gln Arg Asn Arg Cys Gln Tyr
305 310 315 320

Cys Arg Tyr Gln Lys Cys Leu Ala Met Gly Met Lys Arg Glu Ala Val
325 330 335

Gln Glu Glu Arg Gln Arg Gly Lys Asp Arg Asn Glu Asn Glu Val Glu
340 345 350

Ser Thr Ser Ala Ser Leu Tyr Lys Lys Ala Gly Ser Gly Gly Gly Gly
355 360 365

Glu Ile Ala Ala Leu Glu Lys Glu Ile Ala Ala Leu Glu Lys Glu Ile
370 375 380

Ala Ala Leu Glu Lys Gly Gly Gly Gly Tyr Pro Ala Phe Leu Tyr Lys
385 390 395 400

Val Gly Lys Asn Tyr Ile Glu Met Lys Pro His Pro Trp Phe Phe Gly
405 410 415

Lys Ile Pro Arg Ala Lys Ala Glu Glu Met Leu Ser Lys Gln Arg His
420 425 430

Asp Gly Ala Phe Leu Ile Arg Glu Ser Glu Ser Ala Pro Gly Asp Phe

```
        435                 440                 445

Ser Leu Ser Val Lys Phe Gly Asn Asp Val Gln His Phe Lys Val Leu
    450                 455                 460

Arg Asp Gly Ala Gly Lys Tyr Phe Leu Trp Val Val Lys Phe Asn Ser
465                 470                 475                 480

Leu Asn Glu Leu Val Asp Tyr His Arg Ser Thr Ser Val Ser Arg Asn
                485                 490                 495

Gln Gln Ile Phe Leu Arg Asp Ile Glu Gln Val Pro Gln Gln Pro Thr
            500                 505                 510

Tyr Val Gln Ala Gly Gly Gly Glu Gln Lys Leu Ile Ser Glu Glu Asp
        515                 520                 525

Leu Asn Ser Ala Val Asp His His His His His His
    530                 535                 540
```

<210> SEQ ID NO 52
<211> LENGTH: 1596
<212> TYPE: DNA
<213> ORGANISM: Artificial Sequence
<220> FEATURE:
<223> OTHER INFORMATION: Recombinant protein

<400> SEQUENCE: 52

```
atgtccccta tactaggtta ttggaaaatt aagggccttg tgcaacccac tcgacttctt     60

ttggaatatc ttgaagaaaa atatgaagag catttgtatg agcgcgatga aggtgataaa    120

tggcgaaaca aaaagtttga attgggtttg gagtttccca atcttcctta ttatattgat    180

ggtgatgtta aattaacaca gtctatggcc atcatacgtt atatagctga caagcacaac    240

atgttgggtg gttgtccaaa agagcgtgca gagatttcaa tgcttgaagg agcggttttg    300

gatattagat acggtgtttc gagaattgca tatagtaaag actttgaaac tctcaaagtt    360

gattttctta gcaagctacc tgaaatgctg aaaatgttcg aagatcgttt atgtcataaa    420

acatatttaa atggtgatca tgtaacccat cctgacttca tgttgtatga cgctcttgat    480

gttgttttat acatggaccc aatgtgcctg gatgcgttcc caaaattagt ttgttttaaa    540

aaacgtattg aagctatccc acaaattgat aagtacttga aatccagcaa gtatatagca    600

tggcctttgc agggctggca agccacgttt ggtggtggcg accatcctcc aaaatcggat    660

ctggttccgc gtggatcccc ggaattccca ggaaacagct atgaccatga ttacgccaag    720

ctatcaactt tgtatagaaa agttggtggt ggcctggaag ttctgttcca ggggcccccc    780

cgcatctaca agccttgctt tgtctgtcag gacaagtcct caggctacca ctatggggtc    840

agcgcctgtg agggctgcaa gggcttcttc cgccgcagca tccagaagaa catggtgtac    900

acgtgtcacc gggacaagaa ctgcatcatc aacaaggtga cccggaaccg ctgccagtac    960

tgccgactgc agaagtgctt tgaagtgggc atgtccaagg agtctgtgag aaacgaccga   1020

aacaagaaga agaaggaggt gcccaagccc gagtgctctg agagcgcaag tttgtacaaa   1080

aaagcaggct ccggtggcgg ccagcttggc ggtagctcga gcaacccagc tttcttgtac   1140

aaagtgggtc actccaacga gaagtggttc cacgggaagc ttggggcggg ccgggatggg   1200

cggcacatcg ccgagcgcct gctcacggag tactgcattg agaccggggc ccccgacggc   1260

tccttccttg tgcgcgagag cgagaccttt gtgggcgact acactctgtc cttctggcgg   1320

aatggcaaag tgcagcactg ccggatccac tcccggcagg acgcaggcac ccccaagttc   1380

ttcctgacgg acaacctcgt cttcgactcc ctctatgacc tcatcacgca ctaccagcag   1440

gtgcccctgc gctgcaacga atttgagatg cgcctctcag agccggtccc gcagggtggt   1500
```

-continued

```
ggctacccat acgatgttcc agattacgct cttggcgggt ccgagtatat gccgatggaa   1560

aatagcgccg tcgaccacca ccatcatcac cattaa                             1596


<210> SEQ ID NO 53
<211> LENGTH: 531
<212> TYPE: PRT
<213> ORGANISM: Artificial Sequence
<220> FEATURE:
<223> OTHER INFORMATION: Recombinant protein

<400> SEQUENCE: 53

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Val Pro Arg
    210                 215                 220

Gly Ser Pro Glu Phe Pro Gly Asn Ser Tyr Asp His Asp Tyr Ala Lys
225                 230                 235                 240

Leu Ser Thr Leu Tyr Arg Lys Val Gly Gly Gly Leu Glu Val Leu Phe
                245                 250                 255

Gln Gly Pro Pro Arg Ile Tyr Lys Pro Cys Phe Val Cys Gln Asp Lys
            260                 265                 270

Ser Ser Gly Tyr His Tyr Gly Val Ser Ala Cys Glu Gly Cys Lys Gly
        275                 280                 285

Phe Phe Arg Arg Ser Ile Gln Lys Asn Met Val Tyr Thr Cys His Arg
    290                 295                 300

Asp Lys Asn Cys Ile Ile Asn Lys Val Thr Arg Asn Arg Cys Gln Tyr
305                 310                 315                 320

Cys Arg Leu Gln Lys Cys Phe Glu Val Gly Met Ser Lys Glu Ser Val
                325                 330                 335

Arg Asn Asp Arg Asn Lys Lys Lys Lys Glu Val Pro Lys Pro Glu Cys
```

```
            340                 345                 350

Ser Glu Ser Ala Ser Leu Tyr Lys Lys Ala Gly Ser Gly Gly Gly Gln
        355                 360                 365

Leu Gly Gly Ser Ser Ser Asn Pro Ala Phe Leu Tyr Lys Val Gly His
    370                 375                 380

Ser Asn Glu Lys Trp Phe His Gly Lys Leu Gly Ala Gly Arg Asp Gly
385                 390                 395                 400

Arg His Ile Ala Glu Arg Leu Leu Thr Glu Tyr Cys Ile Glu Thr Gly
                405                 410                 415

Ala Pro Asp Gly Ser Phe Leu Val Arg Glu Ser Glu Thr Phe Val Gly
            420                 425                 430

Asp Tyr Thr Leu Ser Phe Trp Arg Asn Gly Lys Val Gln His Cys Arg
        435                 440                 445

Ile His Ser Arg Gln Asp Ala Gly Thr Pro Lys Phe Phe Leu Thr Asp
    450                 455                 460

Asn Leu Val Phe Asp Ser Leu Tyr Asp Leu Ile Thr His Tyr Gln Gln
465                 470                 475                 480

Val Pro Leu Arg Cys Asn Glu Phe Glu Met Arg Leu Ser Glu Pro Val
                485                 490                 495

Pro Gln Gly Gly Gly Tyr Pro Tyr Asp Val Pro Asp Tyr Ala Leu Gly
            500                 505                 510

Gly Ser Glu Tyr Met Pro Met Glu Asn Ser Ala Val Asp His His His
        515                 520                 525

His His His
    530


<210> SEQ ID NO 54
<211> LENGTH: 1794
<212> TYPE: DNA
<213> ORGANISM: Artificial Sequence
<220> FEATURE:
<223> OTHER INFORMATION: Recombinant protein

<400> SEQUENCE: 54

atgtccccta tactaggtta ttggaaaatt aagggccttg tgcaacccac tcgacttctt      60

ttggaatatc ttgaagaaaa atatgaagag catttgtatg agcgcgatga aggtgataaa     120

tggcgaaaca aaaagtttga attgggtttg gagtttccca atcttcctta ttatattgat     180

ggtgatgtta aattaacaca gtctatggcc atcatacgtt atatagctga caagcacaac     240

atgttgggtg gttgtccaaa agagcgtgca gagatttcaa tgcttgaagg agcggttttg     300

gatattagat acggtgtttc gagaattgca tatagtaaag actttgaaac tctcaaagtt     360

gattttctta gcaagctacc tgaaatgctg aaaatgttcg aagatcgttt atgtcataaa     420

acatatttaa atggtgatca tgtaacccat cctgacttca tgttgtatga cgctcttgat     480

gttgttttat acatggaccc aatgtgcctg gatgcgttcc caaaattagt ttgttttaaa     540

aaacgtattg aagctatccc acaaattgat aagtacttga aatccagcaa gtatatagca     600

tggcctttgc agggctggca agccacgttt ggtggtggcg accatcctcc aaaatcggat     660

ctggttccgc gtggatcccc ggaattccca ggaaacagct atgaccatga ttacgccaag     720

ctatcaactt tgtatagaaa agttggtggt ggcctggaag ttctgttcca ggggcccccc     780

cgcatctaca agccttgctt tgtctgtcag gacaagtcct caggctacca ctatggggtc     840

agcgcctgtg agggctgcaa gggcttcttc cgccgcagca tccagaagaa catggtgtac     900

acgtgtcacc gggacaagaa ctgcatcatc aacaaggtga cccggaaccg ctgccagtac     960
```

-continued

```
tgccgactgc agaagtgctt tgaagtgggc atgtccaagg agtctgtgag aaacgaccga   1020

aacaagaaga agaaggaggt gcccaagccc gagtgctctg agagcgcaag tttgtacaaa   1080

aaagcaggct ccggtggcgg ccgcaaaaaa aaacagcagg aagaggaagc agaacgtctg   1140

cgtcgtattc aagaagaaat ggaaaaggaa cgcaaacgcc gtgaagaaga cgaaaaacgt   1200

cgccgcaagg aagaggagga acgtcgtatg aagcttggcg gtagctcgag caacccagct   1260

ttcttgtaca aagtgggtgg ctcgagcacc tataagttaa tccttaacgg caagacgtta   1320

aagggtgaga ccaccaccga agctgttgat gctgctaccg cggagaaggt ctttaagcag   1380

tatgcgaatg ataatggcgt ggacggcgaa tggacgtacg acgacgccac caaaacgttc   1440

acagttaccg agaaaccaga agtgatcgat gcgtctgaat taacaccagc cgtgacaact   1500

tacaaacttg ttattaatgg taaaacattg aaaggcgaaa caactactaa agcagtagac   1560

gcagaaactg cagaaaaagc cttcaaacaa tacgctaacg acaacggtgt tgatggtgtt   1620

tggacttatg atgatgcgac taagaccttt acggtaactg aaggtggtag cggcggcggt   1680

atgaaagaaa ccgctgctgc taaattcgaa cgccagcaca tggacagccc agatctgggt   1740

gagtatatgc cgatggaaaa tagcgccgtc gaccaccacc atcatcacca ttaa         1794
```

<210> SEQ ID NO 55
<211> LENGTH: 597
<212> TYPE: PRT
<213> ORGANISM: Artificial Sequence
<220> FEATURE:
<223> OTHER INFORMATION: Recombinant protein

<400> SEQUENCE: 55

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Val Pro Arg
```

-continued

```
    210                 215                 220

Gly Ser Pro Glu Phe Pro Gly Asn Ser Tyr Asp His Asp Tyr Ala Lys
225                 230                 235                 240

Leu Ser Thr Leu Tyr Arg Lys Val Gly Gly Gly Leu Glu Val Leu Phe
                245                 250                 255

Gln Gly Pro Pro Arg Ile Tyr Lys Pro Cys Phe Val Cys Gln Asp Lys
            260                 265                 270

Ser Ser Gly Tyr His Tyr Gly Val Ser Ala Cys Glu Gly Cys Lys Gly
        275                 280                 285

Phe Phe Arg Arg Ser Ile Gln Lys Asn Met Val Tyr Thr Cys His Arg
    290                 295                 300

Asp Lys Asn Cys Ile Ile Asn Lys Val Thr Arg Asn Arg Cys Gln Tyr
305                 310                 315                 320

Cys Arg Leu Gln Lys Cys Phe Glu Val Gly Met Ser Lys Glu Ser Val
                325                 330                 335

Arg Asn Asp Arg Asn Lys Lys Lys Lys Glu Val Pro Lys Pro Glu Cys
            340                 345                 350

Ser Glu Ser Ala Ser Leu Tyr Lys Lys Ala Gly Ser Gly Gly Gly Arg
        355                 360                 365

Lys Lys Lys Gln Gln Glu Glu Glu Ala Glu Arg Leu Arg Arg Ile Gln
    370                 375                 380

Glu Glu Met Glu Lys Glu Arg Lys Arg Arg Glu Glu Asp Glu Lys Arg
385                 390                 395                 400

Arg Arg Lys Glu Glu Glu Glu Arg Arg Met Lys Leu Gly Gly Ser Ser
                405                 410                 415

Ser Asn Pro Ala Phe Leu Tyr Lys Val Gly Gly Ser Ser Thr Tyr Lys
            420                 425                 430

Leu Ile Leu Asn Gly Lys Thr Leu Lys Gly Glu Thr Thr Thr Glu Ala
        435                 440                 445

Val Asp Ala Ala Thr Ala Glu Lys Val Phe Lys Gln Tyr Ala Asn Asp
    450                 455                 460

Asn Gly Val Asp Gly Glu Trp Thr Tyr Asp Asp Ala Thr Lys Thr Phe
465                 470                 475                 480

Thr Val Thr Glu Lys Pro Glu Val Ile Asp Ala Ser Glu Leu Thr Pro
                485                 490                 495

Ala Val Thr Thr Tyr Lys Leu Val Ile Asn Gly Lys Thr Leu Lys Gly
            500                 505                 510

Glu Thr Thr Thr Lys Ala Val Asp Ala Glu Thr Ala Glu Lys Ala Phe
        515                 520                 525

Lys Gln Tyr Ala Asn Asp Asn Gly Val Asp Gly Val Trp Thr Tyr Asp
    530                 535                 540

Asp Ala Thr Lys Thr Phe Thr Val Thr Glu Gly Gly Ser Gly Gly Gly
545                 550                 555                 560

Met Lys Glu Thr Ala Ala Ala Lys Phe Glu Arg Gln His Met Asp Ser
                565                 570                 575

Pro Asp Leu Gly Glu Tyr Met Pro Met Glu Asn Ser Ala Val Asp His
            580                 585                 590

His His His His His
        595
```

<210> SEQ ID NO 56
<211> LENGTH: 98
<212> TYPE: PRT
<213> ORGANISM: Artificial Sequence
<220> FEATURE:
<223> OTHER INFORMATION: Recombinant protein

<400> SEQUENCE: 56

```
Pro Pro His Glu Arg Pro Tyr Ala Cys Pro Val Glu Ser Cys Asp Arg
1               5                   10                  15

Arg Phe Ser Arg Ser Asp Glu Leu Thr Arg His Ile Arg Ile His Thr
            20                  25                  30

Gly Gln Lys Pro Phe Gln Cys Arg Ile Cys Met Arg Asn Phe Ser Arg
        35                  40                  45

Ser Asp His Leu Thr Thr His Ile Arg Thr His Thr Gly Glu Lys Pro
    50                  55                  60

Phe Ala Cys Asp Ile Cys Gly Arg Lys Phe Ala Arg Ser Asp Glu Arg
65                  70                  75                  80

Lys Arg His Thr Lys Ile His Leu Arg Gln Lys Asp Lys Lys Ala Asp
                85                  90                  95

Lys Ser
```

<210> SEQ ID NO 57
<211> LENGTH: 837
<212> TYPE: DNA
<213> ORGANISM: Artificial Sequence
<220> FEATURE:
<223> OTHER INFORMATION: Recombinant protein

<400> SEQUENCE: 57

```
aatgctgcgc aacacgatga agctcaacaa aatgcttttt atcaagtgtt aaatatgcct      60

aacttaaacg ctgatcaacg taatggtttt atccaaagcc ttaaagatga tccaagccaa     120

agtgctaacg ttttaggtga agctcaaaaa cttaatgact ctcaagctcc aaaagctgat     180

gcgcaacaaa ataagttcaa caaagatcaa caaagcgcct tctatgaaat cttgaacatg     240

cctaacttaa acgaagagca acgcaatggt ttcattcaaa gtcttaaaga cgatccaagc     300

caaagcacta acgttttagg tgaagctaaa aaattaaacg aatctcaagc accgaaagct     360

gacaacaatt tcaacaaaga acaacaaaat gctttctatg aaatcttgaa catgcctaac     420

ttgaacgaag aacaacgcaa tggtttcatc caaagcttaa aagatgaccc aagccaaagc     480

gctaaccttt tagcagaagc taaaaagcta aatgatgcac aagcaccaaa agctgacaac     540

aaattcaaca aagaacaaca aaatgctttc tatgaaattt tacatttacc taacttaact     600

gaagaacaac gtaacggctt catccaaagc cttaaagacg atccttcagt gagcaaagaa     660

attttagcag aagctaaaaa gctaaacgat gctcaagcac caaaaggtgg tagcggcggc     720

ggtatgaaag aaaccgctgc tgctaaattc gaacgccagc acatggacag cccagatctg     780

ggtgagtata tgccgatgga aaatagcgcc gtcgaccacc accatcatca ccattaa        837
```

<210> SEQ ID NO 58
<211> LENGTH: 278
<212> TYPE: PRT
<213> ORGANISM: Artificial Sequence
<220> FEATURE:
<223> OTHER INFORMATION: Recombinant protein

<400> SEQUENCE: 58

```
Asn Ala Ala Gln His Asp Glu Ala Gln Gln Asn Ala Phe Tyr Gln Val
1               5                   10                  15

Leu Asn Met Pro Asn Leu Asn Ala Asp Gln Arg Asn Gly Phe Ile Gln
            20                  25                  30
```

```
Ser Leu Lys Asp Asp Pro Ser Gln Ser Ala Asn Val Leu Gly Glu Ala
        35                  40                  45

Gln Lys Leu Asn Asp Ser Gln Ala Pro Lys Ala Asp Ala Gln Gln Asn
    50                  55                  60

Lys Phe Asn Lys Asp Gln Gln Ser Ala Phe Tyr Glu Ile Leu Asn Met
65                  70                  75                  80

Pro Asn Leu Asn Glu Glu Gln Arg Asn Gly Phe Ile Gln Ser Leu Lys
                85                  90                  95

Asp Asp Pro Ser Gln Ser Thr Asn Val Leu Gly Glu Ala Lys Lys Leu
            100                 105                 110

Asn Glu Ser Gln Ala Pro Lys Ala Asp Asn Asn Phe Asn Lys Glu Gln
        115                 120                 125

Gln Asn Ala Phe Tyr Glu Ile Leu Asn Met Pro Asn Leu Asn Glu Glu
    130                 135                 140

Gln Arg Asn Gly Phe Ile Gln Ser Leu Lys Asp Asp Pro Ser Gln Ser
145                 150                 155                 160

Ala Asn Leu Leu Ala Glu Ala Lys Lys Leu Asn Asp Ala Gln Ala Pro
                165                 170                 175

Lys Ala Asp Asn Lys Phe Asn Lys Glu Gln Gln Asn Ala Phe Tyr Glu
            180                 185                 190

Ile Leu His Leu Pro Asn Leu Thr Glu Glu Gln Arg Asn Gly Phe Ile
        195                 200                 205

Gln Ser Leu Lys Asp Asp Pro Ser Val Ser Lys Glu Ile Leu Ala Glu
    210                 215                 220

Ala Lys Lys Leu Asn Asp Ala Gln Ala Pro Lys Gly Gly Ser Gly Gly
225                 230                 235                 240

Gly Met Lys Glu Thr Ala Ala Ala Lys Phe Glu Arg Gln His Met Asp
                245                 250                 255

Ser Pro Asp Leu Gly Glu Tyr Met Pro Met Glu Asn Ser Ala Val Asp
            260                 265                 270

His His His His His His
        275


<210> SEQ ID NO 59
<211> LENGTH: 1722
<212> TYPE: DNA
<213> ORGANISM: Artificial Sequence
<220> FEATURE:
<223> OTHER INFORMATION: Recombinant protein

<400> SEQUENCE: 59

atgtccccta tactaggtta ttggaaaatt aagggccttg tgcaacccac tcgacttctt      60

ttggaatatc ttgaagaaaa atatgaagag catttgtatg agcgcgatga aggtgataaa     120

tggcgaaaca aaaagtttga attgggtttg gagtttccca atcttcctta ttatattgat     180

ggtgatgtta aattaacaca gtctatggcc atcatacgtt atatagctga caagcacaac     240

atgttgggtg gttgtccaaa agagcgtgca gagatttcaa tgcttgaagg agcggttttg     300

gatattagat acggtgtttc gagaattgca tatagtaaag actttgaaac tctcaaagtt     360

gattttctta gcaagctacc tgaaatgctg aaaatgttcg aagatcgttt atgtcataaa     420

acatatttaa atggtgatca tgtaacccat cctgacttca tgttgtatga cgctcttgat     480

gttgttttat acatggaccc aatgtgcctg gatgcgttcc caaaattagt ttgttttaaa     540

aaacgtattg aagctatccc acaaattgat aagtacttga aatccagcaa gtatatagca     600

tggcctttgc agggctggca agccacgttt ggtggtggcg accatcctcc aaaatcggat     660
```

```
ctggttccgc gtggatcccc ggaattccca ggaaacagct atgaccatga ttacgccaag    720

ctatcaactt tgtatagaaa agttggtggt ggcctggaag ttctgttcca ggggccctcc    780

ttcaccaagc acatctgcgc catctgcggg gaccgctcct caggcaagca ctatggagtg    840

tacagctgcg aggggtgcaa gggcttcttc aagcggacgg tgcgcaagga cctgacctac    900

acctgccgcg acaacaagga ctgcctgatt gacaagcggc agcggaaccg gtgccagtac    960

tgccgctacc agaagtgcct ggccatgggc atgaagcggg aagccgtgca ggaggagcgg   1020

cagcgtggca aggaccggaa cgagaatgag gtggagtcga ccagcgcaag tttgtacaaa   1080

aaagcaggct ccggcggtgg tggcgagatc gctgcactgg agaaggagat tgccgctctg   1140

gaaaaggaga tcgcggcact ggagaagggt ggtggcgggt acccagcttt cttgtacaaa   1200

gtgggtggct cgagcaccta taagttaatc cttaacggca agacgttaaa gggtgagacc   1260

accaccgaag ctgttgatgc tgctaccgcg gagaaggtct ttaagcagta tgcgaatgat   1320

aatggcgtgg acggcgaatg gacgtacgac gacgccacca aaacgttcac agttaccgag   1380

aaaccagaag tgatcgatgc gtctgaatta acaccagccg tgacaactta caaacttgtt   1440

attaatggta aaacattgaa aggcgaaaca actactaaag cagtagacgc agaaactgca   1500

gaaaaagcct tcaaacaata cgctaacgac aacggtgttg atggtgtttg gacttatgat   1560

gatgcgacta agacctttac ggtaactgaa ggtggtagcg gcggcggtat gaaagaaacc   1620

gctgctgcta aattcgaacg ccagcacatg gacagcccag atctgggtga gtatatgccg   1680

atggaaaata gcgccgtcga ccaccaccat catcaccatt aa                      1722
```

<210> SEQ ID NO 60
<211> LENGTH: 573
<212> TYPE: PRT
<213> ORGANISM: Artificial Sequence
<220> FEATURE:
<223> OTHER INFORMATION: Recombinant protein

<400> SEQUENCE: 60

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175
```

```
Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Val Pro Arg
    210                 215                 220

Gly Ser Pro Glu Phe Pro Gly Asn Ser Tyr Asp His Asp Tyr Ala Lys
225                 230                 235                 240

Leu Ser Thr Leu Tyr Arg Lys Val Gly Gly Gly Leu Glu Val Leu Phe
                245                 250                 255

Gln Gly Pro Ser Phe Thr Lys His Ile Cys Ala Ile Cys Gly Asp Arg
            260                 265                 270

Ser Ser Gly Lys His Tyr Gly Val Tyr Ser Cys Glu Gly Cys Lys Gly
        275                 280                 285

Phe Phe Lys Arg Thr Val Arg Lys Asp Leu Thr Tyr Thr Cys Arg Asp
    290                 295                 300

Asn Lys Asp Cys Leu Ile Asp Lys Arg Gln Arg Asn Arg Cys Gln Tyr
305                 310                 315                 320

Cys Arg Tyr Gln Lys Cys Leu Ala Met Gly Met Lys Arg Glu Ala Val
                325                 330                 335

Gln Glu Glu Arg Gln Arg Gly Lys Asp Arg Asn Glu Asn Glu Val Glu
            340                 345                 350

Ser Thr Ser Ala Ser Leu Tyr Lys Lys Ala Gly Ser Gly Gly Gly Gly
        355                 360                 365

Glu Ile Ala Ala Leu Glu Lys Glu Ile Ala Ala Leu Glu Lys Glu Ile
    370                 375                 380

Ala Ala Leu Glu Lys Gly Gly Gly Gly Tyr Pro Ala Phe Leu Tyr Lys
385                 390                 395                 400

Val Gly Gly Ser Ser Thr Tyr Lys Leu Ile Leu Asn Gly Lys Thr Leu
                405                 410                 415

Lys Gly Glu Thr Thr Thr Glu Ala Val Asp Ala Ala Thr Ala Glu Lys
            420                 425                 430

Val Phe Lys Gln Tyr Ala Asn Asp Asn Gly Val Asp Gly Glu Trp Thr
        435                 440                 445

Tyr Asp Asp Ala Thr Lys Thr Phe Thr Val Thr Glu Lys Pro Glu Val
    450                 455                 460

Ile Asp Ala Ser Glu Leu Thr Pro Ala Val Thr Thr Tyr Lys Leu Val
465                 470                 475                 480

Ile Asn Gly Lys Thr Leu Lys Gly Glu Thr Thr Thr Lys Ala Val Asp
                485                 490                 495

Ala Glu Thr Ala Glu Lys Ala Phe Lys Gln Tyr Ala Asn Asp Asn Gly
            500                 505                 510

Val Asp Gly Val Trp Thr Tyr Asp Asp Ala Thr Lys Thr Phe Thr Val
        515                 520                 525

Thr Glu Gly Gly Ser Gly Gly Gly Met Lys Glu Thr Ala Ala Ala Lys
    530                 535                 540

Phe Glu Arg Gln His Met Asp Ser Pro Asp Leu Gly Glu Tyr Met Pro
545                 550                 555                 560

Met Glu Asn Ser Ala Val Asp His His His His His His
                565                 570
```

<210> SEQ ID NO 61
<211> LENGTH: 1665

<212> TYPE: DNA
<213> ORGANISM: Artificial Sequence
<220> FEATURE:
<223> OTHER INFORMATION: Recombinant protein

<400> SEQUENCE: 61
atgtccccta tactaggtta ttggaaaatt aagggccttg tgcaacccac tcgacttctt 60
ttggaatatc ttgaagaaaa atatgaagag catttgtatg agcgcgatga aggtgataaa 120
tggcgaaaca aaaagtttga attgggtttg gagtttccca atcttcctta ttatattgat 180
ggtgatgtta aattaacaca gtctatggcc atcatacgtt atatagctga caagcacaac 240
atgttgggtg gttgtccaaa agagcgtgca gagatttcaa tgcttgaagg agcggttttg 300
gatattagat acggtgtttc gagaattgca tatagtaaag actttgaaac tctcaaagtt 360
gattttctta gcaagctacc tgaaatgctg aaaatgttcg aagatcgttt atgtcataaa 420
acatatttaa atggtgatca tgtaacccat cctgacttca tgttgtatga cgctcttgat 480
gttgttttat acatggaccc aatgtgcctg gatgcgttcc caaaattagt ttgttttaaa 540
aaacgtattg aagctatccc acaaattgat aagtacttga aatccagcaa gtatatagca 600
tggcctttgc agggctggca agccacgttt ggtggtggcg accatcctcc aaaatcggat 660
ctggttccgc gtggatcccc ggaattccca ggaaacagct atgaccatga ttacgccaag 720
ctatcaactt tgtatagaaa agttggtggt ggcctggaag ttctgttcca ggggcccccc 780
cgcatctaca agccttgctt tgtctgtcag gacaagtcct caggctacca ctatggggtc 840
agcgcctgtg agggctgcaa gggcttcttc cgccgcagca tccagaagaa catggtgtac 900
acgtgtcacc gggacaagaa ctgcatcatc aacaaggtga cccggaaccg ctgccagtac 960
tgccgactgc agaagtgctt tgaagtgggc atgtccaagg agtctgtgag aaacgaccga 1020
aacaagaaga agaaggaggt gcccaagccc gagtgctctg agagcgcaag tttgtacaaa 1080
aaagcaggct ccggtggcgg ccagcttggc ggtagctcga gcaacccagc tttcttgtac 1140
aaagtgggtg gctcgagcac ctataagtta atccttaacg gcaagacgtt aaagggtgag 1200
accaccaccg aagctgttga tgctgctacc gcggagaagg tctttaagca gtatgcgaat 1260
gataatggcg tggacggcga atggacgtac gacgacgcca ccaaaacgtt cacagttacc 1320
gagaaaccag aagtgatcga tgcgtctgaa ttaacaccag ccgtgacaac ttacaaactt 1380
gttattaatg gtaaaacatt gaaaggcgaa acaactacta aagcagtaga cgcagaaact 1440
gcagaaaaag ccttcaaaca atacgctaac gacaacggtg ttgatggtgt ttggacttat 1500
gatgatgcga ctaagacctt tacggtaact gaaggtggta gcggcggcgg tatgaaagaa 1560
accgctgctg ctaaattcga acgccagcac atggacagcc cagatctggg tgagtatatg 1620
ccgatggaaa atagcgccgt cgaccaccac catcatcacc attaa 1665

<210> SEQ ID NO 62
<211> LENGTH: 554
<212> TYPE: PRT
<213> ORGANISM: Artificial Sequence
<220> FEATURE:
<223> OTHER INFORMATION: Recombinant protein

<400> SEQUENCE: 62

Met Ser Pro Ile Leu Gly Tyr Trp Lys Ile Lys Gly Leu Val Gln Pro
1 5 10 15

Thr Arg Leu Leu Leu Glu Tyr Leu Glu Glu Lys Tyr Glu Glu His Leu
20 25 30

-continued

```
Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Val Pro Arg
    210                 215                 220

Gly Ser Pro Glu Phe Pro Gly Asn Ser Tyr Asp His Asp Tyr Ala Lys
225                 230                 235                 240

Leu Ser Thr Leu Tyr Arg Lys Val Gly Gly Gly Leu Glu Val Leu Phe
                245                 250                 255

Gln Gly Pro Pro Arg Ile Tyr Lys Pro Cys Phe Val Cys Gln Asp Lys
            260                 265                 270

Ser Ser Gly Tyr His Tyr Gly Val Ser Ala Cys Glu Gly Cys Lys Gly
        275                 280                 285

Phe Phe Arg Arg Ser Ile Gln Lys Asn Met Val Tyr Thr Cys His Arg
    290                 295                 300

Asp Lys Asn Cys Ile Ile Asn Lys Val Thr Arg Asn Arg Cys Gln Tyr
305                 310                 315                 320

Cys Arg Leu Gln Lys Cys Phe Glu Val Gly Met Ser Lys Glu Ser Val
                325                 330                 335

Arg Asn Asp Arg Asn Lys Lys Lys Lys Glu Val Pro Lys Pro Glu Cys
            340                 345                 350

Ser Glu Ser Ala Ser Leu Tyr Lys Lys Ala Gly Ser Gly Gly Gly Gln
        355                 360                 365

Leu Gly Gly Ser Ser Ser Asn Pro Ala Phe Leu Tyr Lys Val Gly Gly
    370                 375                 380

Ser Ser Thr Tyr Lys Leu Ile Leu Asn Gly Lys Thr Leu Lys Gly Glu
385                 390                 395                 400

Thr Thr Thr Glu Ala Val Asp Ala Ala Thr Ala Glu Lys Val Phe Lys
                405                 410                 415

Gln Tyr Ala Asn Asp Asn Gly Val Asp Gly Glu Trp Thr Tyr Asp Asp
            420                 425                 430

Ala Thr Lys Thr Phe Thr Val Thr Glu Lys Pro Glu Val Ile Asp Ala
        435                 440                 445

Ser Glu Leu Thr Pro Ala Val Thr Thr Tyr Lys Leu Val Ile Asn Gly
```

```
    450                 455                 460

Lys Thr Leu Lys Gly Glu Thr Thr Thr Lys Ala Val Asp Ala Glu Thr
465                 470                 475                 480

Ala Glu Lys Ala Phe Lys Gln Tyr Ala Asn Asp Asn Gly Val Asp Gly
                485                 490                 495

Val Trp Thr Tyr Asp Asp Ala Thr Lys Thr Phe Thr Val Thr Glu Gly
            500                 505                 510

Gly Ser Gly Gly Gly Met Lys Glu Thr Ala Ala Ala Lys Phe Glu Arg
        515                 520                 525

Gln His Met Asp Ser Pro Asp Leu Gly Glu Tyr Met Pro Met Glu Asn
    530                 535                 540

Ser Ala Val Asp His His His His His His
545                 550


<210> SEQ ID NO 63
<211> LENGTH: 1686
<212> TYPE: DNA
<213> ORGANISM: Artificial Sequence
<220> FEATURE:
<223> OTHER INFORMATION: Recombinant protein

<400> SEQUENCE: 63

atgtccccta tactaggtta ttggaaaatt aagggccttg tgcaacccac tcgacttctt      60

ttggaatatc ttgaagaaaa atatgaagag catttgtatg agcgcgatga aggtgataaa     120

tggcgaaaca aaaagtttga attgggtttg gagtttccca atcttcctta ttatattgat     180

ggtgatgtta aattaacaca gtctatggcc atcatacgtt atatagctga caagcacaac     240

atgttgggtg gttgtccaaa agagcgtgca gagatttcaa tgcttgaagg agcggttttg     300

gatattagat acggtgtttc gagaattgca tatagtaaag actttgaaac tctcaaagtt     360

gattttctta gcaagctacc tgaaatgctg aaaatgttcg aagatcgttt atgtcataaa     420

acatatttaa atggtgatca tgtaacccat cctgacttca tgttgtatga cgctcttgat     480

gttgttttat acatggaccc aatgtgcctg gatgcgttcc caaaattagt ttgttttaaa     540

aaacgtattg aagctatccc acaaattgat aagtacttga aatccagcaa gtatatagca     600

tggcctttgc agggctggca agccacgttt ggtggtggcg accatcctcc aaaatcggat     660

ctggttccgc gtggatcccc ggaattccca ggaaacagct atgaccatga ttacgccaag     720

ctatcaactt tgtatagaaa agttggtggt ggcctggaag ttctgttcca ggggcccgaa     780

cgcccatatg cttgccctgt cgagtcctgc gatcgccgct tttctcgctc ggatgagctt     840

acccgccata tccgcatcca cacaggccag aagcccttcc agtgtcgaat ctgcatgcgt     900

aacttcagtc gtagtgacca ccttaccacc cacatccgca cccacacagg cgagaagcct     960

tttgcctgtg acatttgtgg gaggaagttt gccaggagtg atgaaaaaat ccatttaaga    1020

cagaaggacg caagtttgta caaaaaagca ggctccggcg gtggtggcga gatcgctgca    1080

ctggagaagg agattgccgc tctggaaaag gagatcgcgg cactggagaa gggtggtggc    1140

gggtacccag ctttcttgta caaagtgggt ggctcgagca cctataagtt aatccttaac    1200

ggcaagacgt taaagggtga gaccaccacc gaagctgttg atgctgctac cgcggagaag    1260

gtctttaagc agtatgcgaa tgataatggc gtggacggcg aatggacgta cgacgacgcc    1320

accaaaacgt tcacagttac cgagaaacca gaagtgatcg atgcgtctga attaacacca    1380

gccgtgacaa cttacaaact tgttattaat ggtaaaacat tgaaaggcga aacaactact    1440

aaagcagtag acgcagaaac tgcagaaaaa gccttcaaac aatacgctaa cgacaacggt    1500
```

gttgatggtg tttggactta tgatgatgcg actaagacct ttacggtaac tgaaggtggt 1560
agcggcggcg gtatgaaaga aaccgctgct gctaaattcg aacgccagca catggacagc 1620
ccagatctgg gtgagtatat gccgatggaa aatagcgccg tcgaccacca ccatcatcac 1680
cattaa 1686

<210> SEQ ID NO 64
<211> LENGTH: 561
<212> TYPE: PRT
<213> ORGANISM: Artificial Sequence
<220> FEATURE:
<223> OTHER INFORMATION: Recombinant protein

<400> SEQUENCE: 64

Met Ser Pro Ile Leu Gly Tyr Trp Lys Ile Lys Gly Leu Val Gln Pro
1 5 10 15

Thr Arg Leu Leu Leu Glu Tyr Leu Glu Glu Lys Tyr Glu Glu His Leu
20 25 30

Tyr Glu Arg Asp Glu Gly Asp Lys Trp Arg Asn Lys Lys Phe Glu Leu
35 40 45

Gly Leu Glu Phe Pro Asn Leu Pro Tyr Tyr Ile Asp Gly Asp Val Lys
50 55 60

Leu Thr Gln Ser Met Ala Ile Ile Arg Tyr Ile Ala Asp Lys His Asn
65 70 75 80

Met Leu Gly Gly Cys Pro Lys Glu Arg Ala Glu Ile Ser Met Leu Glu
85 90 95

Gly Ala Val Leu Asp Ile Arg Tyr Gly Val Ser Arg Ile Ala Tyr Ser
100 105 110

Lys Asp Phe Glu Thr Leu Lys Val Asp Phe Leu Ser Lys Leu Pro Glu
115 120 125

Met Leu Lys Met Phe Glu Asp Arg Leu Cys His Lys Thr Tyr Leu Asn
130 135 140

Gly Asp His Val Thr His Pro Asp Phe Met Leu Tyr Asp Ala Leu Asp
145 150 155 160

Val Val Leu Tyr Met Asp Pro Met Cys Leu Asp Ala Phe Pro Lys Leu
165 170 175

Val Cys Phe Lys Lys Arg Ile Glu Ala Ile Pro Gln Ile Asp Lys Tyr
180 185 190

Leu Lys Ser Ser Lys Tyr Ile Ala Trp Pro Leu Gln Gly Trp Gln Ala
195 200 205

Thr Phe Gly Gly Gly Asp His Pro Pro Lys Ser Asp Leu Val Pro Arg
210 215 220

Gly Ser Pro Glu Phe Pro Gly Asn Ser Tyr Asp His Asp Tyr Ala Lys
225 230 235 240

Leu Ser Thr Leu Tyr Arg Lys Val Gly Gly Gly Leu Glu Val Leu Phe
245 250 255

Gln Gly Pro Glu Arg Pro Tyr Ala Cys Pro Val Glu Ser Cys Asp Arg
260 265 270

Arg Phe Ser Arg Ser Asp Glu Leu Thr Arg His Ile Arg Ile His Thr
275 280 285

Gly Gln Lys Pro Phe Gln Cys Arg Ile Cys Met Arg Asn Phe Ser Arg
290 295 300

Ser Asp His Leu Thr Thr His Ile Arg Thr His Thr Gly Glu Lys Pro
305 310 315 320

-continued

```
Phe Ala Cys Asp Ile Cys Gly Arg Lys Phe Ala Arg Ser Asp Glu Lys
                325                 330                 335

Ile His Leu Arg Gln Lys Asp Ala Ser Leu Tyr Lys Lys Ala Gly Ser
            340                 345                 350

Gly Gly Gly Gly Glu Ile Ala Ala Leu Glu Lys Glu Ile Ala Ala Leu
        355                 360                 365

Glu Lys Glu Ile Ala Ala Leu Glu Lys Gly Gly Gly Gly Tyr Pro Ala
    370                 375                 380

Phe Leu Tyr Lys Val Gly Gly Ser Ser Thr Tyr Lys Leu Ile Leu Asn
385                 390                 395                 400

Gly Lys Thr Leu Lys Gly Glu Thr Thr Thr Glu Ala Val Asp Ala Ala
                405                 410                 415

Thr Ala Glu Lys Val Phe Lys Gln Tyr Ala Asn Asp Asn Gly Val Asp
            420                 425                 430

Gly Glu Trp Thr Tyr Asp Asp Ala Thr Lys Thr Phe Thr Val Thr Glu
        435                 440                 445

Lys Pro Glu Val Ile Asp Ala Ser Glu Leu Thr Pro Ala Val Thr Thr
    450                 455                 460

Tyr Lys Leu Val Ile Asn Gly Lys Thr Leu Lys Gly Glu Thr Thr Thr
465                 470                 475                 480

Lys Ala Val Asp Ala Glu Thr Ala Glu Lys Ala Phe Lys Gln Tyr Ala
                485                 490                 495

Asn Asp Asn Gly Val Asp Gly Val Trp Thr Tyr Asp Asp Ala Thr Lys
            500                 505                 510

Thr Phe Thr Val Thr Glu Gly Gly Ser Gly Gly Gly Met Lys Glu Thr
        515                 520                 525

Ala Ala Ala Lys Phe Glu Arg Gln His Met Asp Ser Pro Asp Leu Gly
    530                 535                 540

Glu Tyr Met Pro Met Glu Asn Ser Ala Val Asp His His His His His
545                 550                 555                 560

His
```

<210> SEQ ID NO 65
<211> LENGTH: 1629
<212> TYPE: DNA
<213> ORGANISM: Artificial Sequence
<220> FEATURE:
<223> OTHER INFORMATION: Recombinant protein

<400> SEQUENCE: 65

```
atgtccccta tactaggtta ttggaaaatt aagggccttg tgcaacccac tcgacttctt      60
ttggaatatc ttgaagaaaa atatgaagag catttgtatg agcgcgatga aggtgataaa     120
tggcgaaaca aaaagtttga attgggtttg gagtttccca atcttcctta ttatattgat     180
ggtgatgtta aattaacaca gtctatggcc atcatacgtt atatagctga caagcacaac     240
atgttgggtg gttgtccaaa agagcgtgca gagatttcaa tgcttgaagg agcggttttg     300
gatattagat acggtgtttc gagaattgca tatagtaaag actttgaaac tctcaaagtt     360
gattttctta gcaagctacc tgaaatgctg aaaatgttcg aagatcgttt atgtcataaa     420
acatatttaa atggtgatca tgtaacccat cctgacttca tgttgtatga cgctcttgat     480
gttgttttat acatggaccc aatgtgcctg gatgcgttcc caaaattagt ttgttttaaa     540
aaacgtattg aagctatccc acaaattgat aagtacttga aatccagcaa gtatatagca     600
tggcctttgc agggctggca agccacgttt ggtggtggcg accatcctcc aaaatcggat     660
```

-continued

```
ctggttccgc gtggatcccc ggaattccca ggaaacagct atgaccatga ttacgccaag    720

ctatcaactt tgtatagaaa agttggtggt ggcctggaag ttctgttcca ggggcccgaa    780

cgcccatatg cttgccctgt cgagtcctgc gatcgccgct tttctcgctc ggatgagctt    840

acccgccata tccgcatcca cacaggccag aagcccttcc agtgtcgaat ctgcatgcgt    900

aacttcagtc gtagtgacca ccttaccacc cacatccgca cccacacagg cgagaagcct    960

tttgcctgtg acatttgtgg gaggaagttt gccaggagtg atgaaaaaat ccatttaaga   1020

cagaaggacg caagtttgta caaaaaagca ggctccggtg gcggccagct tggcggtagc   1080

tcgagcaacc cagctttctt gtacaaagtg ggtggctcga gcacctataa gttaatcctt   1140

aacggcaaga cgttaaaggg tgagaccacc accgaagctg ttgatgctgc taccgcggag   1200

aaggtcttta agcagtatgc gaatgataat ggcgtggacg gcgaatggac gtacgacgac   1260

gccaccaaaa cgttcacagt taccgagaaa ccagaagtga tcgatgcgtc tgaattaaca   1320

ccagccgtga caacttacaa acttgttatt aatggtaaaa cattgaaagg cgaaacaact   1380

actaaagcag tagacgcaga aactgcagaa aaagccttca aacaatacgc taacgacaac   1440

ggtgttgatg gtgtttggac ttatgatgat gcgactaaga cctttacggt aactgaaggt   1500

ggtagcggcg gcggtatgaa agaaaccgct gctgctaaat tcgaacgcca gcacatggac   1560

agcccagatc tgggtgagta tatgccgatg gaaaatagcg ccgtcgacca ccaccatcat   1620

caccattaa                                                           1629
```

```
<210> SEQ ID NO 66
<211> LENGTH: 542
<212> TYPE: PRT
<213> ORGANISM: Artificial Sequence
<220> FEATURE:
<223> OTHER INFORMATION: Recombinant protein

<400> SEQUENCE: 66

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190
```

```
Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Val Pro Arg
    210                 215                 220

Gly Ser Pro Glu Phe Pro Gly Asn Ser Tyr Asp His Asp Tyr Ala Lys
225                 230                 235                 240

Leu Ser Thr Leu Tyr Arg Lys Val Gly Gly Gly Leu Glu Val Leu Phe
                245                 250                 255

Gln Gly Pro Glu Arg Pro Tyr Ala Cys Pro Val Glu Ser Cys Asp Arg
            260                 265                 270

Arg Phe Ser Arg Ser Asp Glu Leu Thr Arg His Ile Arg Ile His Thr
        275                 280                 285

Gly Gln Lys Pro Phe Gln Cys Arg Ile Cys Met Arg Asn Phe Ser Arg
    290                 295                 300

Ser Asp His Leu Thr Thr His Ile Arg Thr His Thr Gly Glu Lys Pro
305                 310                 315                 320

Phe Ala Cys Asp Ile Cys Gly Arg Lys Phe Ala Arg Ser Asp Glu Lys
                325                 330                 335

Ile His Leu Arg Gln Lys Asp Ala Ser Leu Tyr Lys Lys Ala Gly Ser
            340                 345                 350

Gly Gly Gly Gln Leu Gly Gly Ser Ser Ser Asn Pro Ala Phe Leu Tyr
        355                 360                 365

Lys Val Gly Gly Ser Ser Thr Tyr Lys Leu Ile Leu Asn Gly Lys Thr
    370                 375                 380

Leu Lys Gly Glu Thr Thr Thr Glu Ala Val Asp Ala Ala Thr Ala Glu
385                 390                 395                 400

Lys Val Phe Lys Gln Tyr Ala Asn Asp Asn Gly Val Asp Gly Glu Trp
                405                 410                 415

Thr Tyr Asp Asp Ala Thr Lys Thr Phe Thr Val Thr Glu Lys Pro Glu
            420                 425                 430

Val Ile Asp Ala Ser Glu Leu Thr Pro Ala Val Thr Thr Tyr Lys Leu
        435                 440                 445

Val Ile Asn Gly Lys Thr Leu Lys Gly Glu Thr Thr Thr Lys Ala Val
    450                 455                 460

Asp Ala Glu Thr Ala Glu Lys Ala Phe Lys Gln Tyr Ala Asn Asp Asn
465                 470                 475                 480

Gly Val Asp Gly Val Trp Thr Tyr Asp Asp Ala Thr Lys Thr Phe Thr
                485                 490                 495

Val Thr Glu Gly Gly Ser Gly Gly Gly Met Lys Glu Thr Ala Ala Ala
            500                 505                 510

Lys Phe Glu Arg Gln His Met Asp Ser Pro Asp Leu Gly Glu Tyr Met
        515                 520                 525

Pro Met Glu Asn Ser Ala Val Asp His His His His His His
    530                 535                 540
```

```
<210> SEQ ID NO 67
<211> LENGTH: 46
<212> TYPE: DNA
<213> ORGANISM: Artificial Sequence
<220> FEATURE:
<223> OTHER INFORMATION: DNA Probe

<400> SEQUENCE: 67

gatccccctc gcccacgcga tatcaaggct ccactaaata gacgca                46
```

<210> SEQ ID NO 68
<211> LENGTH: 24
<212> TYPE: DNA
<213> ORGANISM: Artificial Sequence
<220> FEATURE:
<223> OTHER INFORMATION: DNA Probe

<400> SEQUENCE: 68
gatatcgcgt gggcgagggg gatc 24

<210> SEQ ID NO 69
<211> LENGTH: 24
<212> TYPE: DNA
<213> ORGANISM: Artificial Sequence
<220> FEATURE:
<223> OTHER INFORMATION: DNA Probe

<400> SEQUENCE: 69
gatatcgcgt gggcgagggg gatc 24

<210> SEQ ID NO 70
<211> LENGTH: 46
<212> TYPE: DNA
<213> ORGANISM: Artificial Sequence
<220> FEATURE:
<223> OTHER INFORMATION: DNA Probe
<220> FEATURE:
<221> NAME/KEY: misc_feature
<222> LOCATION: (1)..(1)
<223> OTHER INFORMATION: Biotinylated

<400> SEQUENCE: 70
gatccccctc gcccacgcga tatcaaggct ccactaaata gacgca 46

<210> SEQ ID NO 71
<211> LENGTH: 45
<212> TYPE: DNA
<213> ORGANISM: Artificial Sequence
<220> FEATURE:
<223> OTHER INFORMATION: DNA Probe
<220> FEATURE:
<221> NAME/KEY: misc_signal
<222> LOCATION: (1)..(1)
<223> OTHER INFORMATION: Cyanine Cy3

<400> SEQUENCE: 71
ctctgacctt tcggtgacct ggcaaggctc cactaaatag acgca 45

<210> SEQ ID NO 72
<211> LENGTH: 992
<212> TYPE: PRT
<213> ORGANISM: Peptostreptococcus magnus

<400> SEQUENCE: 72

Met Lys Ile Asn Lys Lys Leu Leu Met Ala Ala Leu Ala Gly Ala Ile
1 5 10 15

Val Val Gly Gly Gly Ala Asn Ala Tyr Ala Ala Glu Glu Asp Asn Thr
20 25 30

Asp Asn Asn Leu Ser Met Asp Glu Ile Ser Asp Ala Tyr Phe Asp Tyr
35 40 45

His Gly Asp Val Ser Asp Ser Val Asp Pro Val Glu Glu Glu Ile Asp
50 55 60

Glu Ala Leu Ala Lys Ala Leu Ala Glu Ala Lys Glu Thr Ala Lys Lys
65 70 75 80

```
His Ile Asp Ser Leu Asn His Leu Ser Glu Thr Ala Lys Lys Leu Ala
                85                  90                  95

Lys Asn Asp Ile Asp Ser Ala Thr Thr Ile Asn Ala Ile Asn Asp Ile
            100                 105                 110

Val Ala Arg Ala Asp Val Met Glu Arg Lys Thr Ala Glu Lys Glu Glu
        115                 120                 125

Ala Glu Lys Leu Ala Ala Ala Lys Glu Thr Ala Lys Lys His Ile Asp
    130                 135                 140

Glu Leu Lys His Leu Ala Asp Lys Thr Lys Glu Leu Ala Lys Arg Asp
145                 150                 155                 160

Ile Asp Ser Ala Thr Thr Ile Asn Ala Ile Asn Asp Ile Val Ala Arg
                165                 170                 175

Ala Asp Val Met Glu Arg Lys Thr Ala Glu Lys Glu Glu Ala Glu Lys
            180                 185                 190

Leu Ala Ala Ala Lys Glu Thr Ala Lys Lys His Ile Asp Glu Leu Lys
        195                 200                 205

His Leu Ala Asp Lys Thr Lys Glu Leu Ala Lys Arg Asp Ile Asp Ser
    210                 215                 220

Ala Thr Thr Ile Asp Ala Ile Asn Asp Ile Val Ala Arg Ala Asp Val
225                 230                 235                 240

Met Glu Arg Lys Leu Ser Glu Lys Glu Thr Pro Glu Pro Glu Glu Glu
                245                 250                 255

Val Thr Ile Lys Ala Asn Leu Ile Phe Ala Asp Gly Ser Thr Gln Asn
            260                 265                 270

Ala Glu Phe Lys Gly Thr Phe Ala Lys Ala Val Ser Asp Ala Tyr Ala
        275                 280                 285

Tyr Ala Asp Ala Leu Lys Lys Asp Asn Gly Glu Tyr Thr Val Asp Val
    290                 295                 300

Ala Asp Lys Gly Leu Thr Leu Asn Ile Lys Phe Ala Gly Lys Lys Glu
305                 310                 315                 320

Lys Pro Glu Glu Pro Lys Glu Glu Val Thr Ile Lys Val Asn Leu Ile
                325                 330                 335

Phe Ala Asp Gly Lys Thr Gln Thr Ala Glu Phe Lys Gly Thr Phe Glu
            340                 345                 350

Glu Ala Thr Ala Lys Ala Tyr Ala Tyr Ala Asp Leu Leu Ala Lys Glu
        355                 360                 365

Asn Gly Glu Tyr Thr Ala Asp Leu Glu Asp Gly Gly Asn Thr Ile Asn
    370                 375                 380

Ile Lys Phe Ala Gly Lys Glu Thr Pro Glu Thr Pro Glu Glu Pro Lys
385                 390                 395                 400

Glu Glu Val Thr Ile Lys Val Asn Leu Ile Phe Ala Asp Gly Lys Ile
                405                 410                 415

Gln Thr Ala Glu Phe Lys Gly Thr Phe Glu Glu Ala Thr Ala Lys Ala
            420                 425                 430

Tyr Ala Tyr Ala Asn Leu Leu Ala Lys Glu Asn Gly Glu Tyr Thr Ala
        435                 440                 445

Asp Leu Glu Asp Gly Gly Asn Thr Ile Asn Ile Lys Phe Ala Gly Lys
    450                 455                 460

Glu Thr Pro Glu Thr Pro Glu Glu Pro Lys Glu Glu Val Thr Ile Lys
465                 470                 475                 480

Val Asn Leu Ile Phe Ala Asp Gly Lys Thr Gln Thr Ala Glu Phe Lys
                485                 490                 495

Gly Thr Phe Glu Glu Ala Thr Ala Glu Ala Tyr Arg Tyr Ala Asp Leu
```

-continued

```
            500                 505                 510

Leu Ala Lys Val Asn Gly Glu Tyr Thr Ala Asp Leu Glu Asp Gly Gly
        515                 520                 525

Tyr Thr Ile Asn Ile Lys Phe Ala Gly Lys Glu Gln Pro Gly Glu Asn
    530                 535                 540

Pro Gly Ile Thr Ile Asp Glu Trp Leu Leu Lys Asn Ala Lys Glu Glu
545                 550                 555                 560

Ala Ile Lys Glu Leu Lys Glu Ala Gly Ile Thr Ser Asp Leu Tyr Phe
                565                 570                 575

Ser Leu Ile Asn Lys Ala Lys Thr Val Glu Gly Val Glu Ala Leu Lys
            580                 585                 590

Asn Glu Ile Leu Lys Ala His Ala Gly Glu Glu Thr Pro Glu Leu Lys
        595                 600                 605

Asp Gly Tyr Ala Thr Tyr Glu Glu Ala Glu Ala Ala Ala Lys Glu Ala
    610                 615                 620

Leu Lys Asn Asp Asp Val Asn Asn Ala Tyr Glu Ile Val Gln Gly Ala
625                 630                 635                 640

Asp Gly Arg Tyr Tyr Tyr Val Leu Lys Ile Glu Val Ala Asp Glu Glu
                645                 650                 655

Glu Pro Gly Glu Asp Thr Pro Glu Val Gln Glu Gly Tyr Ala Thr Tyr
            660                 665                 670

Glu Glu Ala Glu Ala Ala Ala Lys Glu Ala Leu Lys Glu Asp Lys Val
        675                 680                 685

Asn Asn Ala Tyr Glu Val Val Gln Gly Ala Asp Gly Arg Tyr Tyr Tyr
    690                 695                 700

Val Leu Lys Ile Glu Asp Lys Glu Asp Glu Gln Pro Gly Glu Glu Pro
705                 710                 715                 720

Gly Glu Asn Pro Gly Ile Thr Ile Asp Glu Trp Leu Leu Lys Asn Ala
                725                 730                 735

Lys Glu Asp Ala Ile Lys Glu Leu Lys Glu Ala Gly Ile Ser Ser Asp
            740                 745                 750

Ile Tyr Phe Asp Ala Ile Asn Lys Ala Lys Thr Val Glu Gly Val Glu
        755                 760                 765

Ala Leu Lys Asn Glu Ile Leu Lys Ala His Ala Glu Lys Pro Gly Glu
    770                 775                 780

Asn Pro Gly Ile Thr Ile Asp Glu Trp Leu Leu Lys Asn Ala Lys Glu
785                 790                 795                 800

Ala Ala Ile Lys Glu Leu Lys Glu Ala Gly Ile Thr Ala Glu Tyr Leu
                805                 810                 815

Phe Asn Leu Ile Asn Lys Ala Lys Thr Val Glu Gly Val Glu Ser Leu
            820                 825                 830

Lys Asn Glu Ile Leu Lys Ala His Ala Glu Lys Pro Gly Glu Asn Pro
        835                 840                 845

Gly Ile Thr Ile Asp Glu Trp Leu Leu Lys Asn Ala Lys Glu Asp Ala
    850                 855                 860

Ile Lys Glu Leu Lys Glu Ala Gly Ile Thr Ser Asp Ile Tyr Phe Asp
865                 870                 875                 880

Ala Ile Asn Lys Ala Lys Thr Ile Glu Gly Val Glu Ala Leu Lys Asn
                885                 890                 895

Glu Ile Leu Lys Ala His Lys Lys Asp Glu Glu Pro Gly Lys Lys Pro
            900                 905                 910

Gly Glu Asp Lys Lys Pro Glu Asp Lys Lys Pro Gly Glu Asp Lys Lys
        915                 920                 925
```

```
Pro Glu Asp Lys Lys Pro Gly Glu Asp Lys Lys Pro Glu Asp Lys Lys
    930                 935                 940

Pro Gly Lys Thr Asp Lys Asp Ser Pro Asn Lys Lys Lys Lys Ala Lys
945                 950                 955                 960

Leu Pro Lys Ala Gly Ser Glu Ala Glu Ile Leu Thr Leu Ala Ala Ala
                965                 970                 975

Ala Leu Ser Thr Ala Ala Gly Ala Tyr Val Ser Leu Lys Lys Arg Lys
            980                 985                 990
```

<210> SEQ ID NO 73
<211> LENGTH: 17
<212> TYPE: DNA
<213> ORGANISM: Artificial Sequence
<220> FEATURE:
<223> OTHER INFORMATION: Recombinant Protein
<220> FEATURE:
<221> NAME/KEY: misc_feature
<222> LOCATION: (7)..(11)
<223> OTHER INFORMATION: n is a, c, g, or t

<400> SEQUENCE: 73
aggtcannnn naggtca 17

<210> SEQ ID NO 74
<211> LENGTH: 16
<212> TYPE: DNA
<213> ORGANISM: Artificial Sequence
<220> FEATURE:
<223> OTHER INFORMATION: Recombinant Protein
<220> FEATURE:
<221> NAME/KEY: misc_feature
<222> LOCATION: (7)..(10)
<223> OTHER INFORMATION: n is a, c, g, or t

<400> SEQUENCE: 74
aggtcannnn aggtca 16

<210> SEQ ID NO 75
<211> LENGTH: 15
<212> TYPE: DNA
<213> ORGANISM: Artificial Sequence
<220> FEATURE:
<223> OTHER INFORMATION: Recombinant Protein
<220> FEATURE:
<221> NAME/KEY: misc_feature
<222> LOCATION: (7)..(9)
<223> OTHER INFORMATION: n is a, c, g, or t

<400> SEQUENCE: 75
aggtcannna ggtca 15

<210> SEQ ID NO 76
<211> LENGTH: 14
<212> TYPE: DNA
<213> ORGANISM: Artificial Sequence
<220> FEATURE:
<223> OTHER INFORMATION: Recombinant Protein
<220> FEATURE:
<221> NAME/KEY: misc_feature
<222> LOCATION: (7)..(8)
<223> OTHER INFORMATION: n is a, c, g, or t

<400> SEQUENCE: 76
aggtcannag gtca 14

<210> SEQ ID NO 77

<211> LENGTH: 13
<212> TYPE: DNA
<213> ORGANISM: Artificial Sequence
<220> FEATURE:
<223> OTHER INFORMATION: Recombinant Protein
<220> FEATURE:
<221> NAME/KEY: misc_feature
<222> LOCATION: (7)..(7)
<223> OTHER INFORMATION: n is a, c, g, or t

<400> SEQUENCE: 77
aggtcanagg tca 13

<210> SEQ ID NO 78
<211> LENGTH: 357
<212> TYPE: DNA
<213> ORGANISM: Artificial Sequence
<220> FEATURE:
<223> OTHER INFORMATION: Recombinant Protein

<400> SEQUENCE: 78
actttgtata gaaaagttgg tggtggcctg gaagttctgt tccaggggcc ctccttcacc 60
aagcacatct gcgccatctg cggggaccgc tcctcaggca agcactatgg agtgtacagc 120
tgcgaggggt gcaagggctt cttcaagcgg acggtgcgca aggacctgac ctacacctgc 180
cgcgacaaca aggactgcct gattgacaag cggcagcgga accggtgcca gtactgccgc 240
taccagaagt gcctggccat gggcatgaag cgggaagccg tgcaggagga gcggcagcgt 300
ggcaaggacc ggaacgagaa tgaggtggag tcgaccagcg caagtttgta caaaaaa 357

<210> SEQ ID NO 79
<211> LENGTH: 119
<212> TYPE: PRT
<213> ORGANISM: Artificial Sequence
<220> FEATURE:
<223> OTHER INFORMATION: Recombinant Protein

<400> SEQUENCE: 79

Thr Leu Tyr Arg Lys Val Gly Gly Gly Leu Glu Val Leu Phe Gln Gly
1 5 10 15

Pro Ser Phe Thr Lys His Ile Cys Ala Ile Cys Gly Asp Arg Ser Ser
20 25 30

Gly Lys His Tyr Gly Val Tyr Ser Cys Glu Gly Cys Lys Gly Phe Phe
35 40 45

Lys Arg Thr Val Arg Lys Asp Leu Thr Tyr Thr Cys Arg Asp Asn Lys
50 55 60

Asp Cys Leu Ile Asp Lys Arg Gln Arg Asn Arg Cys Gln Tyr Cys Arg
65 70 75 80

Tyr Gln Lys Cys Leu Ala Met Gly Met Lys Arg Glu Ala Val Gln Glu
85 90 95

Glu Arg Gln Arg Gly Lys Asp Arg Asn Glu Asn Glu Val Glu Ser Thr
100 105 110

Ser Ala Ser Leu Tyr Lys Lys
115

<210> SEQ ID NO 80
<211> LENGTH: 357
<212> TYPE: DNA
<213> ORGANISM: artificial sequence
<220> FEATURE:
<223> OTHER INFORMATION: recombinant protein

<400> SEQUENCE: 80

-continued

```
actttgtata gaaaagttgg tggtggcctg gaagttctgt tccaggggcc cccccgcatc     60

tacaagcctt gctttgtctg tcaggacaag tcctcaggct accactatgg ggtcagcgcc    120

tgtgagggct gcaagggctt cttccgccgc agcatccaga agaacatggt gtacacgtgt    180

caccgggaca agaactgcat catcaacaag gtgacccgga accgctgcca gtactgccga    240

ctgcagaagt gctttgaagt gggcatgtcc aaggagtctg tgagaaacga ccgaaacaag    300

aagaagaagg aggtgcccaa gcccgagtgc tctgagagcg caagtttgta caaaaaa       357


<210> SEQ ID NO 81
<211> LENGTH: 119
<212> TYPE: PRT
<213> ORGANISM: Artificial Sequence
<220> FEATURE:
<223> OTHER INFORMATION: recombinant protein

<400> SEQUENCE: 81

Thr Leu Tyr Arg Lys Val Gly Gly Gly Leu Glu Val Leu Phe Gln Gly
1               5                   10                  15

Pro Pro Arg Ile Tyr Lys Pro Cys Phe Val Cys Gln Asp Lys Ser Ser
            20                  25                  30

Gly Tyr His Tyr Gly Val Ser Ala Cys Glu Gly Cys Lys Gly Phe Phe
        35                  40                  45

Arg Arg Ser Ile Gln Lys Asn Met Val Tyr Thr Cys His Arg Asp Lys
    50                  55                  60

Asn Cys Ile Ile Asn Lys Val Thr Arg Asn Arg Cys Gln Tyr Cys Arg
65                  70                  75                  80

Leu Gln Lys Cys Phe Glu Val Gly Met Ser Lys Glu Ser Val Arg Asn
                85                  90                  95

Asp Arg Asn Lys Lys Lys Lys Glu Val Pro Lys Pro Glu Cys Ser Glu
            100                 105                 110

Ser Ala Ser Leu Tyr Lys Lys
        115
```